(12) United States Patent
Han et al.

(10) Patent No.: US 9,340,513 B2
(45) Date of Patent: May 17, 2016

(54) PROPENOATE DERIVATIVES OF BETULIN

(71) Applicant: GlaxoSmithKline LLC, Philadelphia, PA (US)

(72) Inventors: Nianhe Han, Shanghai (CN); Brian Alvin Johns, Research Triangle Park, NC (US); Jun Tang, Research Triangle Park, NC (US)

(73) Assignee: GlaxoSmithKline LLC, Wilmington, DE (US)

( * ) Notice: Subject to any disclaimer, the term of this patent is extended or adjusted under 35 U.S.C. 154(b) by 73 days.

(21) Appl. No.: 14/364,409

(22) PCT Filed: Dec. 14, 2012

(86) PCT No.: PCT/US2012/069688
§ 371 (c)(1),
(2) Date: Jun. 11, 2014

(87) PCT Pub. No.: WO2013/090683
PCT Pub. Date: Jun. 20, 2013

(65) Prior Publication Data
US 2014/0350032 A1    Nov. 27, 2014

(30) Foreign Application Priority Data

Dec. 14, 2011   (WO) ................ PCT/CN2011/002105
Dec. 21, 2011   (WO) ................ PCT/CN2011/002159

(51) Int. Cl.
| C07J 53/00 | (2006.01) |
| A61K 31/56 | (2006.01) |
| C07D 239/30 | (2006.01) |
| C07C 69/34 | (2006.01) |
| C07C 235/78 | (2006.01) |
| C07D 213/61 | (2006.01) |
| C07J 63/00 | (2006.01) |

(52) U.S. Cl.
CPC .............. *C07D 239/30* (2013.01); *C07C 69/34* (2013.01); *C07C 235/78* (2013.01); *C07D 213/61* (2013.01); *C07J 63/008* (2013.01); *C07C 2103/52* (2013.01)

(58) Field of Classification Search
CPC ....................................................... C07J 63/008
USPC .......................................... 552/510; 514/169
See application file for complete search history.

(56) References Cited

U.S. PATENT DOCUMENTS

| 2006/0205697 A1 | 9/2006 | Robinson et al. |
| 2010/0240630 A1 | 9/2010 | Kumar et al. |
| 2011/0218204 A1 | 9/2011 | Reddy et al. |

FOREIGN PATENT DOCUMENTS

| WO | WO2008057420 | 5/2008 |
| WO | WO2011100308 | 8/2011 |

*Primary Examiner* — Barbara P Badio
(74) *Attorney, Agent, or Firm* — Robert H. Brink

(57) ABSTRACT

The present invention relates to a compound characterized by the following Formula I:

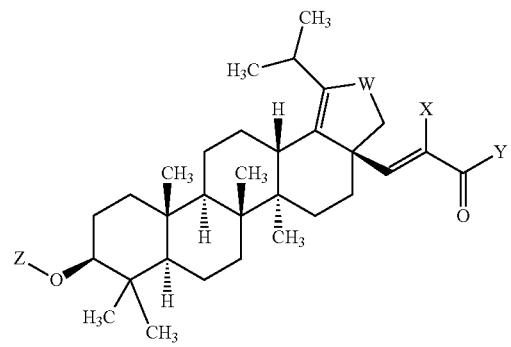

Formula I or a pharmaceutically acceptable salt thereof, wherein X, Y, and Z are as described herein. Compounds of the present invention are useful for the treatment of HIV.

27 Claims, No Drawings

PROPENOATE DERIVATIVES OF BETULIN

CROSS-REFERENCE TO RELATED APPLICATIONS

This application is filed pursuant to 35 USC 371 as a United States National Phase Application of International Patent Application Serial No. PCT/US2012/069688 filed on Dec. 14, 2012, which claims priority from PCT/CN2011/002159 filed in China on Dec. 21, 2011 and from PCT/CN2011/002105 filed in China on Dec. 14, 2011.

FIELD OF THE INVENTION

The present invention relates to propenoate derivative compounds, pharmaceutical compositions, and methods of use thereof for (i) inhibiting HIV replication in a subject infected with HIV, or (ii) treating a subject infected with HIV, by administering such compounds.

BACKGROUND OF THE INVENTION

Presently, long-term suppression of viral replication with antiretroviral drugs is the only option for treating HIV-1 infection. To date, a number of approved drugs have been shown to greatly increase patient survival. However, therapeutic regimens known as highly active antiretroviral therapy (HAART) are often complex because a combination of different drugs must be administered to the patient to avoid the rapid emergence of drug-resistant HIV-1 variants. Despite the positive impact of HAART on patient survival, drug resistance can still occur.

The emergence of multidrug-resistant (MDR) HIV-1 isolates has serious clinical consequences and must be suppressed with a new drug regimen, known as salvage therapy. Current guidelines recommend that salvage therapy includes at least two, and preferably three, fully active drugs. Typically, first-line therapies combine three to four drugs targeting the viral enzymes RT and protease (PR). One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase (IN) inhibitors. However, resistance to all three new drug classes has already been reported both in vitro and in vivo. Sustained successful treatment of HIV-1-infected patients with antiretroviral drugs will therefore require the continued development of new and improved drugs with new targets and mechanisms of action.

The HIV Gag polyprotein precursor (Pr55Gag), which is composed of four protein domains—matrix (MA), capsid (CA), nucleocapsid (NC) and p6—and two spacer peptides, SP1 and SP2, represents a new therapeutic target. Although the cleavage of the Gag polyprotein plays a central role in the progression of infectious virus particle production, to date, no antiretroviral drug has been approved for this mechanism.

In most cell types, assembly occurs at the plasma membrane, and the MA domain of Gag mediates membrane binding. Assembly is completed by budding of the immature particle from the cell. Concomitant with particle release, the virally encoded PR cleaves Gag into the four mature protein domains, MA, CA, NC and p6, and the two spacer peptides, SP1 and SP2. Gag-Pol is also cleaved by PR, liberating the viral enzymes PR, RT and IN. Gag proteolytic processing induces a morphological rearrangement within the particle, known as maturation. Maturation converts the immature, donut-shaped particle to the mature virion, which contains a condensed conical core composed of a CA shell surrounding the viral RNA genome in a complex with NC and the viral enzymes RT and IN. Maturation prepares the virus for infection of a new cell and is absolutely essential for particle infectivity.

Bevirimat (PA-457) is a maturation inhibitor that inhibits the final step in the processing of Gag, the conversion of capsid-SP1 (p25) to capsid, which is required for the formation of infectious viral particles. Bevirimat has activity against ART-resistant and wild-type HIV, and has shown synergy with antiretrovirals from all classes. Bevirimat reduced HIV viral load by a mean of 1.3 $\log_{10}$/mL in patients who achieved trough levels of >=20 μg/mL and who did not have any of the key baseline Gag polymorphisms at Q369, V370 or T371. However, Bevirimat users with Gag polymorphisms at Q369, V370 or T371 demonstrated significantly lower load reductions than patients without Gag polymorphisms at these sites.

It would therefore be an advance in the art to discover alternative compounds that are effective for the prevention and/or treatment of HIV infections.

SUMMARY OF THE INVENTION

In accordance with one embodiment of the present invention, there is provided a compound of Formula I:

Formula I

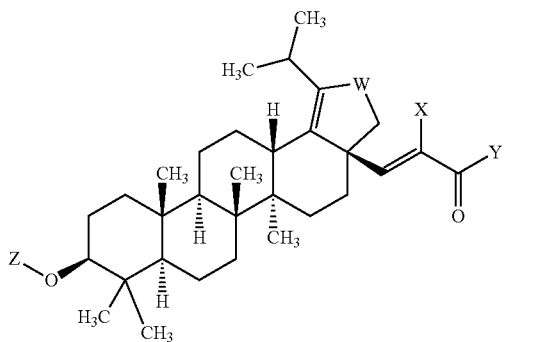

(I)

or a pharmaceutically acceptable salt thereof, wherein:

W is selected from —CH$_2$— or —C(=O)—;

X is selected from the group consisting of H, (C$_1$-C$_6$)alkyl, (C$_2$-C$_6$)alkenyl, (C$_2$-C$_6$)alkynyl, NH$_2$, —CN, —C(O)R$^6$, -(Q)$_n$R$^3$, —(C$_1$-C$_6$)alkyl-N(R$^3$)$_2$, —(C$_1$-C$_6$)alkyl-OR$^3$— (C$_1$-C$_6$)alkoxy, and amino-(C$_1$-C$_6$)alkyl;

Y is selected from —NR$^1$R$^2$ or —OR$^5$;

Z is

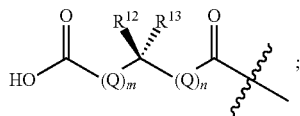

R$^1$ is selected from the group consisting of H, (C$_1$-C$_{12}$) alkyl, (C$_2$-C$_{12}$)alkenyl, (C$_2$-C$_{12}$)alkynyl, —(C$_1$-C$_6$)alkyl-N (R$^3$)$_2$, —(C$_1$-C$_6$)alkyl-OR$^3$;

$R^2$ is selected from the group consisting of H, $(C_1-C_{12})$alkyl, $(C_2-C_{12})$alkenyl, $(C_2-C_{12})$alkynyl, and $-(Q)_nR^3$;

$R^1$ and $R^2$ can optionally join together along with the nitrogen to which they are joined to form a 4 to 12 membered heterocyclyl or heteroaryl ring, each independently containing one to three heteroatoms selected from $-NR^5-$, $-O-$, $-S-$, $-S(O)-$, or $-SO_2-$, and wherein said heterocyclyl or heteroaryl ring may be also optionally and independently substituted with one to three $R^{10}$ groups;

$R^3$ is independently selected from the group consisting of H, $(C_1-C_6)$alkyl, $-R^4$, $-C(O)R^4$, $-CO_2R^4$,

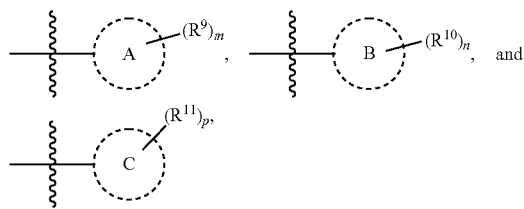

wherein:

A is $(C_5-C_{14})$aryl,

B is selected from $(C_2-C_9)$heterocycle or $(C_2-C_9)$heteroaryl, each having one to three heteroatoms selected from S, N or O, and C is $(C_3-C_8)$cycloalkyl;

$R^4$ is independently selected from the group consisting of halo, oxo, $(C_1-C_6)$alkyl, $(C_1-C_6)$alkoxy, $(C_3-C_8)$cycloalkyl; $-CF_3$, $-OCF_3$, $-N(R^5)_2$, $-(CH_2)_r$-heterocycle, $-C(O)OH$, $-C(O)NH_2$, and $-NO_2$;

$R^5$ is selected from the group consisting of H, $(C_1-C_6)$alkyl, and $(C_3-C_8)$cycloalkyl;

$R^6$ is independently H, $(C_1-C_6)$alkyl, $(C_3-C_8)$cycloalkyl, $(C_1-C_6)$alkoxy, haloalkyl, $OCF_3$, $-NR^7R^8$, heterocycle, $-(CH_2)_rNR^7R^8$, $-C(O)OH$, $-C(O)NH_2$, wherein two $R^6$ groups can optionally be taken together with the carbon to which they are joined to form a 3 to 8 membered cycloalkyl ring, wherein the cycloalkyl ring may be optionally substituted by one to three $R^{10}$ groups;

$R^7$ and $R^8$ are independently selected from the group consisting of $(C_1-C_6)$alkyl, $(C_3-C_8)$cycloalkyl, -Q-aryl-$(R^4)_n$, $-NR^{14}R^{15}$, $-C(O)CH_3$, wherein $R^7$ and $R^8$ can optionally be taken together with the nitrogen to which they are joined to form a 4 to 8 membered heterocyclyl or heteroaryl ring containing one to three heteroatoms selected from $-NR^5-$, $-O-$, $-S-$, $-S(O)-$, or $-SO_2-$, wherein the heterocyclyl or heteroaryl ring may be optionally substituted by one to three $R^{10}$ groups;

$R^9$, $R^{10}$, and $R^{11}$ are independently selected from the group consisting of oxo, halo, $(C_1-C_6)$alkoxy, $-R^3(R^6)_q$, $-OR^3(R^6)_q$, nitro, $-NR^{14}R^{15}$, $-SO_2R^3$, $(C_1-C_6)$alkyl, $-C(O)R^7$, $-R^1YR^3$, and $-CO(O)R^2$, wherein any two $R^9$, $R^{10}$ or $R^{11}$ groups can optionally join to form a 3 to 8 membered cycloalkyl, aryl, heterocyclyl or heteroaryl ring, wherein the heterocyclyl or heteroaryl ring may contain one to three heteroatoms selected from $-NR^5-$, $-O-$, $-S-$, $-S(O)-$, or $-SO_2-$, and wherein the cycloalkyl, aryl, heterocyclyl or heteroaryl ring may be optionally substituted by one to three $R^4$ groups;

$R^{12}$ and $R^{13}$ are independently selected from the group consisting of H, $(C_1-C_6)$alkyl, $(C_3-C_8)$cycloalkyl, $(C_1-C_6)$alkoxy, $-[C(R^6)_2]_r-$, $-O[C(R^6)_2]_r-$, Oxo, halo, $-C(O)R^7$, $-NR^1R^2$, and $-CO(O)R^2$, wherein $R^{12}$ and $R^{13}$ can optionally be taken together with the carbon to which they are joined to form a 3 to 8 membered cycloalkyl ring or 4 to 8 membered heterocyclyl ring containing one to three heteroatoms selected from $-NR^5-$, $-O-$, $-S-$, $-S(O)-$, $-SO_2-$, wherein the cycloalkyl ring or heterocyclyl ring may be optionally substituted by one to three $R^{10}$ groups;

$R^{14}$ and $R^{15}$ are independently selected from the group consisting of H, $(C_1-C_6)$alkyl, $(C_3-C_8)$cycloalkyl, $(C_1-C_6)$alkoxy, $-R^3(R^6)_q$, and $-OR^3(R^6)_q$, wherein $R^{14}$ and $R^{15}$ may be taken together with the nitrogen to which they are joined to form a 4 to 8 membered heterocyclyl or heteroaryl ring optionally containing one or three heteroatoms from $-NR^5-$, $-O-$, $-S-$, $-S(O)-$, or $-SO_2-$, wherein the heterocyclyl or heteroaryl ring may be optionally substituted by one to three $R^{10}$ groups;

Q is $-[C(R^6)_2]_r-$;

m and n are independently 0, 1, 2, 3, or 4;

p is independently 0, 1, 2, 3, or 4; and r and q are independently 0, 1, 2, 3, or 4.

In a second aspect, the present invention relates to a composition comprising a) the compound of Formula I or a pharmaceutically acceptable salt the thereof; and b) a pharmaceutically acceptable excipient.

In a third aspect, the present invention is a method of treating HIV comprising administering to a patient suffering therefrom an effective amount of the compound of Formula I or a pharmaceutically acceptable salt thereof.

Compounds of the present invention are useful for the treatment of patients with HIV.

DETAILED DESCRIPTION OF REPRESENTATIVE EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

As used herein unless otherwise specified, "alkyl" refers to to a monovalent saturated aliphatic hydrocarbyl group having from 1 to 14 carbon atoms and, in some embodiments, from 1 to 6 carbon atoms. "$(C_x-C_y)$alkyl" refers to alkyl groups having from x to y carbon atoms. The term "alkyl" includes, by way of example, linear and branched hydrocarbyl groups such as methyl ($CH_3-$), ethyl ($CH_3CH_2-$), n-propyl ($CH_3CH_2CH_2-$), isopropyl (($CH_3)_2CH-$), n-butyl ($CH_3CH_2CH_2CH_2-$), isobutyl (($CH_3)_2CHCH_2-$), sec-butyl (($CH_3)(CH_3CH_2)CH-$), t-butyl (($CH_3)_3C-$), n-pentyl ($CH_3CH_2CH_2CH_2CH_2-$), and neopentyl (($CH_3)^3CCH_2-$).

"Alkylene" or "alkylene" refers to divalent saturated aliphatic hydrocarbyl groups having from 1 to 10 carbon atoms and, in some embodiments, from 1 to 6 carbon atoms. "$(C_u-C_v)$alkylene" refers to alkylene groups having from u to v carbon atoms. The alkylene groups include branched and straight chain hydrocarbyl groups. For example, "$(C_1-C_6)$alkylene" is meant to include methylene, ethylene, propylene, 2-methypropylene, dimethylethylene, pentylene, and so forth. As such, the term "propylene" could be exemplified by the following structure:

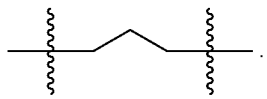 [SMILES: *CCC*]

Likewise, the term "dimethylbutylene" could be exemplified by any of the following three structures or more:

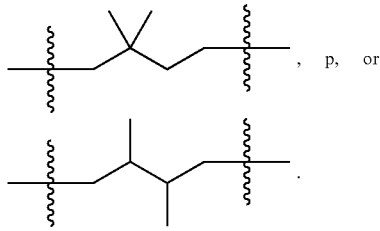, p, or

Furthermore, the term "$(C_1-C_6)$alkylene" is meant to include such branched chain hydrocarbyl groups as cyclopropylmethylene, which could be exemplified by the following structure:

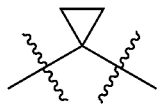

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, $(C_x-C_y)$alkenyl refers to alkenyl groups having from x to y carbon atoms and is meant to include for example, ethenyl, propenyl, isopropylene, 1,3-butadienyl, and the like.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $(C_2-C_6)$alkynyl is meant to include ethynyl, propynyl, and the like.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Acyl" refers to the groups H—C(O)—, alkyl-C(O)—, alkenyl-C(O)—, alkynyl-C(O)—, cycloalkyl-C(O)—, aryl-C(O)—, heteroaryl-C(O)—, and heterocyclic-C(O)—. Acyl includes the "acetyl" group $CH_3C(O)$—.

"Acylamino" refers to the groups —$NR^{20}$C(O)alkyl, —$NR^{20}$C(O)cycloalkyl, —$NR^{20}$C(O)alkenyl, —$NR^{20}$C(O)alkynyl, —$NR^{20}$C(O)aryl, —$NR^{20}$C(O)heteroaryl, and —$NR^{20}$C(O)heterocyclic, wherein $R^{20}$ is hydrogen or alkyl.

"Acyloxy" refers to the groups alkyl-C(O)O—, alkenyl-C(O)O—, alkynyl-C(O)O—, aryl-C(O)O—, cycloalkyl-C(O)O—, heteroaryl-C(O)O—, and heterocyclic-C(O)O—.

"Amino" refers to the group —$NR^{21}R^{22}$ where $R^{21}$ and $R^{22}$ are independently selected from hydrogen, alkyl, alkenyl, alkynyl, aryl, cycloalkyl, heteroaryl, heterocyclic, —$SO_2$-alkyl, —$SO_2$-alkenyl, —$SO_2$-cycloalkyl, —$SO_2$-aryl, —$SO_2$-heteroaryl, and —$SO_2$-heterocyclic, and wherein $R^{21}$ and $R^{22}$ are optionally joined together with the nitrogen bound thereto to form a heterocyclic group. When $R^{21}$ is hydrogen and $R^{22}$ is alkyl, the amino group is sometimes referred to herein as alkylamino. When $R^{21}$ and $R^{22}$ are alkyl, the amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)$NR^{26}R^{27}$ where $R^{26}$ and $R^{27}$ are independently selected from hydrogen, alkyl, alkenyl, alkynyl, aryl, cycloalkyl, heteroaryl, heterocyclic, hydroxy, alkoxy, amino, and acylamino, and where $R^{26}$ and $R^{27}$ are optionally joined together with the nitrogen bound thereto to form a heterocyclic group.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"Cyano" or "nitrile" refers to the group —CN.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "Cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are exemplified and named below: bicyclohexyl, and bicyclohexyl.

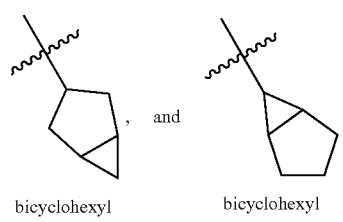

bicyclohexyl       bicyclohexyl

"$(C_u-C_v)$cycloalkyl" refers to cycloalkyl groups having u to v carbon atoms.

"Spiro cycloalkyl" refers to a 3 to 10 member cyclic substituent formed by replacement of two hydrogen atoms at a common carbon atom in a cyclic ring structure or in an alkylene group having 2 to 9 carbon atoms, as exemplified by the following structure wherein the group shown here attached to bonds marked with wavy lines is substituted with a spiro cycloalkyl group:

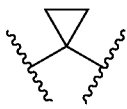

"Fused cycloalkyl" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused cycloalkyl group:

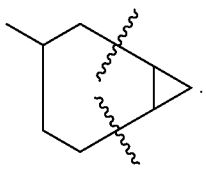

"Carboxy" or "carboxyl" refers interchangeably to the groups

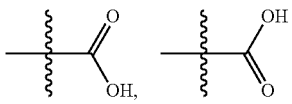

—C(O)O, or —CO$_2$.

"Halo" or "halogen" refers to fluoro, chloro, bromo, and iodo.

"Haloalkoxy" refers to substitution of alkoxy groups with 1 to 5 (e.g. when the alkoxy group has at least 2 carbon atoms) or in some embodiments 1 to 3 halo groups (e.g. trifluoromethoxy).

"Hydroxy" or "hydroxyl" refers to the group —OH.

"Heteroaryl" refers to an aromatic group of from 1 to 14 carbon atoms and 1 to 6 heteroatoms selected from oxygen, nitrogen, and sulfur and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

"Fused heterocyclic" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

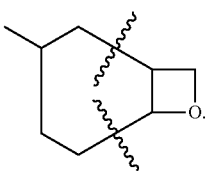

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of nitrogen, such as N(O) {N$^+$—O$^-$} and sulfur such as S(O) and S(O)$_2$, and the quaternized form of any basic nitrogen.

"Oxazolidinone" refers to a 5-membered heterocyclic ring containing one nitrogen and one oxygen as heteroatoms and also contains two carbons and is substituted at one of the two carbons by a carbonyl group as exemplified by any of the following structures, wherein the oxazolidinone groups shown here are bonded to a parent molecule, which is indicated by a wavy line in the bond to the parent molecule:

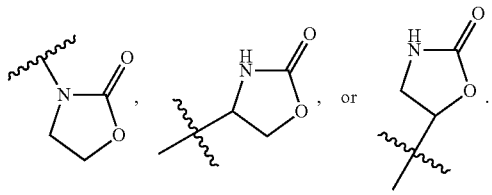 [SMILES: *N1CCOC1=O ; *C1COC(=O)N1 ; *C1CNC(=O)O1]

"Racemates" refers to a mixture of enantiomers. In an embodiment of the invention, the compounds of Formula I, or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species [Eliel ref]. One skilled in the art will recognize that upon installing a non-symmetrical $R^x$ to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" refers to mammals and includes humans and non-human mammals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

The present invention includes compounds as well as their pharmaceutically acceptable salts. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—C($R^x$)$_2$", it should be understood that the two $R^x$ groups can be the same, or they can be different if $R^x$ is defined as having more than one possible identity. In addition, certain substituents are drawn as —$R^xR^y$, where the "—" indicates a bond adjacent to the parent molecule and $R^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

In accordance with one embodiment of the present invention, there is provided a compound of Formula I:

Formula I

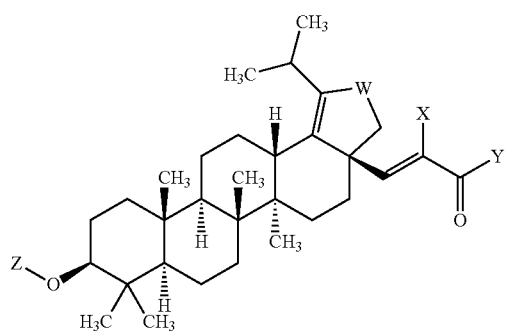

(I)

or a pharmaceutically acceptable salt thereof, wherein:
W is selected from —CH$_2$— or —C(=O)—;
X is selected from the group consisting of H, ($C_1$-$C_6$)alkyl, ($C_2$-$C_6$)alkenyl, ($C_2$-$C_6$)alkynyl, NH$_2$, —CN, —C(O)$R^6$, —(Q)$_n$R$^3$, —(C$_1$-C$_6$)alkyl-N(R$^3$)$_2$, —(C$_1$-C$_6$)alkyl-OR$^3$—(C$_1$-C$_6$)alkoxy, and amino-(C$_1$-C$_6$)alkyl;

Y is selected from —NR$^1$R$^2$ or —OR$^5$;

Z is

[structure: HO—C(O)—(Q)$_m$—C(R$^{12}$)(R$^{13}$)—(Q)$_n$—C(O)—];

R$^1$ is selected from the group consisting of H, (C$_1$-C$_{12}$)alkyl, (C$_2$-C$_{12}$)alkenyl, (C$_2$-C$_{12}$)alkynyl, —(C$_1$-C$_6$)alkyl-N(R$^3$)$_2$, —(C$_1$-C$_6$)alkyl-OR$^3$;

R$^2$ is selected from the group consisting of H, (C$_1$-C$_{12}$)alkyl, (C$_2$-C$_{12}$)alkenyl, (C$_2$-C$_{12}$)alkynyl, and -(Q)$_n$R$^3$;

R$^1$ and R$^2$ can optionally join together along with the nitrogen to which they are joined to form a 4 to 12 membered heterocyclyl or heteroaryl ring, each independently containing one to three heteroatoms selected from —NR$^5$—, —O—, —S—, —S(O)—, or —SO$_2$—, and wherein said heterocyclyl or heteroaryl ring may be also optionally and independently substituted with one to three R$^{10}$ groups;

R$^3$ is independently selected from the group consisting of H, (C$_1$-C$_6$)alkyl, —R$^4$, —C(O)R$^4$, —CO$_2$R$^4$,

[structures: A ring with (R$^9$)$_m$, B ring with (R$^{10}$)$_n$, and C ring with (R$^{11}$)$_p$], wherein:
A is (C$_5$-C$_{14}$)aryl,
B is selected from (C$_2$-C$_9$)heterocycle or (C$_2$-C$_9$)heteroaryl, each having one to three heteroatoms selected from S, N or O, and
C is (C$_3$-C$_8$)cycloalkyl;

R$^4$ is independently selected from the group consisting of halo, oxo, (C$_1$-C$_6$)alkyl, (C$_1$-C$_6$)alkoxy, (C$_3$-C$_8$)cycloalkyl; —CF$_3$, —OCF$_3$, —N(R$^5$)$_2$, —(CH$_2$)$_r$-heterocycle, —C(O)OH, —C(O)NH$_2$, and —NO$_2$;

R$^5$ is selected from the group consisting of H, (C$_1$-C$_6$)alkyl, and (C$_3$-C$_8$)cycloalkyl;

R$^6$ is independently H, (C$_1$-C$_6$)alkyl, (C$_3$-C$_8$)cycloalkyl, (C$_1$-C$_6$)alkoxy, haloalkyl, —OCF$_3$, —NR$^7$R$^8$, heterocycle, —(CH$_2$)$_r$NR$^7$R$^8$, —C(O)OH, —C(O)NH$_2$, wherein two R$^6$ groups can optionally be taken together with the carbon to which they are joined to form a 3 to 8 membered cycloalkyl ring, wherein the cycloalkyl ring may be optionally substituted by one to three R$^{10}$ groups;

R$^7$ and R$^8$ are independently selected from the group consisting of (C$_1$-C$_6$)alkyl, (C$_3$-C$_8$)cycloalkyl, -Q-aryl-(R$^4$)$_n$, —NR$^{14}$R$^{15}$, —C(O)CH$_3$, wherein R$^7$ and R$^8$ can optionally be taken together with the nitrogen to which they are joined to form a 4 to 8 membered heterocyclyl or heteroaryl ring containing one to three heteroatoms selected from —NR$^5$—, —O—, —S—, —S(O)—, or —SO$_2$—, wherein the heterocyclyl or heteroaryl ring may be optionally substituted by one to three R$^{10}$ groups;

R$^9$, R$^{10}$, and R$^{11}$ are independently selected from the group consisting of oxo, halo, (C$_1$-C$_6$)alkoxy, —R$^3$(R$^6$)$_q$, —OR$^3$(R$^6$)$_q$, nitro, —NR$^{14}$R$^{15}$, —SO$_2$R$^3$, (C$_1$-C$_6$)alkyl, —C(O)R$^7$, —R$^1$YR$^3$, and —CO(O)R$^2$, wherein any two R$^9$, R$^{10}$ or R$^{11}$ groups can optionally join to form a 3 to 8 membered cycloalkyl, aryl, heterocyclyl or heteroaryl ring, wherein the heterocyclyl or heteroaryl ring may contain one to three heteroatoms selected from —NR$^5$—, —O—, —S—, —S(O)—, or —SO$_2$—, and wherein the cycloalkyl, aryl, heterocyclyl or heteroaryl ring may be optionally substituted by one to three R$^4$ groups;

R$^{12}$ and R$^{13}$ are independently selected from the group consisting of H, (C$_1$-C$_6$)alkyl, (C$_3$-C$_8$)cycloalkyl, (C$_1$-C$_6$)alkoxy, —[C(R$^6$)$_2$]$_r$—, —O[C(R$^6$)$_2$]$_r$—, oxo, halo, —C(O)R$^7$, —NR$^1$R$^2$, and —CO(O)R$^2$, wherein R$^{12}$ and R$^{13}$ can optionally be taken together with the carbon to which they are joined to form a 3 to 8 membered cycloalkyl ring or 4 to 8 membered heterocyclyl ring containing one to three heteroatoms selected from —NR$^5$—, —O—, —S—, —S(O)—, —SO$_2$—, wherein the cycloalkyl ring or heterocyclyl ring may be optionally substituted by one to three R$^{10}$ groups;

R$^{14}$ and R$^{15}$ are independently selected from the group consisting of H, (C$_1$-C$_6$)alkyl, (C$_3$-C$_8$)cycloalkyl, (C$_1$-C$_6$)alkoxy, —R$^3$(R$^6$)$_q$, and —OR$^3$(R$^6$)$_q$, wherein R$^{14}$ and R$^{15}$ may be taken together with the nitrogen to which they are joined to form a 4 to 8 membered heterocyclyl or heteroaryl ring optionally containing one or three heteroatoms from —NR$^5$—, —O—, —S—, —S(O)—, or —SO$_2$—, wherein the heterocyclyl or heteroaryl ring may be optionally substituted by one to three R$^{10}$ groups;

Q is —[C(R$^6$)$_2$]$_r$—;
m and n are independently 0, 1, 2, 3, or 4;
p is independently 0, 1, 2, 3, or 4; and
r and q are independently 0, 1, 2, 3, or 4.

In a further embodiment of the present invention, there is provided a compound of Formula I:

Formula I

[chemical structure of triterpenoid compound with W, X, Y, Z substituents]

or a pharmaceutically acceptable salt thereof, wherein:
W is selected from —CH$_2$— or —C(=O)—;
X is selected from H or C$_1$-C$_6$-alkyl;
Y is selected from —NR$^1$R$^2$ or —OR$^5$;
Z is

[structure: HO—C(O)—C(CH$_3$)$_2$—CH$_2$—C(O)—];

R$^1$ and R$^2$ are each independently selected from the group consisting of H, —(C$_1$-C$_6$)alkyl-OR$^3$, and -(Q)$_n$R$^3$;

R³ is selected from the group consisting of

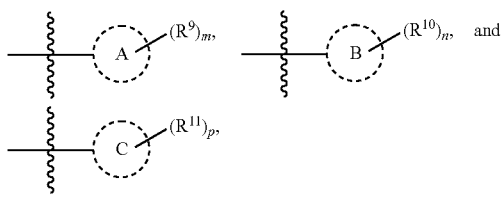

wherein:
A is $(C_5-C_{14})$aryl,
B is selected from $(C_2-C_9)$heterocycle or $(C_2-C_9)$heteroaryl, each having one to three heteroatoms selected from S, N or O, and
C is $(C_3-C_7)$cycloalkyl; R⁵ is H;
R⁶ is independently selected from H or $(C_1-C_6)$alkyl, wherein two R⁶ alkyl groups can optionally be taken together with the carbon to which they are joined to form a 3 to 8 membered cycloalkyl ring, wherein the cycloalkyl ring may be optionally substituted by one to three R¹⁰ groups;
R⁹, R¹⁰, and R¹¹ are independently selected from the group consisting of oxo, halo, $(C_1-C_6)$alkoxy, —R³(R⁶)$_q$, —OR³(R⁶)$_q$, nitro, —NR¹⁴R¹⁵, —SO₂R³, $(C_1-C_6)$alkyl, —C(O)R⁷, —R¹YR³, and —CO(O)R²;
R¹² and R¹³ are independently selected from the group consisting of H, $(C_1-C_6)$alkyl, $(C_3-C_8)$cycloalkyl, $(C_1-C_6)$alkoxy, —[C(R⁶)₂]$_r$—, —O[C(R⁶)₂]$_r$—, oxo, halo, —C(O)R⁷, —NR¹R², and —CO(O)R², wherein R¹² and R¹³ can optionally be taken together with the carbon to which they are joined to form a 3 to 8 membered cycloalkyl ring or 4 to 8 membered heterocyclyl ring containing one to three heteroatoms selected from —NR⁵—, —O—, —S—, —S(O)—, —SO₂—, wherein the cycloalkyl ring or heterocyclyl ring may be optionally substituted by one to three R¹⁰ groups;
R¹⁴ and R¹⁵ are independently selected from the group consisting of H, $(C_1-C_6)$alkyl, $(C_3-C_8)$cycloalkyl, $(C_1-C_6)$alkoxy, —R³(R⁶)$_q$, and —OR³(R⁶)$_q$, wherein R¹⁴ and R¹⁵ may be taken together with the nitrogen to which they are joined to form a 4 to 8 membered heterocyclyl or heteroaryl ring optionally containing one or three heteroatoms from —NR⁵—, —O—, —S—, —S(O)—, or —SO₂—, wherein the heterocyclyl or heteroaryl ring may be optionally substituted by one to three R¹⁰ groups;
Q is —[C(R⁶)₂]$_r$—;
m and n are independently 0, 1, 2, 3, or 4;
p is independently 0, 1, 2, 3, or 4; and
r and q are independently 0, 1, 2, 3, or 4.

In a further embodiment of the present invention, there is provided a composition comprising a) the compound of Formula I or a pharmaceutically acceptable salt thereof; and 2) a pharmaceutically acceptable excipient.

In a further embodiment of the present invention, there is provided a method of treating HIV comprising administering to a patient suffering therefrom an effective amount of the compound of Formula I, or a pharmaceutically acceptable salt thereof.

Such compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formula I, wherein the compound or salt of the compound is used in the manufacture of a medicament for use in the treatment of a viral infection in a human.

In another embodiment of the invention, there is provided a pharmaceutical composition comprising a pharmaceutically acceptable diluent and a therapeutically effective amount of a compound as defined in Formula I.

In one embodiment, the pharmaceutical formulation containing a compound of Formula I or a salt thereof is a formulation adapted for parenteral administration. In another embodiment, the formulation is a long-acting parenteral formulation. In a further embodiment, the formulation is a nanoparticle formulation.

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formula I or salts thereof and the other pharmaceutically active agent(s) and the relative timings of administration will be selected in order to achieve the desired combined therapeutic effect.

As such, the compounds of the present invention may be used in combination with one or more agents useful in the prevention or treatment of HIV.

Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Inteqrase inhibitors such as raltegravir, elvitegravir, GSK1349572, GSK1265744 and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

The scope of combinations of compounds of this invention with HIV agents is not limited to those mentioned above, but includes in principle any combination with any pharmaceutical composition useful for the treatment of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452.

Ritonavir is 10-hydroxy-2-methyl-5-(1-methyethyl)-1-1[2-(1-methylethyl)-4-thiazolyl]-3,6-dioxo-8,11-bis(phenylmethyl)-2,4,7,12-tetraazatridecan-1-oic acid, 5-thiazolylmethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 is a compound being developed by Gilead Sciences of Foster City Calif. as a pharmacological enhancer.

SPI-452 is a compound being developed by Sequoia Pharmaceuticals of Gaithersburg, Md., as a pharmacological enhancer.

In one embodiment of the present invention, a compound of Formula I is used in combination with ritonavir. In one embodiment, the combination is an oral fixed dose combination. In another embodiment, the compound of Formula I is formulated as a long acting parenteral injection and ritonavir is formulated as an oral composition. In one embodiment, is a kit containing the compound of Formula I formulated as a long acting parenteral injection and ritonavir formulated as an oral composition. In another embodiment, the compound of Formula I is formulated as a long acting parenteral injection and ritonavir is formulated as an injectable composition. In one embodiment, is a kit containing the compound of Formula I formulated as a long acting parenteral injection and ritonavir formulated as an injectable composition.

In another embodiment of the present invention, a compound of Formula I is used in combination with GS-9350. In one embodiment, the combination is an oral fixed dose combination. In another embodiment, the compound of Formula I is formulated as a long acting parenteral injection and GS-9350 is formulated as an oral composition. In one embodiment, is a kit containing the compound of Formula I formulated as a long acting parenteral injection and GS-9350 formulated as an oral composition. In another embodiment, the compound of Formula I is formulated as a long acting parenteral injection and GS-9350 is formulated as an injectable composition. In one embodiment, is a kit containing the compound of Formula I formulated as a long acting parenteral injection and GS-9350 formulated as an injectable composition.

In one embodiment of the present invention, a compound of Formula I is used in combination with SPI-452. In one embodiment, the combination is an oral fixed dose combination. In another embodiment, the compound of Formula I is formulated as a long acting parenteral injection and SPI-452 is formulated as an oral composition. In one embodiment, is a kit containing the compound of Formula I formulated as a long acting parenteral injection and SPI-452 formulated as an oral composition. In another embodiment, the compound of Formula I is formulated as a long acting parenteral injection and SPI-452 is formulated as an injectable composition. In one embodiment, is a kit containing the compound of Formula I formulated as a long acting parenteral injection and SPI-452 formulated as an injectable composition.

The above other therapeutic agents, when employed in combination with the chemical entities described herein, may be used, for example, in those amounts indicated in the Physicians' Desk Reference (PDR) or as otherwise determined by one of ordinary skill in the art.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I, wherein said virus is an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I, further comprising administration of a therapeutically effective amount of one or more agents active against an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I, further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In further embodiments, the compound of the present invention, or a pharmaceutically acceptable salt thereof, is chosen from the compounds set forth in Table 1.

TABLE 1

| Example No. | Parent Structure | Chemical Name |
|---|---|---|
| 1 | | 4-(((3aS,5aR,5bR,7aR,9S,11aR,11bR,13aS)-3a-((E)-3-((1-(4-Chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 2 | | 4-(((3aS,5aR,5bR,7aR,9S,11aR,11bR,13aS)-3a-((E)-3-((4-Chlorophenyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 3 | | 4-(((3aS,5aR,5bR,7aR,9S,11aR,11bR,13aS)-3a-((E)-3-(((S)-1-(5-Chloropyridin-2-yl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 4 | | 4-(((3aS,5aR,5bR,7aR,9S,11aR,11bR,13aS)-3a-((E)-3-(((R)-1-(4-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Example No. | Parent Structure | Chemical Name |
|---|---|---|
| 5 | | 4-(((3aS,5aR,5bR,7aR,9S,11aR,11bR,13aS)-3a-((E)-3-(((R)-1-(5-Chloropyridin-2-yl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 6 | | 4-(((3aS,5aR,5bR,7aR,9S,11aR,11bR,13aS)-3a-((E)-3-(((S)-1-(4-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 7 | | 4-(((3aS,5aR,5bR,7aR,9S,11aR,11bR,13aS)-3a-((E)-3-((1-(5-Chloropyridin-2-yl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 8 | | 4-(((3aS,5aR,5bR,7aR,9S,11aR,11bR,13aS)-1-Isopropyl-5a,5b,8,8,11a-pentamethyl-2-oxo-3a-((E)-3-oxo-3-(((S)-1-(pyrimidin-4-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Example No. | Parent Structure | Chemical Name |
|---|---|---|
| 9 | | 4-(((3aS,5aR,5bR,7aR,9S,11aR,11bR,13aS)-1-Isopropyl-5a,5b,8,8,11a-pentamethyl-2-oxo-3a-((E)-3-oxo-3-(((R)-1-(pyrimidin-4-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 10 | | 4-(((3aS,5aR,5bR,7aR,9S,11aR,11bR,13aS)-1-Isopropyl-5a,5b,8,8,11a-pentamethyl-2-oxo-3a-((E)-3-oxo-3-(((R)-1-(pyrimidin-4-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 11 | | 4-(((3aS,5aR,5bR,7aR,9S,11aR,11bR,13aS)-1-isopropyl-5a,5b,8,8,11a-pentamethyl-2-oxo-3a-((E)-3-oxo-3-(((S)-1-(pyrimidin-4-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 12 | | 4-(((3aS,5aR,5bR,7aR,9S,11aR,11bR,13aS)-1-Isopropyl-5a,5b,8,8,11a-pentamethyl-2-oxo-3a-((E)-3-oxo-3-((1-(pyridin-2-yl)cyclopropyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Example No. | Parent Structure | Chemical Name |
|---|---|---|
| 13 | 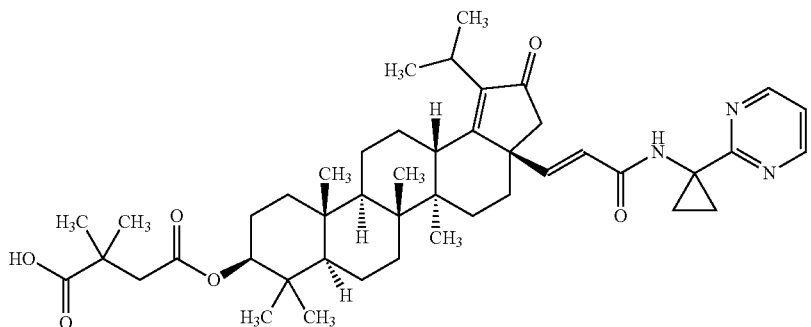 | 4-(((3aS,5aR,5bR,7aR,9S,11aR,11bR,13aS)-1-isopropyl-5a,5b,8,8,11a-pentamethyl-2-oxo-3a-((E)-3-oxo-3-((1-(pyrimidin-2-yl)cyclopropyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 14 | 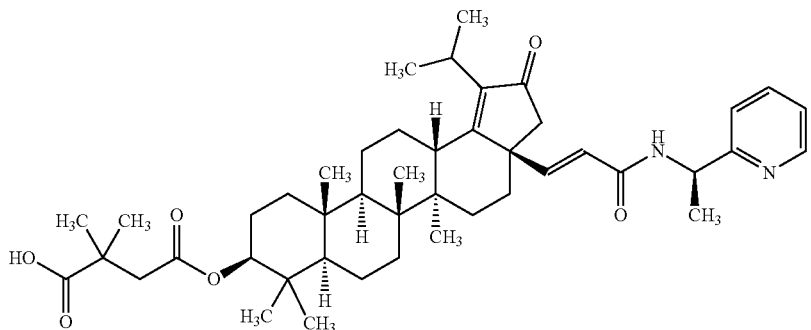 | 4-(((3aS,5aR,5bR,7aR,9S,11aR,11bR,13aS)-1-Isopropyl-5a,5b,8,8,11a-pentamethyl-2-oxo-3a-((E)-3-oxo-3-(((R)-1-(pyridin-2-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 15 | 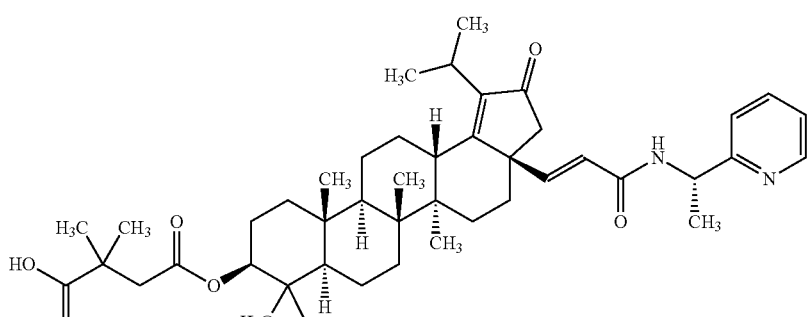 | 4-(((3aS,5aR,5bR,7aR,9S,11aR,11bR,13aS)-1-Isopropyl-5a,5b,8,8,11a-pentamethyl-2-oxo-3a-((E)-3-oxo-3-(((S)-1-(pyridin-2-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 16 | 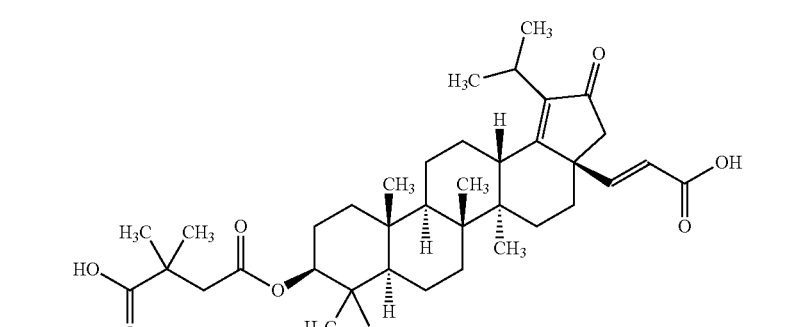 | 4-(((3aS,5aR,5bR,7aR,9S,11aR,11bR,13aS)-3a-((E)-2-Carboxyvinyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Example No. | Parent Structure | Chemical Name |
|---|---|---|
| 17 | | 4-(((3aS,5aR,5bR,7aR,9S,11aR,11bR,13aS)-3a-((E)-3-((4-Fluorophenyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 18 | | 4-(((3aS,5aR,5bR,7aR,9S,11aR,11bR,13aS)-3a-((E)-3-((5-Chloropyridin-2-yl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 19 | | 4-(((3aS,5aR,5bR,7aR,9S,11aR,11bR,13aS)-3a-((E)-3-((5-Chloropyridin-2-yl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 20 | | 4-(((3aS,5aR,5bR,7aR,9S,11aR,11bR,13aS)-3a-((E)-3-((1-(2-Chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Example No. | Parent Structure | Chemical Name |
|---|---|---|
| 21 | | 4-(((3aS,5aR,5bR,7aR,9S,11aR,11bR,13aS)-1-Isopropyl-5a,5b,8,8,11a-pentamethyl-2-oxo-3a-((E)-3-oxo-3-(p-tolylamino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 22 | | 4(((3aS,5aR,5bR,7aR,9S,11aR,11bR,13aS)-3a-((E)-3-(((R)-1-(2-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 23 | | 4-(((3aS,5aR,5bR,7aR,9S,11aR,11bR,13aS)-3a-((E)-3-(((S)-1-(3-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 24 | | 4-(((3aS,5aR,5bR,7aR,9S,11aR,11bR,13aS)-3a-((E)-3-((1-(3-Chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Example No. | Parent Structure | Chemical Name |
|---|---|---|
| 25 | | 4-(((3aS,5aR,5bR,7aR,9S,11aR,11bR,13aS)-3a-((E)-3-(((S)-1-(2-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 26 | | 4-(((3aS,5aR,5bR,7aR,9S,11aR,11bR,13aS)-3a-((E)-3-((1-(5-Chloropyrimidin-2-yl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 27 | | 4-(((3aS,5aR,5bR,7aR,9S,11aR,11bR,13aS)-3a-((E)-3-((1-(4-Chlorophenyl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 28 | | 4-(((3aS,5aR,5bR,7aR,9S,11aR,11bR,13aS)-3a-((E)-3-((1-(5-Chloropyrimidin-2-yl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Example No. | Parent Structure | Chemical Name |
|---|---|---|
| 29 | | 4-(((3aS,5aR,5bR,7aR,9S,11aR,11bR,13aS)-3a-((E)-3-((1-(3-Chlorophenyl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 30 | | 4-(((3aS,5aR,5bR,7aR,9S,11aR,11bR,13aS)-3a-((E)-3-(Cyclohexylamino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 31 | | 4-(((3aS,5aR,5bR,7aR,9S,11aR,11bR,13aS)-3a-((E)-3-(((R)-1-(3-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 32 | | 4-(((3aS,5aR,5bR,7aR,9S,11aR,11bR,13aS)-3a-((E)-3-((2-Hydroxyethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Example No. | Parent Structure | Chemical Name |
|---|---|---|
| 33 | 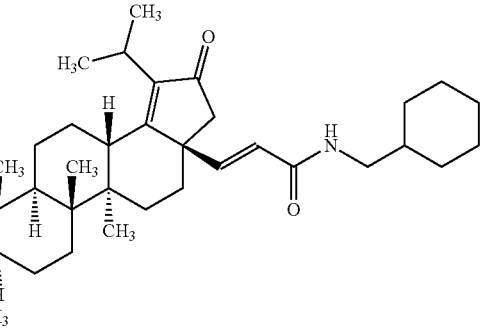 | 4(((3aS,5aR,5bR,7aR,9S,11aR,11bR,13aS)-3a-((E)-3-((Cyclohexylmethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 34 | 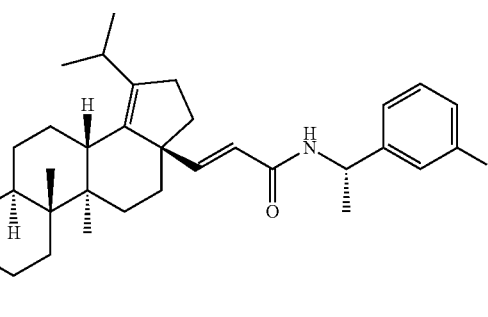 | 4-(((3aS,5aR,5bR,7aR,9S,11aR,11bR,13aS)-3a-((E)-3-(((S)-1-(3-Chlorophenyl)ethyl)amino)-3-oxoprop-1-en-1-yl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

The compounds of Table 1 were synthesized according to the Synthetic Methods, General Schemes, and the Examples described below.

In certain embodiments, the compound(s) of the present invention, or a pharmaceutically acceptable salt thereof, is chosen from the compounds set forth in Table 1.

Synthetic Methods

The methods of synthesis for the provided chemical entities employ readily available starting materials using the following general methods and procedures. It will be appreciated that where typical or preferred process conditions (i.e., reaction temperatures times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Ernka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Unless specified to the contrary, the reactions described herein take place at atmospheric pressure, generally within a temperature range from −78° C. to 200° C. Further, except as employed in the Examples or as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLES

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

aq.=aqueous
μL=microliters
μM=micromolar
NMR=nuclear magnetic resonance
boc=tert-butoxycarbonyl
br=broad
Cbz=benzyloxycarbonyl
d=doublet
δ=chemical shift
° C.=degrees celcius
DCM=dichloromethane
dd=doublet of doublets
DMEM=Dulbeco's Modified Eagle's Medium
DMF=N,N-dimethylformamide
DMSO=dimethylsulfoxide
EtOAc=ethyl acetate
g=gram
h or hr=hours
HCV=hepatitis C virus
HPLC=high performance liquid chromatography
Hz=hertz
IU=International Units
$IC_{50}$=inhibitory concentration at 50% inhibition
J=coupling constant (given in Hz unless otherwise indicated)
m=multiplet
M=molar
$M+H^+$=parent mass spectrum peak plus $H^+$
mg=milligram
min=minutes
mL=milliliter
mM=millimolar
mmol=millimole
MS=mass spectrum
nm=nanomolar
ppm=parts per million
q.s.=sufficient amount
s=singlet
RT=room temperature
sat.=saturated
t=triplet
TFA=trifluoroacetic acid Equipment Description $^1$H NMR spectra were recorded on a Bruker Avance-III 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Agilent 1200 HPLC/6110 or Agilent 1200 HPLC/6130 using a SunFire C18, 4.6×50 mm, 3.5 μm using a gradient elution method.

Solvent A: 0.01% trifluoroacetic acid (TFA) in water;
Solvent B: 0.01% TFA in acetonitrile;
Constant A for 1.2 min followed by 5%-95% or 20%-95% B over 4 min.

Schemes and Experimental Procedures

The following schemes and procedures illustrate how compounds of the present invention can be prepared. The specific solvents and reaction conditions referred to are also illustrative and are not intended to be limiting. Compounds not described are either commercially available or are readily prepared by one skilled in the art using available starting materials. The Examples disclosed herein are for illustrative purposes only and are not intended to limit the scope of the invention. All examples exhibited LHIV $IC_{50}$ values between 1 μM and 1 nM using the assay disclosed herein.

Synthesis of the Aldehyde Intermediate 6

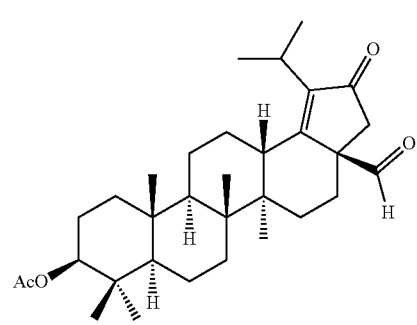

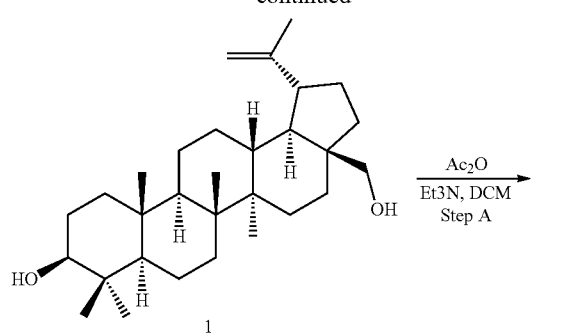

1

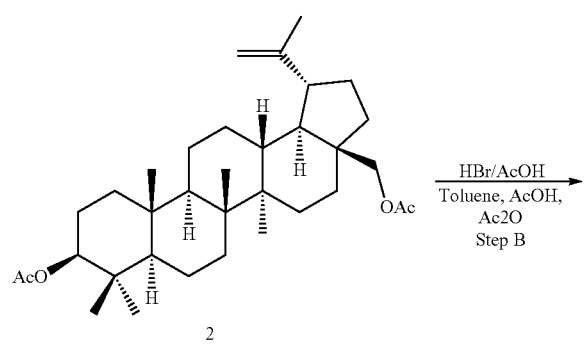

2

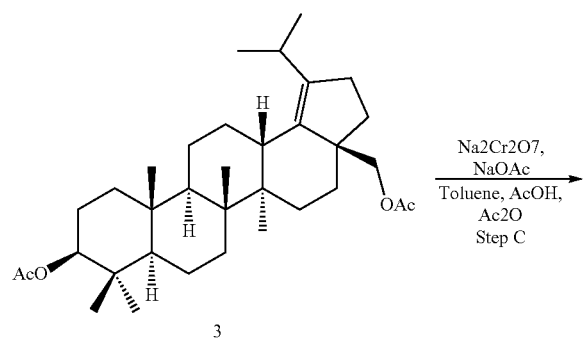

3

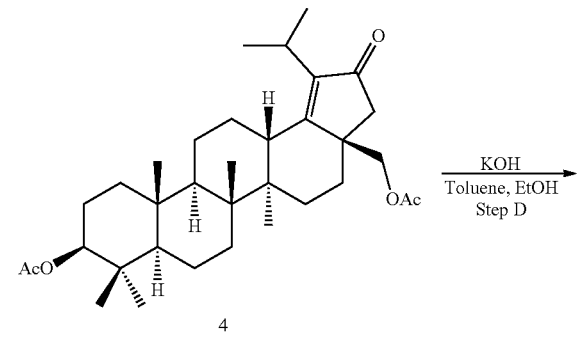

4

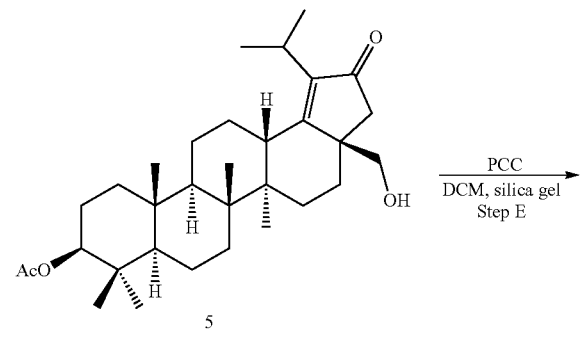

5

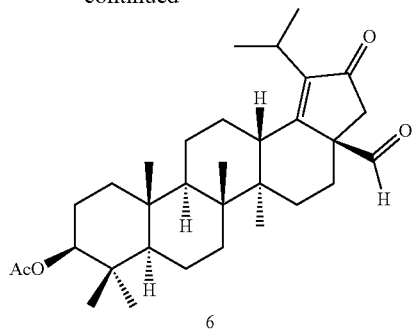

6

Step A

Intermediate 2

((1R,3aS,5aR,5bR,7aR,9S,11aR,11bR,13aR,13bR)-9-Acetoxy-5a,5b,8,8,11a-pentamethyl-1-(prop-1-en-2-yl)icosahydro-1H-cyclopenta[a]chrysen-3a-yl) methyl acetate To a solution of the intermediate 1 (20 g, 45.2 mmol), 4-dimethylaminopyridine (DMAP, 1.66 g, 13.6 mmol), and $Et_3N$ (63 mL, 136 mmol) in $CH_2Cl_2$ (DCM, 100 mL) at room temperature was added acetic anhydride ($Ac_2O$, 17.1 mL, 113 mmol). After it was heated at reflux overnight, and cooled down to room temperature, the reaction was quenched with water (50 mL). The organic phase was then washed with water (50 mL×2) and dried over sodium sulfate. After removing most of the organic solvent under reduced pressure, anhydrous ethanol (50 mL) was added and the resulting precipitates were collected by filtration as a white solid (Intermediate 2, 20 g, 84%). $^1$H NMR (400 MHz, $CDCl_3$) δ ppm 4.69 (1H, m), 4.59 (1H, m), 4.51-4.43 (1H, m), 4.25 (1H, d, J=11.2 Hz), 3.85 (1H, d, J=10.8 Hz), 2.49-2.40 (1H, m), 2.07 (3H, s), 2.04 (3H, s), 1.98-0.77 (42H, m).

LC/MS: m/z calculated 526.4. Found 527.7 (M+1)+.

Step B

Intermediate 3

((3aS,5aR,5bR,7aR,9S,11aR,11bR,13aS)-9-Acetoxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-3a-yl)methyl acetate HBr in acetic acid (40 mL, 33%) was added to a suspension of the intermediate 2 (20 g, 38 mmol) in toluene (40 mL), $Ac_2O$ (40 mL), and acetic acid (AcOH, 40 mL) previously heated at 105° C. The reaction mixture was stirred and heated at this temperature for 1.5 h. After cooling down, sodium acetate (24 g) was added and the resulting reaction mixture was evaporated to dryness. The pale brownish residue was taken up in DCM (200 mL) and the organic phase was washed with water (100 mL×3), dried over sodium sulfate, and evaporated to dryness under reduced pressure to provide a residue, which was recrystallized from ethanol (EtOH, 95%) and DCM to afford the intermediate 3 (13.8 g, 69%) as a white solid. $^1$H NMR (400 MHz, $CDCl_3$) δ ppm 4.50-4.46 (1H, m), 4.02 (1H, d, J=10.8 Hz), 3.98 (1H, d, J=10.8 Hz), 3.18-3.10 (1H, m), 2.43-2.40 (1H, m), 2.26-2.22 (2H, m), 2.04 (3H, s), 2.05 (3H, s), 2.00-1.95 (1H, m), 1.90-1.85 (1H, m), 1.77-0.83 (39H, m). LC/MS: m/z calculated 526.4. Found 549.2 (M+Na)+.

Step C

Intermediate 4

((3aR,5aR,5bR,7aR,9S,11aR,11bR,13aS)-9-Acetoxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl) methyl acetate A mixture of the intermediate 3 (7 g, 13.29 mmol), sodium acetate (NaOAc, 6.21 g, 76 mmol) and sodium dichromate dihydrate (4.75 g, 15.95 mmol) in anhydrous toluene (90 mL), AcOH (119 mL), and Ac$_2$O (29 mL) was stirred at 60° C. overnight. After cooling down, the reaction mixture was partitioned between water (150 mL) and ethyl acetate (EtOAc, 250 mL). The organic phase was washed successively with water (100 mL), saturated solution of sodium carbonate (100 mL×2) and brine (100 mL×2), dried over sodium sulfate, and concentrated under reduced pressure to afford a sticky oil. The sticky oil was triturated with MeOH (250 mL) and the precipitates were collected to give the intermediate 4 (6 g, 11.1 mmol, 83%) as a white solid. $^1$H NMR (400 MHz, CDCl$_3$) δ ppm 4.52-4.46 (1H, m), 4.33 (1H, d, J=10.8 Hz), 4.06 (1H, d, J=11.2 Hz), 3.21-3.16 (1H, m), 2.86 (1H, dd, J=12.8, 3.2 Hz), 2.42-2.36 (1H, m), 2.05 (3H, s), 2.00 (3H, s), 1.94-0.84 (40H, m). LC/MS: m/z calculated 540.4. Found 563.3 (M+Na)+.

Step D

Intermediate 5

(3aR,5aR,5bR,7aR,9S,11aR,11bR,13aS)-3a-(Hydroxymethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate A mixture of the intermediate 4 (7 g, 12.94 mmol) and potassium hydroxide (KOH, 0.872 g, 15.5 mmol) in EtOH (200 mL) and toluene (200 mL) was stirred vigorously at room temperature for 1 h. The reaction mixture was neutralized with aqueous HCl (1N) to pH 7 and evaporated to dryness. The obtained residue was taken up in water and a small amount of acetone. The precipitates were collected and then washed with water and dried in vacuo to obtain the intermediate 5 (6.0 g, 93%) as a white solid. LC/MS: m/z calculated 498.4. Found 499.3 (M+1)+.

Step E

Intermediate 6

(3aR,5aR,5bR,7aR,9S,11aR,11bR,13aS)-3a-Formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate To a solution of the intermediate 5 (5.1 g, 10.23 mmol) in DCM (300 mL) at room temperature were added pyridinium chlorochromate (PCC, 6.61 g, 30.7 mmol), and silica gel (6.6 g). The reaction mixture was stirred at room temperature for 1 h. After the reaction was quenched with water, the organic phase was washed with saturated sodium bicarbonate solution (100 mL), dried over sodium sulfate, and evaporated under reduced pressure to provide a crude product, which was purified by column chromatography on silica gel (EtOAc: PE=1:10 to 1:5) to provide the intermediate 6 (4.2 g, 83%) as a white solid.

LC/MS: m/z calculated 496.4. Found 497.2 (M+1)+.

Example 1

4-(((3aS,5aR,5bR,7aR,9S,11aR,11bR,13aS)-3a-((E)-3-((1-(4-Chlorophenyl)cyclopropyl)amino)-3-oxo-prop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

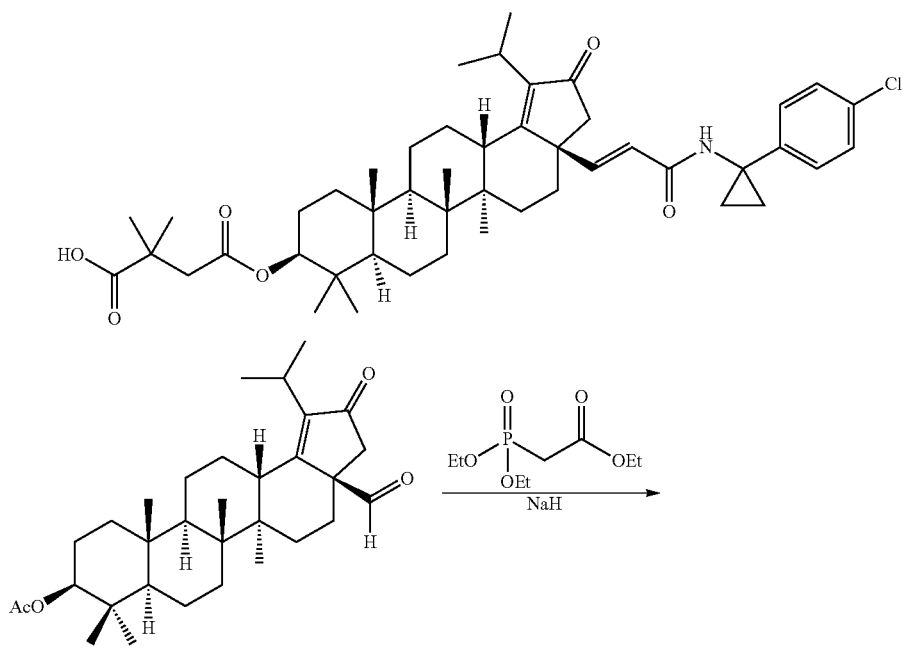

-continued
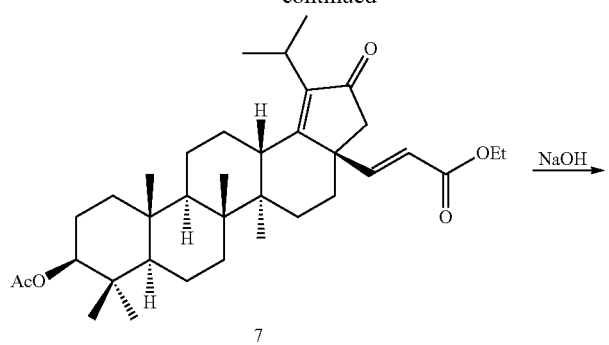
7
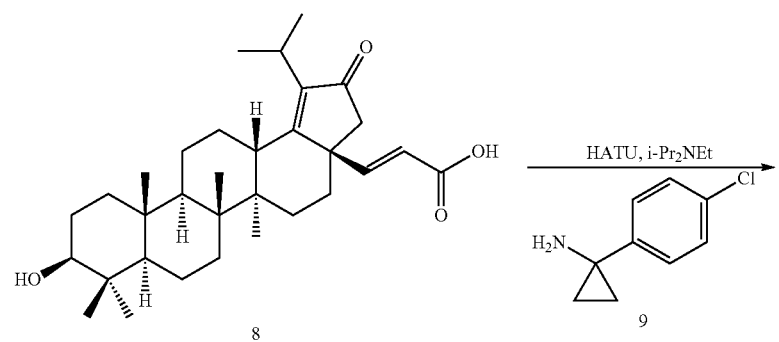
8  9
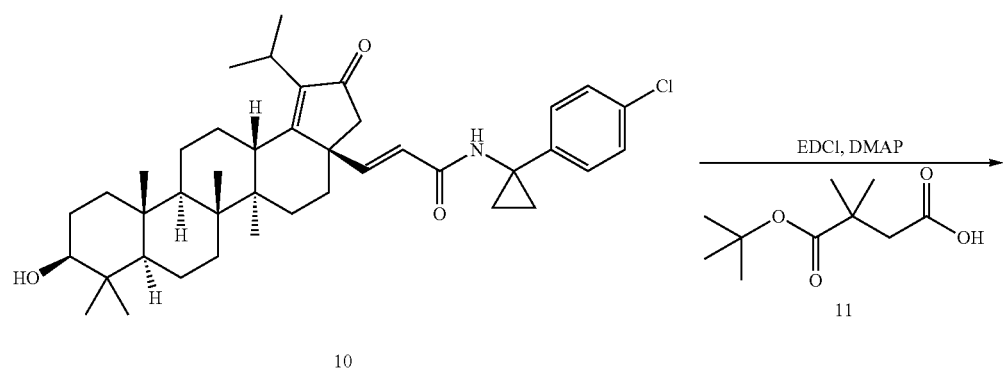
10  11
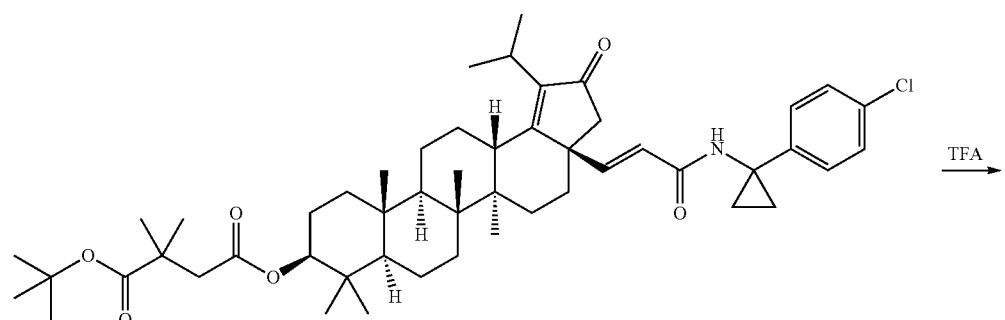
12

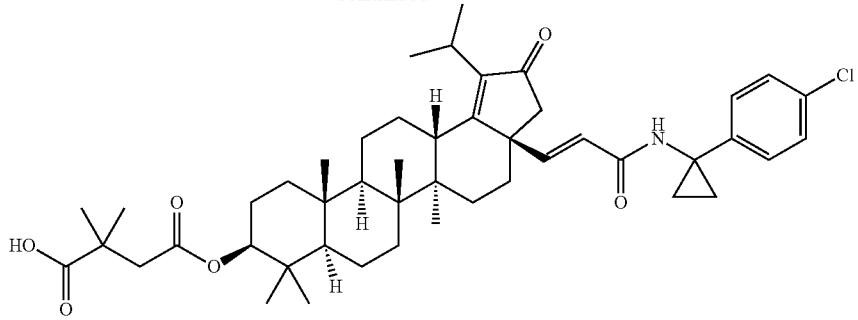

13

Step A

Intermediate 7

(E)-Ethyl 3-((3aS,5aR,5bR,7aR,9S,11aR,11bR,13aS)-9-acetoxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)acrylate To a suspension of ethyl 2-(diethoxyphosphoryl)acetate (1.173 g, 5.23 mmol) in N,N-Dimethylformamide (DMF) (10 mL) stirred under nitrogen at 0° C. was added NaH (0.242 g, 8.05 mmol) dropwise during 5 min and stirred for 10 mins the solution was warmed to r.t. and stirred at for 30 mins before the solution of (3b)-21,28-dioxolup-18-en-3-yl acetate (2 g, 4.03 mmol) Tetrahydrofuran (THF) (5 mL) was added to above mixture, monitored by LCMS. After 4 hs, the reaction was quenched by saturated $NaHCO_3$ and is extracted with DCM. The combined organic phase was dried over sodium sulphate and evaporated in vacuo, and recrystallized from iethyl ether to give (E)-ethyl 3-((3aS,5aR,5bR,7aR,9S,11aR,11bR,13aS)-9-acetoxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)acrylate (1.8 g, 3.13 mmol, 78%) as a yellow solid.

Step B

Intermediate 8

(E)-3-((3aS,5aR,5bR,7aR,9S,11aR,11bR,13aS)-9-Hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)acrylic acid To a solution of (E)-ethyl 3-((3aS,5aR,5bR,7aR,9S,11aR,11bR,13aS)-9-acetoxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)acrylate (1.6 g, 2.82 mmol) in tetrahydrofuran (THF) (15 mL), methanol (10 mL) and water (5 mL) was added sodium hydroxide (4.52 g, 113 mmol). The reaction mixture was stirred at 20° C. for 4 hs. The reaction mixture was evaporated to dryness and adjusted pH to 5 by saturated $NH_4Cl$. The solid is solved into DCM (50 mL), washed with water, dried over Na2SO4 and concentrated to yield the (E)-3-((3aS,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)acrylic acid (1.2 g, 2.012 mmol, 71.3%) as a yellow solid.

Step C

Intermediate 10

(E)-N-(1-(4-Chlorophenyl)cyclopropyl)-3-((3aS,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)acrylamide To a solution of (E)-3-((3aS,5aR,5bR,7aR,9S,1aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)acrylic acid (500 mg, 1.007 mmol), 1-(4-chlorophenyl)cyclopropanamine hydrochloride (226 mg, 1.107 mmol) and HATU (765 mg, 2.013 mmol) in N,N-dimethylformamide (DMF) (2 mL) stirred at 0° C. was added DIPEA (0.703 mL, 4.03 mmol). The reaction mixture was stirred at 20° C. for 1 h. The reaction mixture was adjusted pH to 3-4 by 2 M HCl, filtered, and the solid was washed with water (50 mL), solved into DCM, dried over sodium sulfate and evaporated in vacuo to give the crude product. The crude product was washed with petrol ether/EtOAc/DCM (10/1/1) to afford the target product (E)-N-(1-(4-chlorophenyl)cyclopropyl)-3-((3aS,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)acrylamide (685 mg, 1.007 mmol, 100%)) as a yellow solid.

Step D

Intermediate 12

1-Tert-butyl 4-((3aS,5aR,5bR,7aR,9S,11aR,11bR,13aS)-3a-((E)-3-((1-(4-chlorophenyl)cyclopropyl)amino)-3-oxoprop-1-en-1-yl)-1-isopropyl-5a,5b,8,8,1a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate To a solution of DMAP (647 mg, 5.30 mmol), EDC (1016 mg, 5.30 mmol) and 4-tert-butoxy-3,3-dimethyl-4-oxobutanoic acid (663 mg, 3.18 mmol) (11) in Dichloromethane (10 mL) stirred at 20° C. for 30 min was added (E)-N-(1-(4-chlorophenyl)cyclopropyl)-3-((3aS,5aR,5bR,7aR,9S,11aR, 11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl) acrylamide (685 mg, 1.060 mmol). The reaction mixture was stirred at 20° C. for 2 h. The mixture was washed with saturated ammonium chloride, water, and saturated NaHCO₃, water, and brine. The organic layer was dried over Na₂SO₄, filtered and concentrated to give the crude product, which was purified by silica gel column eluting with Petrol ether/Ethyl acetate (5:1) to afford the product 1-tert-butyl 4-((3aS,5aR,5bR,7aR,9S,11aR,11bR,13aS)-3a-((E)-3-((1-(4-chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (480 mg, 0.542 mmol, 51.2%) as a light yellow solid.

Step E

Compound 13

4-(((3aS,5aR,5bR,7aR,9S,11aR,11bR,13aS)-3a-((E)-3-((1-(4-Chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid To a solution of 1-tert-butyl 4-((3aS,5aR,5bR,7aR,9S,11aR,11bR,13aS)-3a-((E)-3-((1-(4-chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (460 mg, 0.554 mmol) in Dichloromethane (6 mL) was added TFA (3 mL, 0.554 mmol). The reaction mixture was stirred at r.t for 2 hs and evaporated in vacuo to afford crude product, which was purified by preparative-HPLC (Mobile Phase: A=0.05% TFA/H₂O, B=MeCN) to give the product 4-(((3aS,5aR,5bR,7aR,9S,11aR,11bR,13aS)-3a-((E)-3-((1-(4-chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (130 mg, 0.162 mmol, 29.2%) as a white solid. ¹H NMR (400 MHz, CDCl₃) δ ppm 9.00 (m, 1H), 7.31 (d, J=8.8 Hz, 2H), 7.15 (d, J=15.6 Hz, 1H), 7.06 (d, J=8.8 Hz, 2H), 5.99 (d, J=15.6 Hz, 1H), 4.56 (m, 1H), 3.11 (m, 1H), 2.89-0.80 (m, 54H); LC/MS: m/z calculated 773.4. Found 774.3 (M+1)⁺.

The intermediate 11 used above was prepared according to the following procedure.

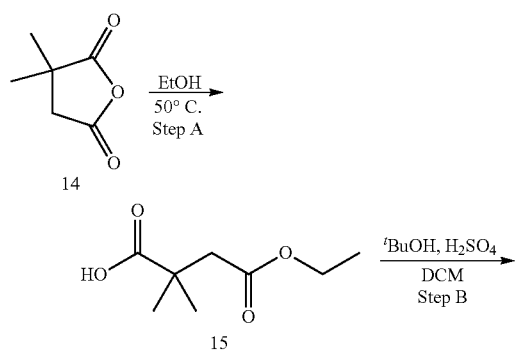

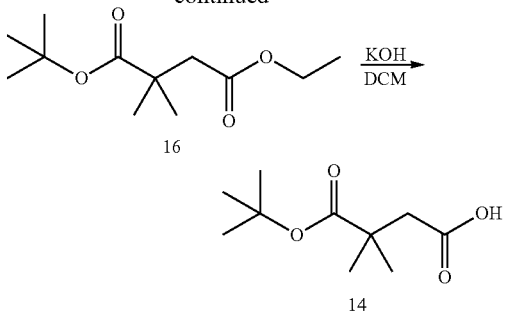

Step A

Intermediate 15

4-Ethoxy-2,2-dimethyl-4-oxobutanoic acid

A solution of 3,3-dimethyl-dihydrofuran-2,5-dione 14 (25 g, 195 mmol) in anhydrous EtOH (150 mL) was stirred at 50° C. overnight. After cooling down to room temperature, the solvent was removed under reduced pressure with a rotary evaporator and the residue was triturated with hexane at −50° C. to afford the intermediate 15 (25 g, 133 mmol, 67.9%) as a white solid. ¹H NMR (400 MHz, CDCl₃) δ ppm 4.13-4.18 (2H, q, J=7.2 Hz), 2.62 (2H, s), 1.28 (6H, s), 1.32-1.25 (3H, t, J=7.6 Hz). LC/MS: m/z calculated 174.1. Found 173.1 (M−1)−.

Step B

Intermediate 16

1-Tert-butyl 4-ethyl 2,2-dimethylsuccinate

To a mixture of the intermediate 15 (20 g, 109 mmol), magnesium sulfate (52.5 g, 436 mmol), and tert-butanol (60 mL) in DCM (480 mL) was added sulfuric acid (8.72 mL, 164 mmol). After stirring at room temperature overnight, the reaction mixture was poured into saturated sodium bicarbonate solution (300 mL) and water (300 mL). DCM was added to extract the desired product, and the organic phase was washed with brine, dried, and concentrated to afford the intermediate 16 (19 g, 83 mmol, 80%) as a colorless oil. ¹H NMR (400 MHz, CDCl₃) δ ppm 4.02-4.08 (2H, q, J=7.2 Hz), 2.46 (2H, s), 1.07 (9H, s), 1.14-1.20 (9H, m). LC/MS: m/z calculated 230.2. Found 253.1 (M+Na)+.

Step C

Intermediate 11

4-(Tert-butoxy)-3,3-dimethyl-4-oxobutanoic acid

To a solution of the intermediate 15 (10 g, 41.3 mmol) in EtOH (200 mL) was added potassium hydroxide (12.86 g, 206 mmol) in water (100 mL) at room temperature. The reaction mixture was stirred at room temperature for 2 h. The pH of the reaction mixture was adjusted to 3-4 by 1N HCl. The resulting solution was extracted with ether (300 mL), and the ether phase was dried and concentrated to afford a crude product, which was recrystallized from hexane at −10° C. to afford the intermediate 11 (4 g, 19.78 mmol, 47.9%) as a white solid. $^1$H NMR (400 MHz, CDCl$_3$) δ ppm 2.58 (2H, s), 1.43 (9H, s), 1.25 (6H, s).

LC/MS: m/z calculated 202.1. Found 201.1 (M−1)$^−$.

Example 2

4-(((3aS,5aR,5bR,7aR,9S,11aR,11bR,13aS)-3a-((E)-3-((4-Chlorophenyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

17

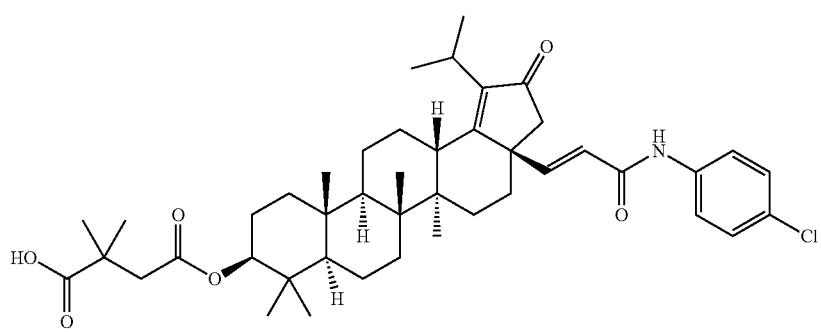

To a solution of 1-tert-butyl 4-((3aS,5aR,5bR,7aR,9S,11aR,11bR,13aS)-3a-((E)-3-((4-chlorophenyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (230 mg, 0.291 mmol) in Dichloromethane (DCM) (4 mL) was added TFA (2 mL, 0.291 mmol). The reaction mixture was stirred at r.t for 2 hs and evaporated in vacuo to afford crude product, which was purified by preparative-HPLC (Mobile Phase: A=0.05% TFA/H2O, B=MeCN) to give the product 4-(((3aS,5aR,5bR,7aR,9S,11aR,11bR,13aS)-3a-((E)-3-((4-chlorophenyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (100 mg, 0.136 mmol, 46.8%) as a white solid. $^1$H NMR (400 MHz, CDCl$_3$) δ ppm 7.60-7.53 (m, 3H), 7.28 (d, J=8.4 Hz, 2H), 7.12 (d, J=15.6 Hz, 1H), 5.84 (d, J=15.6 Hz, 1H), 4.50 (dd, J=11.2, 5.2 Hz, 1H), 3.22 (m, 1H), 2.77 (d, J=11.6 Hz, 1H), 2.68 (d, J=16.0 Hz, 1H), 2.57 (d, J=15.6 Hz, 1H), 2.32 (d, J=18.8 Hz, 1H), 2.20 (d, J=19.2 Hz, 1H), 2.11 (d, J=12.0 Hz, 1H), 1.93-0.77 (m, 44H); LC/MS: m/z calculated 733.4. Found 734.3 (M+1)$^+$.

Example 3

4-(((3aS,5aR,5bR,7aR,9S,11aR,11bR,13aS)-3a-((E)-3-(((S)-1-(5-Chloropyridin-2-yl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

18

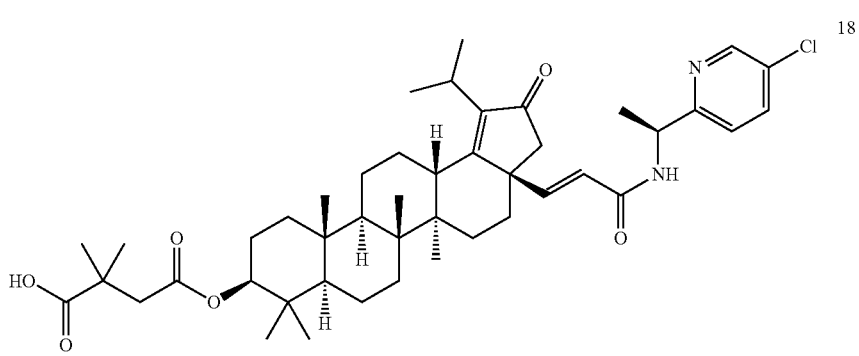

To a solution of 1-tert-butyl 4-((3aS,5aR,5bR,7aR,9S,11aR,11bR,13aS)-3a-((E)-3-(((S)-1-(5-chloropyridin-2-yl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (240 mg, 0.293 mmol), 2,2,2-trifluoroacetic acid (1 mL, 12.98 mmol) in Dichloromethane (4 mL) stirred at rt. The reaction mixture was stirred at rt for 2 h. The reaction mixture was evaporated and then purified by preparative-HPLC (Mobile Phase A: Water (0.05% TFA), B: ACN; Gradient 85-85% B in 0-12 min, stop at 12 min; Flow Rate (ml/min) 30.00) to give the product 4-(((3aS,5aR,5bR,7aR,9S,11aR,11bR,13aS)-3a-((E)-3-(((S)-1-(5-chloropyridin-2-yl)ethyl)amino)-3-oxoprop-1-en-1-yl)-1-isopropyl-5a,5b,8,8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl)oxy)-2,2-dimethyl-4-oxobutanoic acid, Trifluoroacetic acid salt (80 mg, 0.091 mmol, 31.0%) as a white solid. $^1$H NMR (400 MHz, CHLOROFORM-d) δ=8.56 (br. s., 1H), 8.13-7.82 (m, 3H), 7.65 (d, J=7.3 Hz, 1H), 7.45 (d, J=8.5 Hz, 1H), 6.87 (d, J=15.8 Hz, 1H), 5.80 (d, J=15.8 Hz, 1H), 5.28 (m, 1H), 4.51 (dd, J=4.8, 11.0 Hz, 1H), 3.20 (m, 1H), 2.78-2.56 (m, 3H), 2.36-2.05 (m, 3H), 2.02-0.64 (m, 48H); LC/MS: m/z calculated 762.4. Found 763.3 (M+1)$^+$.

Example 4

4-(((3aS,5aR,5bR,7aR,9S,11aR,11bR,13aS)-3a-((E)-3-(((R)-1-(4-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

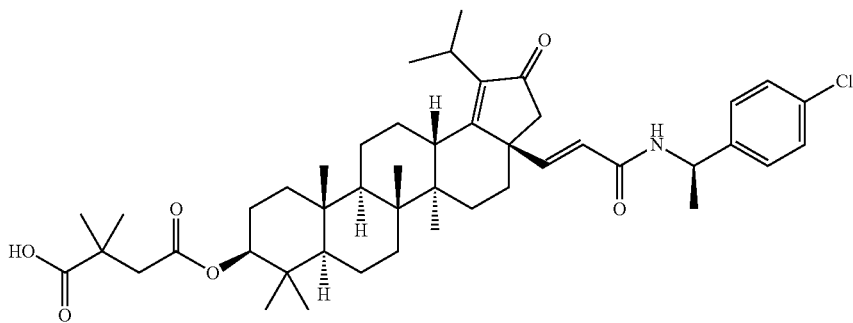

19

To a solution of 1-tert-butyl 4-((3aS,5aR,5bR,7aR,9S,11aR,11bR,13aS)-3a-((E)-3-(((R)-1-(4-chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (2.5 g, 3.05 mmol) in Dichloromethane (20 mL) was added TFA (13 mL, 3.05 mmol). The reaction mixture was stirred at r.t. for 2 hs and evaporated in vacuo to afford crude product, which was diluted with DCM, washed with water, saturated NaHCO$_3$ twice, water, 2 M HCl, water, and the organic layer was concentrated, diluted with MeOH/H2O (1:5, 36 mL) and freeze-dried under high vacuo to give the product 4-(((3aS,5aR,5bR,7aR,9S,11aR,11bR,13aS)-3a-((E)-3-(((R)-1-(4-chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (1.7 g, 2.217 mmol, 72.6%) as a yellow solid. $^1$H NMR (400 MHz, DMSO-d$_6$) d=12.34-12.04 (m, 1H), 8.43 (d, J=7.8 Hz, 1H), 7.53-7.18 (m, 4H), 6.63 (d, J=15.8 Hz, 1H), 5.92 (d, J=15.8 Hz, 1H), 4.94 (quin, J=7.0 Hz, 1H), 4.39 (dd, J=4.6, 10.9 Hz, 1H), 3.18 (dt, J=6.7, 13.7 Hz, 1H), 2.70 (dd, J=4.3, 10.5 Hz, 2H), 2.58-2.52 (m, 1H), 2.34-1.99 (m, 3H), 1.99-0.56 (m, 48H); LC/MS: m/z calculated 761.4. Found 762.3 (M+1)$^+$.

Example 5

4-(((3aS,5aR,5bR,7aR,9S,11aR,11bR,13aS)-3a-((E)-3-(((R)-1-(5-Chloropyridin-2-yl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

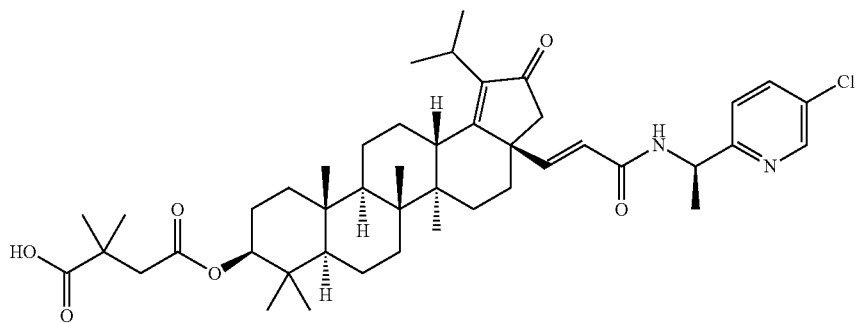

20

To a solution of 1-tert-butyl 4-((3aS,5aR,5bR,7aR,9S,11aR,11bR,13aS)-3a-((E)-3-(((R)-1-(5-chloropyridin-2-yl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (150 mg, 0.183 mmol), 2,2,2-trifluoroacetic acid (1 mL, 12.98 mmol) in dichloromethane (4 mL) stirred at rt. The reaction mixture was stirred at rt for 2 h. The reaction mixture was evaporated and then purified by preparative-HPLC (Mobile Phase A: Water (0.05% TFA), B: ACN; Gradient 85-85% B in 0-12 min, stop at 12 min; Flow Rate (ml/min) 30.00) to give the product 4-(((3aS,5aR,5bR,7aR,9S,11aR,11bR,13aS)-3a-((E)-3-(((R)-1-(5-chloropyridin-2-yl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid, Trifluoroacetic acid salt (80 mg, 0.091 mmol, 49.8%) as a white solid. $^1$H NMR (400 MHz, CHLOROFORM-d) δ=8.58 (d, J=1.8 Hz, 1H), 7.84 (dd, J=1.8, 8.0 Hz, 1H), 7.58-7.40 (m, 2H), 6.89 (d, J=15.8 Hz, 1H), 5.79 (d, J=15.8 Hz, 1H), 5.26 (m, 1H), 4.52 (dd, J=5.3, 11.0 Hz, 1H), 3.31-3.13 (m, 1H), 2.84-2.47 (m, 3H), 2.38-2.02 (m, 3H), 2.04-0.63 (m, 47H); LC/MS: m/z calculated 762.4. Found 763.3 (M+1)$^+$.

Example 6

4-(((3aS,5aR,5bR,7aR,9S,11aR,11bR,13aS)-3a-((E)-3-(((S)-1-(4-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

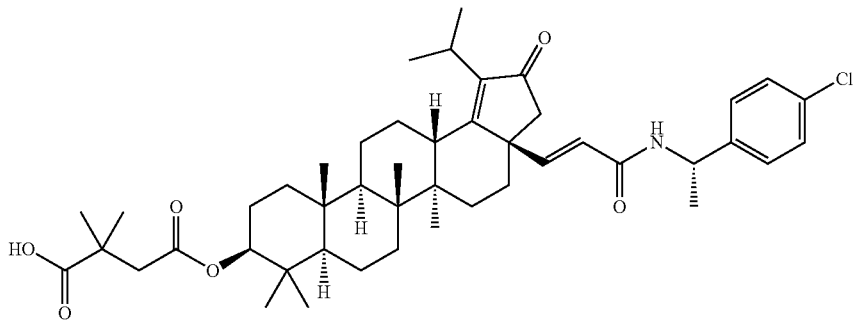

21

To a solution of 1-tert-butyl 4-((3aS,5aR,5bR,7aR,9S,11aR,11bR,13aS)-3a-((E)-3-(((S)-1-(4-chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (420 mg, 0.513 mmol) in Dichloromethane (6 mL) was added TFA (3 mL, 0.513 mmol). The reaction mixture was stirred at r.t for 2 hs and evaporated in vacuo to afford crude product, which was purified by preparative-HPLC (Mobile Phase: A=0.05% TFA/H$_2$O, B=MeCN) to give the product 4-(((3aS,5aR,5bR,7aR,9S,11aR,11bR,13aS)-3a-((E)-3-(((S)-1-(4-chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (60 mg, 0.079 mmol, 15.34%) as a white solid. $^1$H NMR (400 MHz, CHLOROFORM-d) δ=7.44-7.18 (m, 4H), 6.97 (d, J=15.8 Hz, 1H), 5.80-5.58 (m, 2H), 5.25-5.09 (m, 1H), 4.50 (dd, J=5.3, 10.8 Hz, 1H), 3.27-3.13 (m, 1H), 2.79-2.52 (m, 2H), 2.36-2.01 (m, 3H), 2.00-0.65 (m, 47H); LC/MS: m/z calculated 761.4. Found 762.3 (M+1)$^+$.

Example 7

4-(((3aS,5aR,5bR,7aR,9S,11aR,11bR,13aS)-3a-((E)-3-((1-(5-Chloropyridin-2-yl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

22

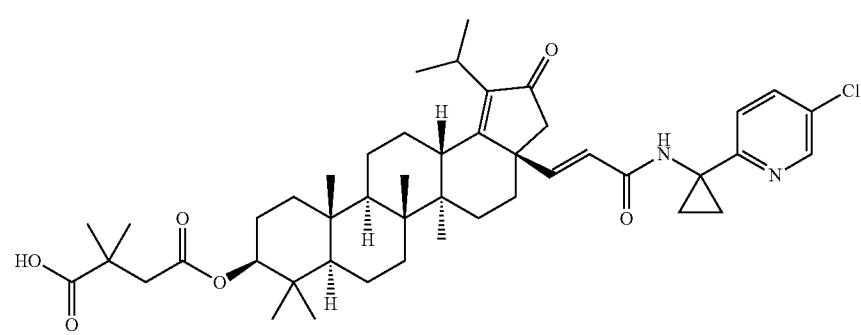

To a solution of 1-tert-butyl 4-((3aS,5aR,5bR,7aR,9S,11aR,11bR,13aS)-3a-((E)-3-((1-(5-chloropyridin-2-yl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (300 mg, 0.361 mmol) in Dichloromethane (6 mL) was added TFA (3 mL, 0.361 mmol). The reaction mixture was stirred at r.t for 2 hs and evaporated in vacuo to afford crude product, which was purified by preparative-HPLC (Mobile Phase: A=0.05% TFA/H₂O, B=MeCN) to give the product 4-(((3aS,5aR,5bR,7aR,9S,11aR,11bR,13aS)-3a-((E)-3-((1-(5-chloropyridin-2-yl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid, trifluoroacetic acid salt (120 mg, 0.135 mmol, 37.4%) as a white solid. $^1$H NMR (300 MHz, DMSO-$d_6$) δ=8.62 (m, 1H), 8.43 (d, J=2.3 Hz, 1H), 7.75 (dd, J=2.0, 8.4 Hz, 1H), 7.27 (d, J=8.5 Hz, 1H), 6.73 (d, J=15.8 Hz, 1H), 5.96 (d, J=16.0 Hz, 1H), 4.43 (dd, J=5.9, 10.0 Hz, 1H), 3.20 (m, 1H), 2.81 (m, 1H), 2.52 (m, 1H), 2.27-0.72 (m, 52H); LC/MS: m/z calculated 774.4. Found 775.3 (M+1)$^+$.

Example 8

4-(((3aS,5aR,5bR,7aR,9S,11aR,11bR,13aS)-1-Isopropyl-5a,5b,8,8,11a-pentamethyl-2-oxo-3a-((E)-3-oxo-3-(((S)-1-(pyrimidin-4-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid 2-oxo-3a-((E)-3-oxo-3-(((S)-1-(pyrimidin-4-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl) 2,2-dimethylsuccinate (100 mg, 0.127 mmol) in dichloromethane (8 mL) stirred at room temp was added TFA (4 mL, 28.7 mmol). The reaction mixture was stirred at 20° C. for 1 h. The product was extracted with DCM (15 mL*3), the residue was purified by preparative-HPLC to provide the TFA salt of the title compound (70 mg, 98%) as a white solid. $^1$H NMR (400 MHz, CHLOROFORM-d) δ=9.24 (s, 1H), 8.80 (br. s., 1H), 7.45 (d, J=4.5 Hz, 1H), 7.08-6.86 (m, 2H), 5.82 (d, J=15.6 Hz, 1H), 5.26 (m, 1H), 4.53 (dd, J=5.0, 11.0 Hz, 1H), 3.23 (m, 1H), 2.85-2.52 (m, 3H), 2.42-2.05 (m, 3H), 2.06-0.70 (m, 47H); LC/MS: m/z calculated 729.5. Found 730.4 (M+1)$^+$.

Example 9

4-(((3aS,5aR,5bR,7aR,9S,11aR,11bR,13aS)-1-Isopropyl-5a,5b,8,8,11a-pentamethyl-2-oxo-3a-((E)-3-oxo-3-(((R)-1-(pyrimidin-4-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

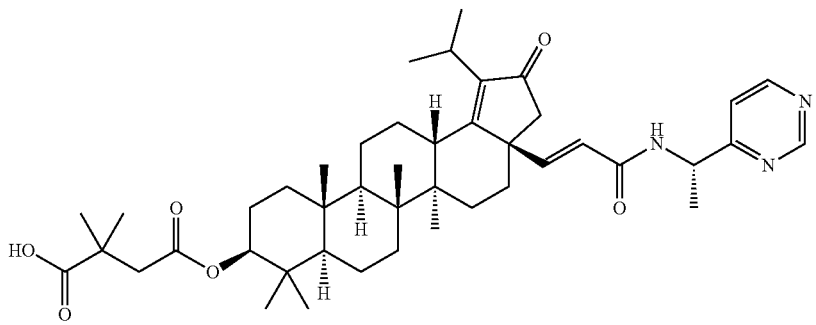

23

To a solution of 1-tert-butyl 4-((3aS,5aR,5bR,7aR,9S,11aR,11bR,13aS)-1-isopropyl-5a,5b,8,8,11a-pentamethyl-

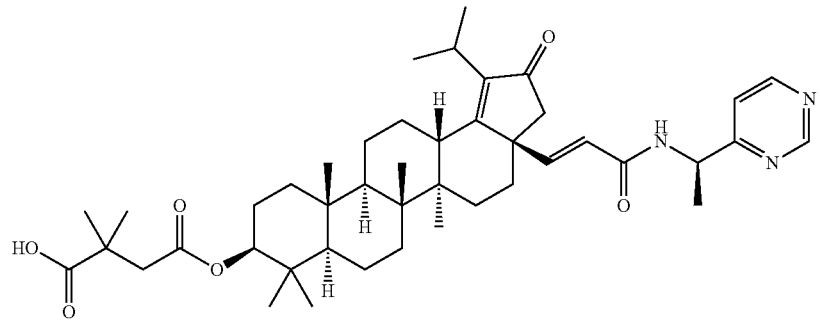

24

To a solution of 1-tert-butyl 4-((3aS,5aR,5bR,7aR,9S,11aR,11bR,13aS)-1-isopropyl-5a,5b,8,8,11a-pentamethyl-2-oxo-3a-((E)-3-oxo-3-(((R)-1-(pyrimidin-4-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl) 2,2-dimethylsuccinate (100 mg, 0.127 mmol) in dichloromethane (8 mL) stirred at room temp was added TFA (4 mL, 28.7 mmol). The reaction mixture was stirred at 20° C. for 1 h. The product was extracted with DCM (15 mL*3), the residue was purified by preparative-HPLC to provide the TFA salt of the title compound (70 mg, 98%) as a white solid. $^1$H NMR (400 MHz, CHLOROFORM-d) δ=9.24 (s, 1H), 8.78 (br. s., 1H), 7.43 (d, J=4.3 Hz, 1H), 7.08-6.82 (m, 2H), 5.81 (d, J=15.8 Hz, 1H), 5.26 (m, 1H), 4.52 (dd, J=5.0, 11.0 Hz, 1H), 3.36-3.16 (m, 1H), 2.83-2.51 (m, 3H), 2.41-2.06 (m, 3H), 2.05-0.71 (m, 47H); LC/MS: m/z calculated 729.5. Found 730.4 (M+1)$^+$.

yl) 2,2-dimethylsuccinate (130 mg, 0.127 mmol) in dichloromethane (8 mL) stirred at room temp was added TFA (4 ml, 51.9 mmol). The reaction mixture was stirred at 20° C. for 3 h. The product was extracted with DCM (15 mL*2), the combined organic phase was washed with brine (15 mL), dried, removed solvents and the residue was purified by preparative-HPLC to provide the TFA salkt of the title compound (78 mg, 72%) as a white solid. $^1$H NMR (400 MHz, CHLOROFORM-d) δ=8.78 (d, J=4.8 Hz, 2H), 7.34-7.28 (m, 1H), 7.13-7.05 (m, 1H), 6.96 (d, J=15.8 Hz, 1H), 5.82 (d, J=15.8 Hz, 1H), 5.44-5.28 (m, 1H), 4.51 (dd, J=5.0, 11.0 Hz, 1H), 3.30-3.13 (m, 1H), 2.83-2.50 (m, 3H), 2.40-2.05 (m, 3H), 2.03-0.68 (m, 46H); LC/MS: m/z calculated 729.5. Found 730.4 (M+1)+.

Example 10

4-(((3aS,5aR,5bR,7aR,9S,11aR,11bR,13aS)-1-Isopropyl-5a,5b,8,8,11a-pentamethyl-2-oxo-3a-((E)-3-oxo-3-(((R)-1-(pyrimidin-2-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid Example 11

4-(((3aS,5aR,5bR,7aR,9S,11aR,11bR,13aS)-1-isopropyl-5a,5b,8,8,11a-pentamethyl-2-oxo-3a-((E)-3-oxo-3-(((S)-1-(pyrimidin-2-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

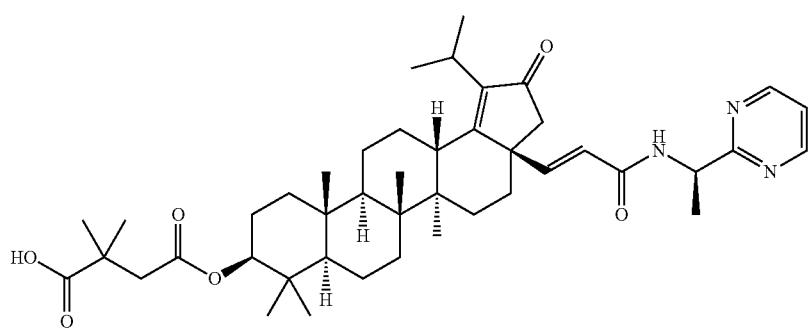

To a solution of 1-tert-butyl 4-((3aS,5aR,5bR,7aR,9S,11aR,11bR,13aS)-1-isopropyl-5a,5b,8,8,11a-pentamethyl-2-oxo-3a-((E)-3-oxo-3-(((R)-1-(pyrimidin-2-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-

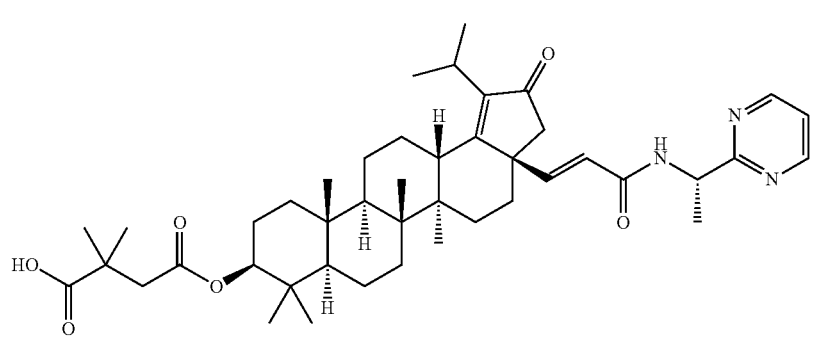

To a solution of 1-tert-butyl 4-((3aS,5aR,5bR,7aR,9S,11aR,11bR,13aS)-1-isopropyl-5a,5b,8,8,11a-pentamethyl-2-oxo-3a-((E)-3-oxo-3-(((S)-1-(pyrimidin-2-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl) 2,2-dimethylsuccinate (120 mg, 0.128 mmol) in dichloromethane (8 mL) stirred at room temp was added TFA (4 mL, 51.9 mmol). The reaction mixture was stirred at 25° C. for 2 h. The product was extracted with DCM (15 mL*3), the combined organic phase was washed with brine (20 mL), dried, removed the solvent and the residue was purified by preparative-HPLC to provide the TFA salt of the title compound (70 mg, 65%) as a white solid. $^1$H NMR (400 MHz, CHLOROFORM-d) δ=8.79 (d, J=4.5 Hz, 2H), 7.37-7.28 (m, 1H), 7.11 (br. s., 1H), 6.95 (d, J=15.6 Hz, 1H), 5.84 (d, J=15.8 Hz, 1H), 5.43-5.25 (m, 1H), 4.50 (dd, J=5.0, 10.5 Hz, 1H), 3.31-3.09 (m, 1H), 2.82-2.50 (m, 3H), 2.39-2.05 (m, 3H), 2.01-0.70 (m, 46H); LC/MS: m/z calculated 729.5. Found 730.4 (M+1)$^+$.

Example 12

4-(((3aS,5aR,5bR,7aR,9S,11aR,11bR,13aS)-1-Isopropyl-5a,5b,8,8,11a-pentamethyl-2-oxo-3a-((E)-3-oxo-3-((1-(pyridin-2-yl)cyclopropyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid yl) 2,2-dimethylsuccinate (460 mg, 0.577 mmol) in dichloromethane (6 mL) was added TFA (3 mL, 0.577 mmol). The reaction mixture was stirred at r.t for 2 hr and evaporated in vacuo to afford crude product, which was purified by preparative-HPLC (Mobile Phase: A=0.05% TFA/H$_2$O, B=MeCN) to give the title compound, trifluoroacetic acid salt (30 mg, 0.033 mmol, 5.78%) as a white solid. $^1$H NMR (400 MHz, DMSO-d$_6$) δ=12.16 (br. s., 1H), 8.80 (s, 1H), 8.42 (d, J=4.0 Hz, 1H), 7.66 (t, J=7.4 Hz, 1H), 7.29-7.06 (m, 2H), 6.69 (d, J=15.8 Hz, 1H), 5.97 (d, J=15.8 Hz, 1H), 4.40 (dd, J=4.6, 10.9 Hz, 1H), 3.27-3.13 (m, 1H), 3.02-2.87 (m, 1H), 2.80 (d, J=11.5 Hz, 1H), 2.59-2.52 (m, 1H), 2.30-0.73 (m, 51H); LC/MS: m/z calculated 740.5. Found 741.3 (M+1)$^+$.

Example 13

4-(((3aS,5aR,5bR,7aR,9S,11aR,11bR,13aS)-1-isopropyl-5a,5b,8,8,11a-pentamethyl-2-oxo-3a-((E)-3-oxo-3-((1-(pyrimidin-2-yl)cyclopropyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

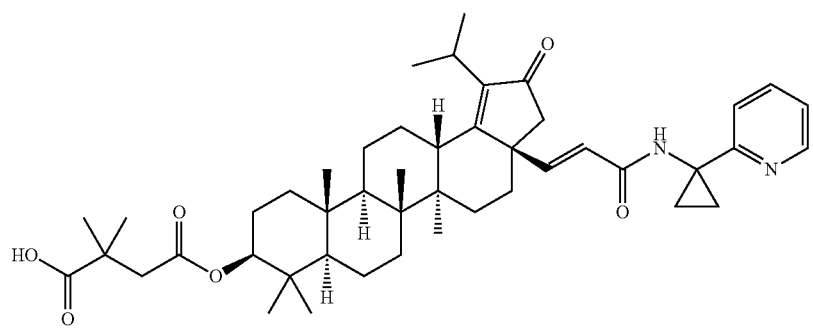

27

To a solution of 1-tert-butyl 4-((3aS,5aR,5bR,7aR,9S,11aR,11bR,13aS)-1-isopropyl-5a,5b,8,8,11a-pentamethyl-2-oxo-3a-((E)-3-oxo-3-((1-(pyridin-2-yl)cyclopropyl)amino)prop-1-en-1-yl)-3,3a,4,5,5a,5b,6,7,7a,8,9,10,11,11a,11b,12,13,13a-octadecahydro-2H-cyclopenta[a]chrysen-9-

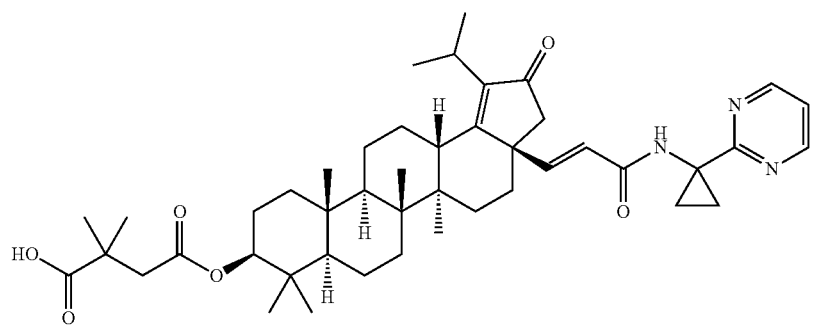

28

To a solution of 1-tert-butyl 4-((3aS,5aR,5bR,7aR,9S, 11aR,11bR,13aS)-1-isopropyl-5a,5b,8,8,11a-pentamethyl-2-oxo-3a-((E)-3-oxo-3-((1-(pyrimidin-2-yl)cyclopropyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl) 2,2-dimethylsuccinate (460 mg, 0.576 mmol) in dichloromethane (6 mL) was added TFA (3 mL, 0.576 mmol). The reaction mixture was stirred at r.t for 2 hs and evaporated in vacuo to afford crude product, which was purified by preparative-HPLC (Mobile Phase: A=0.05% TFA/H$_2$O, B=MeCN) to give the title compound, trifluoroacetic acid salt (100 mg, 0.116 mmol, 20.19%) as a white solid. $^1$H NMR (400 MHz, DMSO-d$_6$) δ=12.18 (br. s., 1H), 8.78-8.57 (m, 3H), 7.39-7.15 (m, 1H), 6.68 (d, J=16.1 Hz, 1H), 5.94 (d, J=16.1 Hz, 1H), 4.40 (dd, J=4.6, 11.2 Hz, 1H), 3.30-3.11 (m, 1H), 2.90-2.67 (m, 1H), 2.59-2.52 (m, 1H), 2.28-2.01 (m, 3H), 2.01-0.75 (m, 49H); LC/MS: m/z calculated 741.5. Found 742.4 (M+1)$^+$.

Example 14

4-(((3aS,5aR,5bR,7aR,9S,11aR,11bR,13aS)-1-Isopropyl-5a,5b,8,8,11a-pentamethyl-2-oxo-3a-((E)-3-oxo-3-(((R)-1-(pyridin-2-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

29

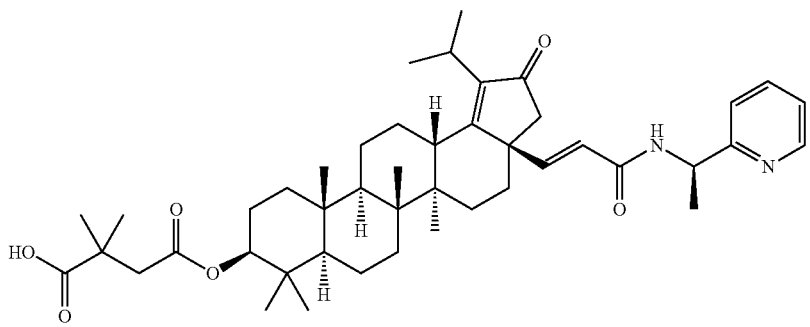

To a solution of 1-tert-butyl 4-((3aS,5aR,5bR,7aR,9S, 11aR,11bR,13aS)-1-isopropyl-5a,5b,8,8,11a-pentamethyl-2-oxo-3a-((E)-3-oxo-3-(((R)-1-(pyridin-2-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl) 2,2-dimethylsuccinate (470 mg, 0.599 mmol) in dichloromethane (10 mL) stirred at rt was added TFA (5 mL). The reaction mixture was stirred at rt for 2 h. Then, it was evaporated in vacuo to get crude product. This material was purified by preparative-HPLC to provide the title compound trifluoroacetic acid salt (225 mg, 0.267 mmol, 44.6%) as a light yellow solid. $^1$H NMR (400 MHz, CHLOROFORM-d) δ=9.23 (d, J=6.8 Hz, 1H), 8.75 (d, J=3.5 Hz, 1H), 8.32 (t, J=7.7 Hz, 1H), 7.92 (d, J=7.8 Hz, 1H), 7.84-7.69 (m, 1H), 6.77 (d, J=15.8 Hz, 1H), 5.89 (d, J=15.8 Hz, 1H), 5.49-5.21 (m, 1H), 4.50 (dd, J=5.4, 10.7 Hz, 1H), 3.32-3.05 (m, 1H), 2.78-2.49 (m, 3H), 2.33-2.01 (m, 3H), 2.03-0.63 (m, 47H); LC/MS: m/z calculated 728.5. Found 729.4 (M+1)$^+$.

Example 15

4-(((3aS,5aR,5bR,7aR,9S,11aR,11bR,13aS)-1-Isopropyl-5a,5b,8,8,11a-pentamethyl-2-oxo-3a-((E)-3-oxo-3-(((S)-1-(pyridin-2-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

30

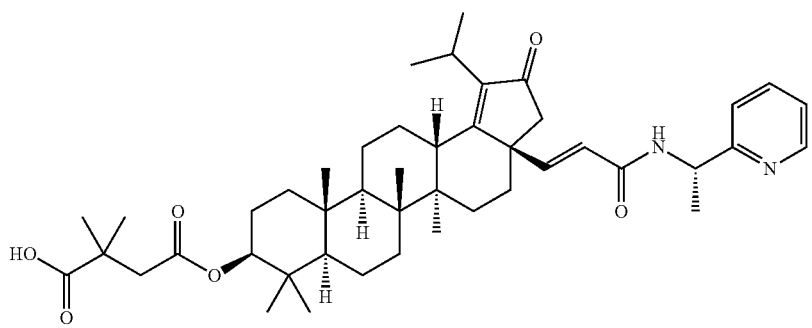

To a solution of 1-tert-butyl 4-((3aS,5aR,5bR,7aR,9S,11aR,11bR,13aS)-1-isopropyl-5a,5b,8,8,11a-pentamethyl-2-oxo-3a-((E)-3-oxo-3-(((S)-1-(pyridin-2-yl)ethyl)amino)prop-1-en-1-yl)-3,3a,4,5,5a,5b,6,7,7a,8,9,10,11,11a,11b,12,13,13a-octadecahydro-2H-cyclopenta[a]chrysen-9-yl) 2,2-dimethylsuccinate (480 mg, 0.611 mmol) in dichloromethane (10 mL) stirred at rt was added TFA (5 mLl). The reaction mixture was stirred at rt for 2 h. Then, it was evaporated in vacuo to get crude product. This material was purified by preparative-HPLC to provide the title compound as a trifluoroacetic acid salt (220 mg, 0.261 mmol, 42.7%) as a light yellow solid. $^1$H NMR (400 MHz, CHLOROFORM-d) δ=9.43 (d, J=7.0 Hz, 1H), 8.75 (d, J=4.5 Hz, 1H), 8.33 (t, J=7.7 Hz, 1H), 7.94 (d, J=7.8 Hz, 1H), 7.77 (t, J=6.4 Hz, 1H), 6.77 (d, J=15.8 Hz, 1H), 5.89 (d, J=15.8 Hz, 1H), 5.50-5.27 (m, 1H), 4.50 (dd, J=5.3, 10.8 Hz, 1H), 3.29-3.05 (m, 1H), 2.76-2.44 (m, 3H), 2.31-2.00 (m, 3H), 2.03-0.51 (m, 47H); LC/MS: m/z calculated 728.5. Found 729.3 (M+1)$^+$.

Example 16

4-(((3aS,5aR,5bR,7aR,9S,11aR,11bR,13aS)-3a-((E)-2-Carboxyvinyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

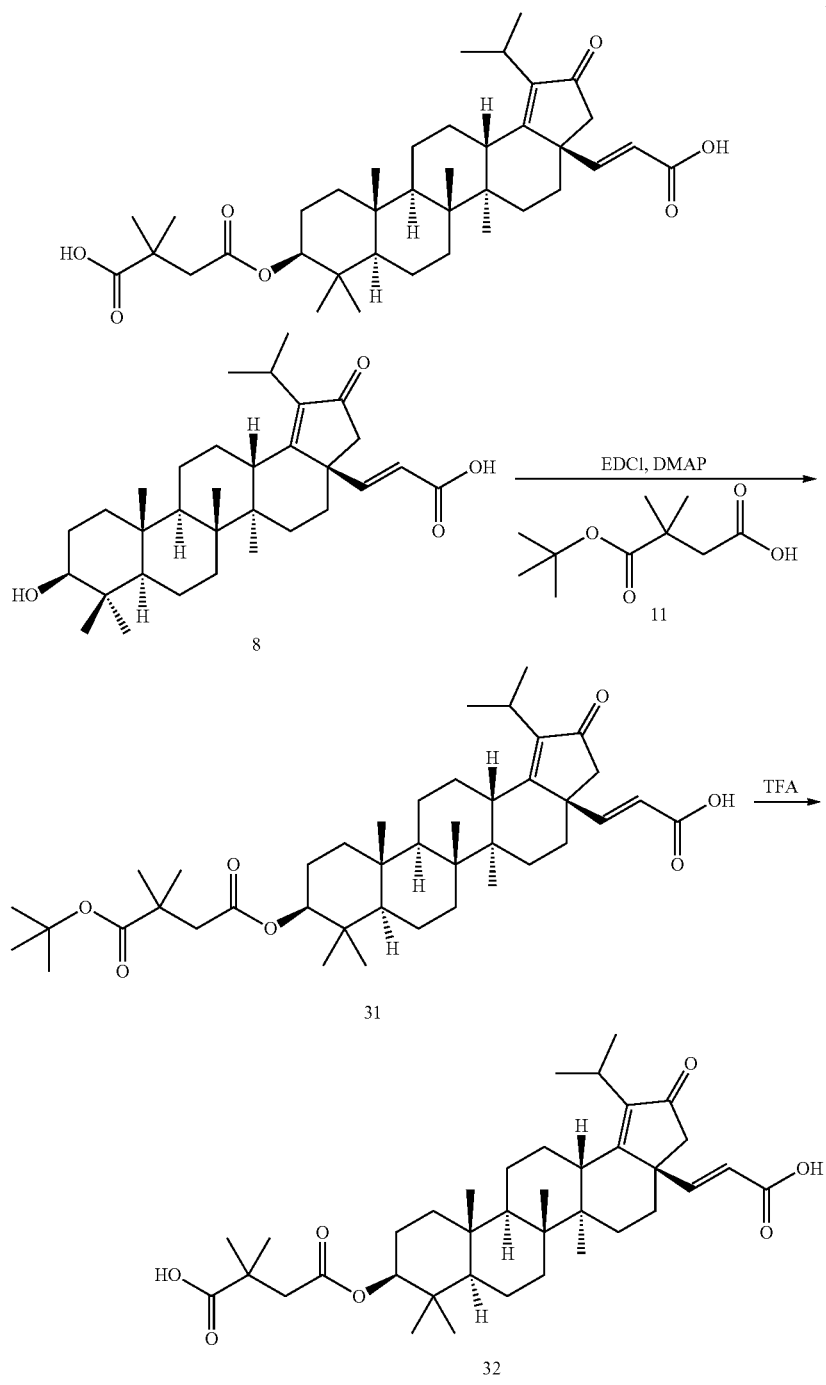

Step A

Intermediate 31

(E)-3-((3aS,5aR,5bR,7aR,9S,11aR,11bR,13aS)-9-((4-(Tert-butoxy)-3,3-dimethyl-4-oxobutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl) acrylic acid To a solution of 4-(tert-butoxy)-3,3-dimethyl-4-oxobutanoic acid (122 mg, 0.604 mmol), DMAP (123 mg, 1.007 mmol) and EDC (193 mg, 1.007 mmol) in dichloromethane (12 mL) stirred at room temp for 30 min was added (E)-3-((3aS,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)acrylic acid (100 mg, 0.201 mmol). The reaction mixture was stirred at 25° C. for 3 h. The produce was extracted with DCM (15 mL*3), the combined organic phase was washed with brine (20 mL), dried, and the solvent removed under reduced pressure to give 110 mg of residue as light yellow solid which was used in the next reaction without further purification.

Step B

Compound 32

4-(((3aS,5aR,5bR,7aR,9S,11aR,11bR,13aS)-3a-((E)-2-Carboxyvinyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid To a solution of (E)-3-((3aS,5aR,5bR,7aR,9S,11aR,11bR,13aS)-9-((4-(tert-butoxy)-3,3-dimethyl-4-oxobutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)acrylic acid (200 mg, 0.294 mmol) in dichloromethane (6 mL) stirred at room temp was added trifluoroacetic acid (TFA) (3 mL). The reaction mixture was stirred at 20° C. for 1 h. The product was extracted with DCM (15 mL*3) and the residue was purified by pre-parative-HPLC to give the title compound (85 mg, 39%) as a white solid. $^1$H NMR (400 MHz, CHLOROFORM-d) δ=7.05 (d, J=16.1 Hz, 1H), 5.75 (d, J=16.3 Hz, 1H), 4.52 (dd, J=4.8, 11.3 Hz, 1H), 3.32-3.11 (m, 1H), 2.78-2.61 (m, 3H), 2.34-2.12 (m, 3H), 2.06-0.61 (m, 44H); LC/MS: m/z calculated 624.4. Found 625.3 (M+1)$^+$.

Example 17

4-(((3aS,5aR,5bR,7aR,9S,11aR,11bR,13aS)-3a-((E)-3-((4-Fluorophenyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

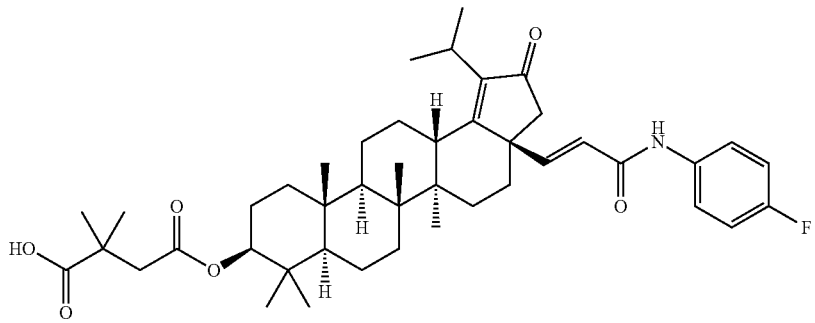

33

To a solution of 1-tert-butyl 4-((3aS,5aR,5bR,7aR,9S,11aR,11bR,13aS)-3a-((E)-3-((4-fluorophenyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (250 mg, 0.323 mmol), TFA (1 mL, 12.98 mmol) in dichloromethane (4 mL) stirred at rt. The reaction mixture was stirred at rt for 2 h, washed with saturated NaHCO$_3$ in water (300 mL×8); followed by 2 M HCl (300 mL), water, and then brine. The organic layer was dried over Na$_2$SO$_4$, filtered and concentrated to give the crude product, which was solved into DCM (80 mL) and hexane (120 mL) was added. The suspension was filtered, washed with hexane to afford the crude product, and then purified by preparative-HPLC to afford the title compound (160 mg, 68%) as a light white solid. $^1$H NMR (400 MHz, CHLOROFORM-d) δ=7.56 (br. s., 3H), 7.23-6.93 (m, 3H), 5.96-5.75 (m, 1H), 4.52 (dd, J=5.1, 10.9 Hz, 1H), 3.33-3.13 (m, 1H), 2.88-2.51 (m, 3H), 2.45-0.72 (m, 47H); LC/MS: m/z calculated 717.4. Found 718.3 (M+1)$^+$.

Example 18

4-(((3aS,5aR,5bR,7aR,9S,11aR,11bR,13aS)-3a-((E)-3-((5-Chloropyridin-2-yl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

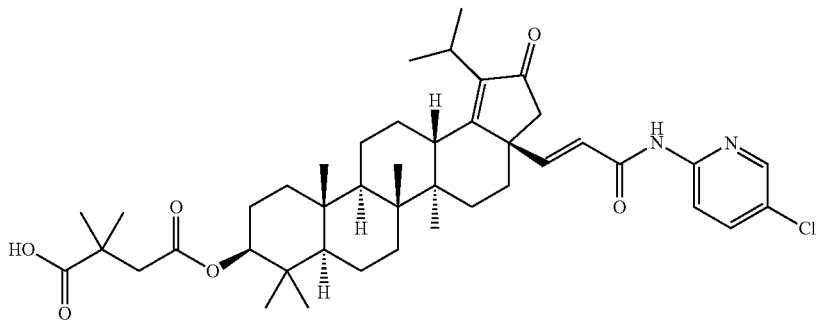

34

To a solution of 1-tert-butyl 4-((3aS,5aR,5bR,7aR,9S,11aR,11bR,13aS)-3a-((E)-3-((5-chloropyridin-2-yl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (100 mg, 0.126 mmol) in dichloromethane (4 mL) stirred at rt was added TFA (2 mL, 26.0 mmol). The reaction mixture was stirred at rt for 1 h. The mixture was evaporated to get the crude product which was purified by preparative-HPLC to give the title compound as a TFA salt (60 mg, 55.9%). $^1$H NMR (400 MHz, CHLOROFORM-d) δ=11.06 (br. s., 1H), 8.54 (d, J=9.0 Hz, 1H), 8.13 (d, J=2.3 Hz, 1H), 7.83 (dd, J=2.3, 9.0 Hz, 1H), 7.10 (d, J=15.8 Hz, 1H), 6.09 (d, J=15.8 Hz, 1H), 4.52 (dd, J=4.3, 11.5 Hz, 1H), 3.30-3.12 (m, 1H), 2.82-2.52 (m, 3H), 2.38-2.08 (m, 3H), 2.04-1.75 (m, 3H), 1.75-0.60 (m, 41H); LC/MS: m/z calculated 734.4. Found 735.3 (M+1)$^+$.

Example 19

4-(((3aS,5aR,5bR,7aR,9S,11aR,11bR,13aS)-3a-((E)-3-((5-Chloropyridin-2-yl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

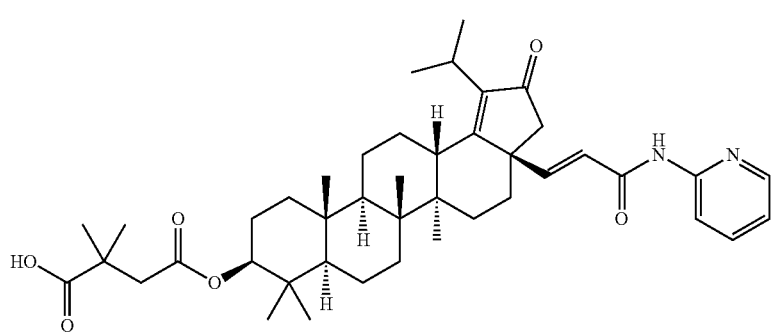

34

To a solution of 1-tert-butyl 4-((3aS,5aR,5bR,7aR,9S,11aR,11bR,13aS)-1-isopropyl-5a,5b,8,8,11a-pentamethyl-2-oxo-3a-((E)-3-oxo-3-(pyridin-2-ylamino)prop-1-en-1-yl)-3,3a,4,5,5a,5b,6,7,7a,8,9,10,11,11a,11b,12,13,13a-octadecahydro-2H-cyclopenta[a]chrysen-9-yl) 2,2-dimethylsuccinate (300 mg, 0.396 mmol) in dichloromethane (6 mL) was added TFA (3 mL, 0.396 mmol). The reaction mixture was stirred at rt for 2 hr and evaporated in vacuo to afford crude product which was purified by preparative-HPLC (Mobile Phase: A=0.05% TFA/H2O, B=MeCN) to give the title compound trifluoroacetic acid salt (100 mg, 0.119 mmol, 30.0%) as a white solid. $^1$H NMR (400 MHz, DMSO-d$_6$) δ=10.72 (br. s., 1H), 8.33 (br. s., 1H), 8.14 (br. s., 1H), 7.83 (br. s., 1H), 7.33-6.97 (m, 1H), 6.97-6.75 (m, 1H), 6.41-6.13 (m, 1H), 4.52-4.25 (m, 1H), 3.35-3.06 (m, 1H), 2.98-2.65 (m, 2H), 2.35-0.53 (m, 47H); LC/MS: m/z calculated 700.5. Found 701.3 (M+1)$^+$.

Example 20

4-(((3aS,5aR,5bR,7aR,9S,11aR,11bR,13aS)-3a-((E)-3-((1-(2-Chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

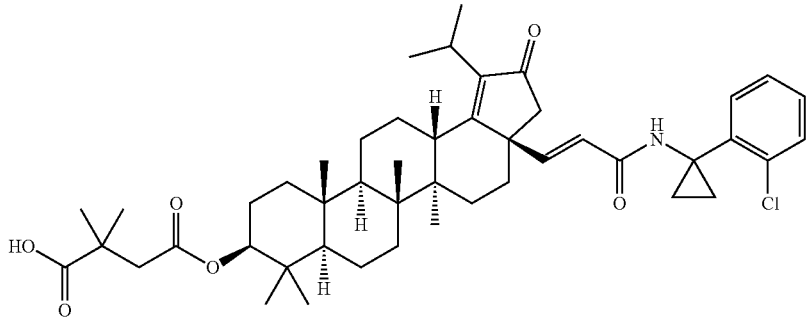

36

To a solution of 1-tert-butyl 4-((3aS,5aR,5bR,7aR,9S,11aR,11bR,13aS)-3a-((E)-3-((1-(2-chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (300 mg, 0.361 mmol) in dichloromethane (6 mL) was added TFA (3 mL, 0.361 mmol). The reaction mixture was stirred at rt for 2 hr and evaporated in vacuo to afford crude product which was purified by preparative-HPLC (Mobile Phase: A=0.05% TFA/H2O, B=MeCN) to give the title compound (110 mg, 0.142 mmol, 39.3%) as a white solid. $^1$H NMR (400 MHz, DMSO-d$_6$) δ=12.23 (br. s., 1H), 8.67 (d, J=7.3 Hz, 1H), 7.67 (br. s., 1H), 7.52-7.13 (m, 3H), 6.69-6.41 (m, 1H), 6.00-5.76 (m, 1H), 4.49-4.20 (m, 1H), 3.29-3.02 (m, 1H), 2.78-2.60 (m, 1H), 2.30-0.57 (m, 53H); LC/MS: m/z calculated 773.4. Found 774.4 (M+1)$^+$.

Example 21

4-(((3aS,5aR,5bR,7aR,9S,11aR,11bR,13aS)-1-Isopropyl-5a,5b,8,8,11a-pentamethyl-2-oxo-3a-((E)-3-oxo-3-(p-tolylamino)prop-1-en-1-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

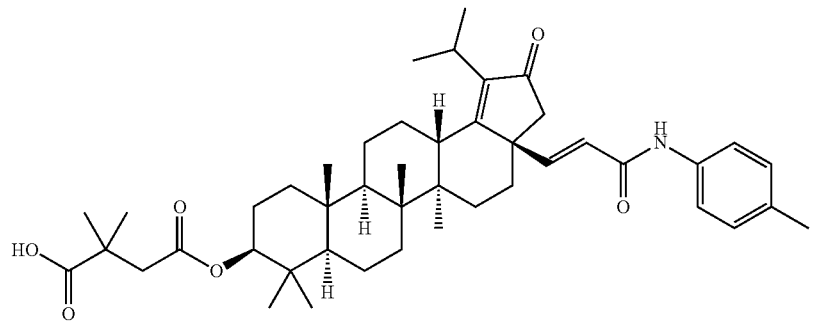

37

To a solution of 1-tert-butyl 4-((3aS,5aR,5bR,7aR,9S,11aR,11bR,13aS)-1-isopropyl-5a,5b,8,8,11a-pentamethyl-2-oxo-3a-((E)-3-oxo-3-(p-tolylamino)prop-1-en-1-yl)-3,3a,4,5,5a,5b,6,7,7a,8,9,10,11,11a,11b,12,13,13a-octadecahydro-2H-cyclopenta[a]chrysen-9-yl) 2,2-dimethylsuccinate (250 mg, 0.325 mmol) in dichloromethane (5 mL) stirred at rt was added TFA (0.025 mL, 0.325 mmol). The reaction mixture was stirred at rt for 1 h. Upon completion and work-up and purification the title compound was obtained as a trifluoroacetic acid salt (150 mg, 0.181 mmol, 55.8%) as a light white solid. $^1$H NMR (300 MHz, DMSO-$d_6$) δ=9.70 (s, 1H), 7.51 (d, J=8.4 Hz, 2H), 7.11 (d, J=8.4 Hz, 2H), 6.83 (d, J=15.8 Hz, 1H), 6.08 (d, J=15.7 Hz, 1H), 4.53-4.32 (m, 1H), 3.30-3.11 (m, 1H), 2.90-2.73 (m, 1H), 2.55-2.51 (m, 1H), 2.35-0.75 (m, 51H); LC/MS: m/z calculated 713.5. Found 714.3 (M+1)$^+$.

Example 22

4-(((3aS,5aR,5bR,7aR,9S,11aR,11bR,13aS)-3a-((E)-3-(((R)-1-(2-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid combined organic phase was washed with H$_2$O (20 mL*2) and brine (30 mL), dried. Then, the solvent was removed under reduced pressure. The residue was purified by preparative-HPLC to give the title compound (70 mg, 0.092 mmol, 91%) was collected as white solid. $^1$H NMR (400 MHz, METHANOL-$d_4$) δ=8.69 (d, J=7.3 Hz, 1H), 7.50-7.17 (m, 4H), 6.83 (d, J=16.1 Hz, 1H), 6.03 (d, J=15.8 Hz, 1H), 5.52-5.35 (m, 1H), 4.50 (dd, J=5.1, 11.2 Hz, 1H), 3.32-3.26 (m, 1H), 3.00-2.80 (m, 1H), 2.73-2.49 (m, 2H), 2.35-0.77 (m, 50H); LC/MS: m/z calculated 761.4. Found 762.3 (M+1)$^+$.

Example 23

4-(((3aS,5aR,5bR,7aR,9S,11aR,11bR,13aS)-3a-((E)-3-(((S)-1-(3-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

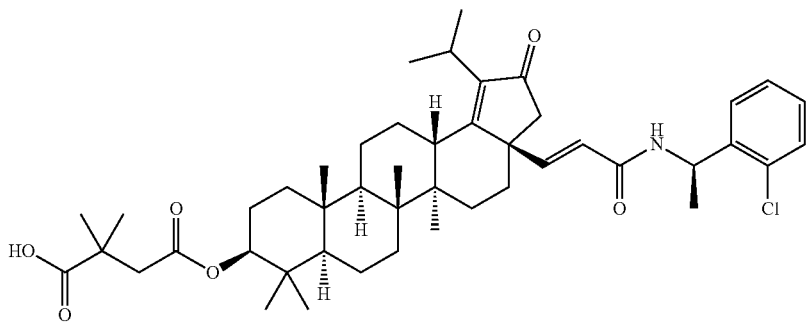

38

To a solution of 1-tert-butyl 4-((3aS,5aR,5bR,7aR,9S,11aR,11bR,13aS)-3a-((E)-3-(((R)-1-(2-chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (200 mg, 0.101 mmol) in dichloromethane (6 mL) stirred at room temp was added TFA (3 ml, 38.9 mmol). The reaction mixture was stirred at 25° C. for 2 h. The product was extracted with DCM (20 mL*2) and the

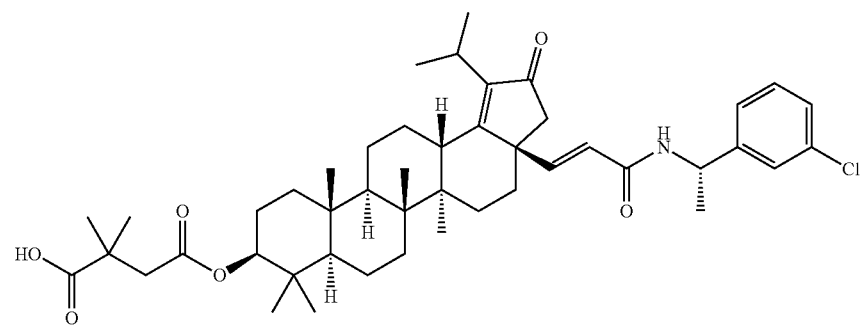

39

To a solution of 1-tert-butyl 4-((3aS,5aR,5bR,7aR,9S,11aR,11bR,13aS)-3a-((E)-3-(((S)-1-(3-chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (12 g, 14.66 mmol) in dichloromethane (130 mL) was added TFA (80 mL, 14.66 mmol). The reaction mixture was stirred at rt for 2 hr and diluted with DCM, washed with water twice. And the organic layer was concentrated, diluted with MeCN/H$_2$O (1:5, 36 mL) and freeze-dried under high vacuo to give the title compound (9.9 g, 12.89 mmol, 88%). This material was combined with several batches made under similar conditions and freeze dried together for characterization (31 g, 41 mmol) as a light yellow solid. $^1$H NMR (400 MHz, CHLOROFORM-d) δ=7.38-7.13 (m, 4H), 6.97 (d, J=15.6 Hz, 1H), 5.82-5.59 (m, 2H), 5.26-5.06 (m, 1H), 4.50 (dd, J=5.3, 11.0 Hz, 1H), 3.29-3.09 (m, 1H), 2.81-2.48 (m, 3H), 2.37-2.00 (m, 3H), 2.00-0.68 (m, 47H).

Example 24

4-(((3aS,5aR,5bR,7aR,9S,11aR,11bR,13aS)-3a-((E)-3-((1-(3-Chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid yl) 2,2-dimethylsuccinate (200 mg, 0.241 mmol) in dichloromethane (5 mL) stirred at rt was added TFA (3 mL, 38.9 mmol). The reaction mixture was stirred at rt for 1 h. The mixture was evaporated to get the crude product which was purified by preparative-HPLC to get the product (100 mg, 53%) as a light white solid. $^1$H NMR (400 MHz, DMSO-d$_6$) δ=12.18 (br. s., 1H), 8.78 (s, 1H), 7.38-7.18 (m, 2H), 7.13 (d, J=5.3 Hz, 1H), 7.08-6.96 (m, 1H), 6.65 (d, J=15.8 Hz, 1H), 5.92 (d, J=16.1 Hz, 1H), 4.39 (dd, J=4.8, 11.0 Hz, 1H), 3.31-3.08 (m, 1H), 2.85-2.72 (m, 1H), 2.63-0.58 (m, 53H); LC/MS: m/z calculated 773.4. Found 772.3 (M−1)$^−$.

Example 25

4-(((3aS,5aR,5bR,7aR,9S,11aR,11bR,13aS)-3a-((E)-3-(((S)-1-(2-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

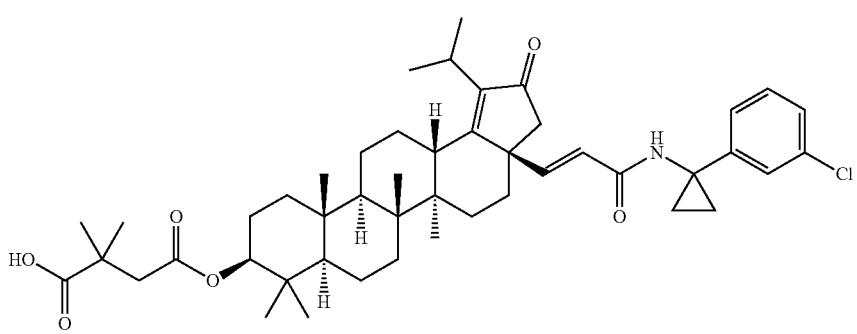

40

To a solution of 1-tert-butyl 4-((3aS,5aR,5bR,7aR,9S,11aR,11bR,13aS)-3a-((E)-3-((1-(3-chlorophenyl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-

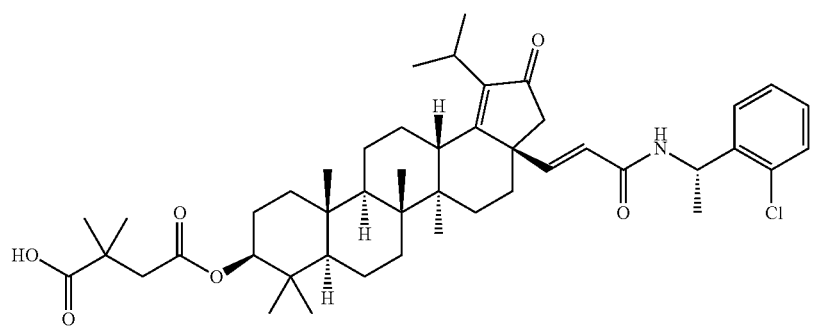

41

To a solution of 1-tert-butyl 4-((3aS,5aR,5bR,7aR,9S,11aR,11bR,13aS)-3a-((E)-3-(((S)-1-(2-chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (150 mg, 0.183 mmol), trifluoroacetic acid (1 mL, 12.98 mmol) in dichloromethane (4 mL) stirred at rt. The reaction mixture was stirred at rt for 2 h. The reaction mixture was evaporated and then purified by preparative-HPLC (Mobile Phase A: Water (0.05% TFA), B: ACN; Gradient 89-89% B in 0-7.5 min, stop at 12 min; Flow Rate (ml/min) 30.00; Retention Time (min) 7.0) to give the title compound (70 mg, 0.092 mmol, 50.1%) as a white solid. $^1$H NMR (400 MHz, METHANOL-d$_4$) δ=7.43-7.32 (m, 2H), 7.32-7.18 (m, 2H), 6.81 (d, J=15.8 Hz, 1H), 6.01 (d, J=15.8 Hz, 1H), 5.41 (q, J=6.9 Hz, 1H), 4.48 (dd, J=5.1, 11.2 Hz, 1H), 3.30-3.24 (m, 1H), 2.94-2.81 (m, 1H), 2.72-2.49 (m, 2H), 2.30-0.75 (m, 50H); LC/MS: m/z calculated 761.4. Found 762.3 (M+1)$^+$.

Example 26

4-(((3aS,5aR,5bR,7aR,9S,11aR,11bR,13aS)-3a-((E)-3-((1-(5-Chloropyrimidin-2-yl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

42

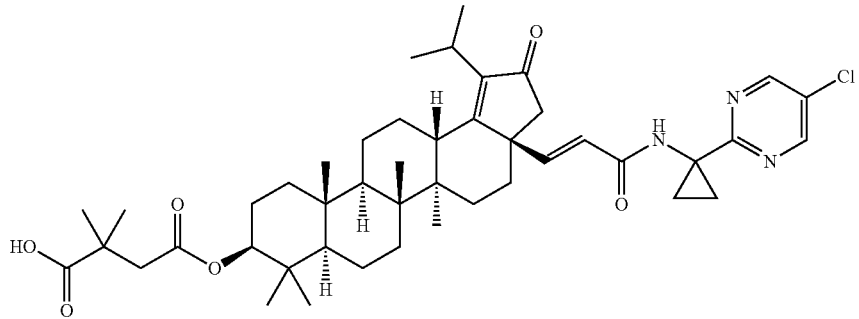

To a solution of 1-tert-butyl 4-((3aS,5aR,5bR,7aR,9S,11aR,11bR,13aS)-3a-((E)-3-((1-(5-chloropyrimidin-2-yl)cyclopropyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (300 mg, 0.360 mmol) in dichloromethane (5 mL) stirred at rt was added TFA (5 mL). The reaction mixture was stirred at rt for 2 h. It was evaporated in vacuo to give crude product which was purified by preparative HPLC to give the title compound (90 mg, 28%) as a light yellow solid. $^1$H NMR (300 MHz, DMSO-d$_6$) δ=8.72 (s, 2H), 8.54 (br. s., 1H), 6.70 (d, J=15.8 Hz, 1H), 5.94 (d, J=15.8 Hz, 1H), 4.55-4.29 (m, 1H), 3.31-3.07 (m, 1H), 2.94-2.64 (m, 1H), 2.59-0.60 (m, 52H); LC/MS: m/z calculated 775.4. Found 776.3 (M+1)$^+$.

Example 27

4-(((3aS,5aR,5bR,7aR,9S,11aR,11bR,13aS)-3a-((E)-3-((1-(4-Chlorophenyl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

43

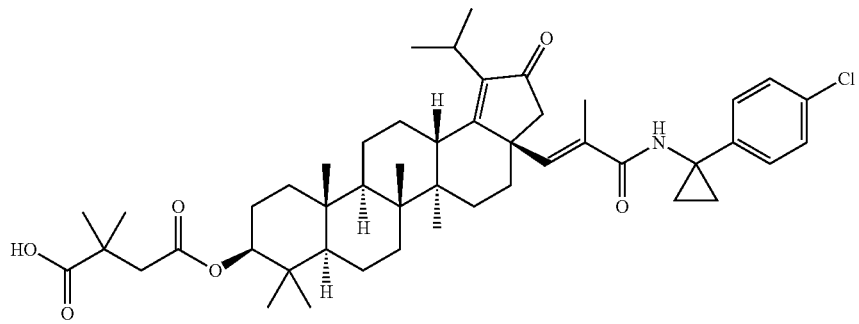

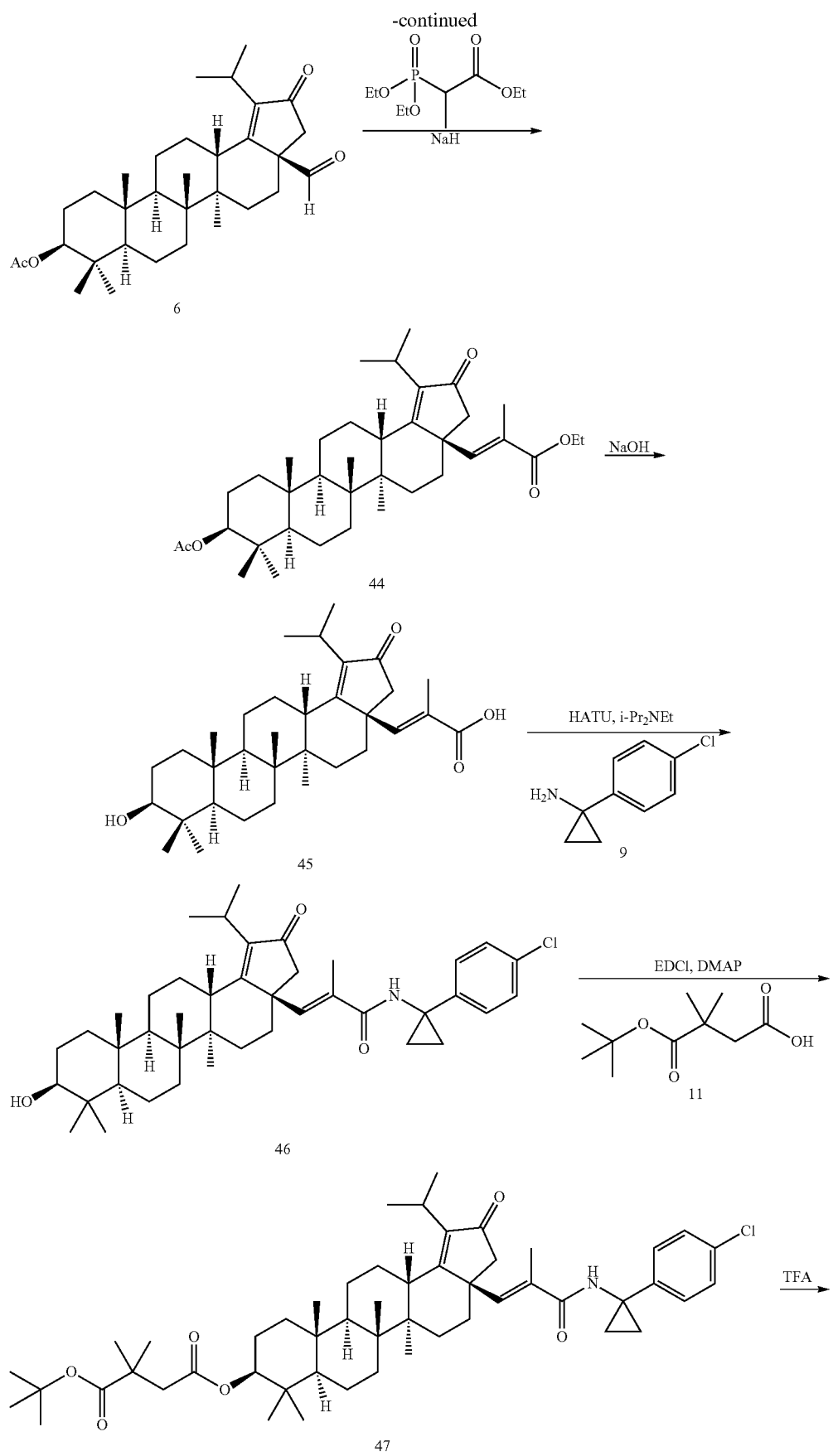

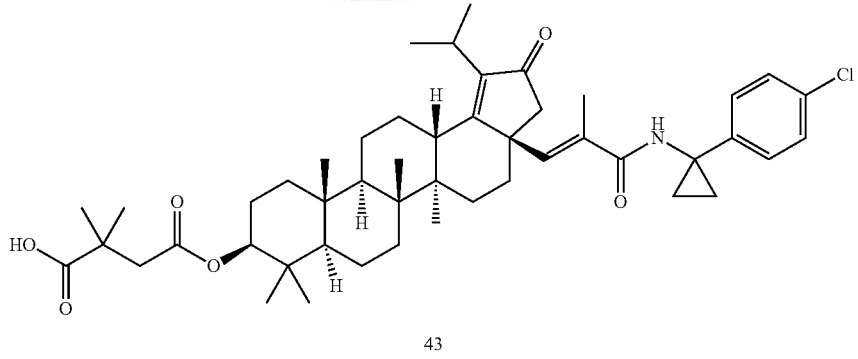

43

Step A

Intermediate 44

(E)-Ethyl 3-((3aS,5aR,5bR,7aR,9S,11aR,11bR, 13aS)-9-acetoxy-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-3a-yl)-2-methylacrylate To a suspension of ethyl 2-(diethoxyphosphoryl)propanoate (3.12 g, 13.09 mmol) in DMF (35 mL) stirred under nitrogen at 0° C. was added NaH (0.60 g, 80 wt %, 20 mmol) during 5 min and stirred for 10 mins. The solution was warmed to rt and stirred for 30 mins before (3aR,5aR,5bR, 7aR,9S,11aR,11bR,13aS)-3a-formyl-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl acetate (5.0 g, 10 mmol) was added to above mixture. After overnight, the reaction was quenched with water and washed with saturated NaHCO$_3$ and water. The solid was solved into EtOAc, dried over Na$_2$SO$_4$, filtered and concentrated to remove the majority of solvent. The residue was recrystalized from petroleum ether/EtOAc (8:1), filtered and the filtrate was concentrated to give the residue, which was purified by silica gel eluting with petroleum ether/EtOAc (15:1-10:1) to obtain the product (E)-ethyl 3-((3aS,5aR,5bR,7aR,9S, 11aR,11bR,13aS)-9-acetoxy-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-3a-yl)-2-methylacrylate (1.0 g, 1.291 mmol, 12.82%) as a yellow solid.

Step B

Intermediate 45

(E)-3-((3aS,5aR,5bR,7aR,9S,11aR,11bR,13aS)-9-Hydroxy-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-3a-yl)-2-methylacrylic acid To a solution of (E)-ethyl 3-((3aS,5aR,5bR,7aR,9S,11aR, 11bR,13aS)-9-acetoxy-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-3a-yl)-2-methylacrylate (2.0 g, 3.44 mmol) in THF (12 mL), MeOH (8 mL) and water (4 mL) was added sodium hydroxide (5.51 g, 138 mmol). The reaction mixture was stirred at 20° C. for 2 hrs. The reaction mixture was evaporated to dryness and the pH was adjusted to 5 with saturated NH$_4$Cl. The solid is solved into DCM (50 mL), washed with water, dried over Na$_2$SO$_4$ and concentrated to yield the (E)-3-((3aS,5aR,5bR, 7aR,9S,11aR,11bR,13aS)-9-hydroxy-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-3a-yl)-2-methylacrylic acid (1.3 g, 54.8%) as a yellow solid.

Step C

Intermediate 46

(E)-N-(1-(4-Chlorophenyl)cyclopropyl)-3-((3aS, 5aR,5bR,7aR,9S,11aR,11bR,13aS)-9-hydroxy-1-isopropyl-5a,5b,8,8,11a-pentamethyl-2-oxo-3,3a,4,5, 5a,5b,6,7,7a,8,9,10,11,11a,11b, 12,13,13a-octadecahydro-2H-cyclopenta[a]chrysen-3a-yl)-2-methylacrylamide To a solution of (E)-3-((3aS,5aR,5bR,7aR,9S,11aR,11bR, 13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-methylacrylic acid (350 mg, 0.685 mmol), 1-(4-chlorophenyl)cyclopropanamine hydrochloride (154 mg, 0.754 mmol) and HATU (521 mg, 1.371 mmol) in DMF (2 mL) stirred at 0° C. was added DIPEA (0.479 mL, 2.74 mmol). The reaction mixture was stirred at 20° C. for 1 h. The reaction mixture was pH adjusted to 3-4 with 2 M HCl and filtered. The solid was washed with water (50 mL), dissolved into DCM, dried over sodium sulfate and evaporated in vacuo to give the crude (E)-N-(1-(4-chlorophenyl)cyclopropyl)-3-((3aS,5aR,5bR,7aR,9S,11aR,11bR,13aS)-9-hydroxy-1-isopropyl-5a,5b,8,8,11a-pentamethyl-2-oxo-3,3a,4,5,5a,5b,6,7, 7a,8,9,10,11,11a,11b,12,13,13a-octadecahydro-2H-cyclopenta[a]chrysen-3a-yl)-2-methylacrylamide (650 mg, 0.680 mmol, 99%) as a yellow solid.

Step D

Intermediate 47

1-tert-Butyl 4-((3aS,5aR,5bR,7aR,9S,11aR,11bR,13aS)-3a-((E)-3-((1-(4-chlorophenyl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate To a solution of DMAP (415 mg, 3.40 mmol), EDC (652 mg, 3.40 mmol) and 4-tert-butoxy-3,3-dimethyl-4-oxobutanoic acid (425 mg, 2.039 mmol) in DCM (10 mL) stirred at 20° C. for 30 min was added (E)-N-(1-(4-chlorophenyl)cyclopropyl)-3-((3aS,5aR,5bR,7aR,9S,11aR,11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-methylacrylamide (650 mg, 0.680 mmol). The reaction mixture was stirred at 20° C. for 2 h. The mixture was washed with saturated ammonium chloride, water, and saturated NaHCO$_3$, water and brine. The organic layer was dried over Na$_2$SO$_4$, filtered and concentrated to give the crude product, which was purified by silica gel column eluting with petroleum ether/Ethyl acetate (3:1) to afford 1-tert-butyl 4-((3aS,5aR,5bR,7aR,9S,11aR,11bR,13aS)-3a-((E)-3-((1-(4-chlorophenyl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (300 mg, 52%) as a light yellow solid. $^1$H NMR (400 MHz, CHLOROFORM-d) δ=7.30-7.22 (m, 2H), 7.22-7.14 (m, 2H), 6.59 (s, 1H), 6.32 (s, 1H), 4.51 (dd, J=5.4, 10.9 Hz, 1H), 3.28-3.10 (m, 1H), 2.72 (d, J=10.3 Hz, 1H), 2.55 (s, 3H), 2.41-2.21 (m, 2H), 2.12-0.71 (m, 61H).

Step E 4-(((3aS,5aR,5bR,7aR,9S,11aR,11bR,13aS)-3a-((E)-3-((1-(4-Chlorophenyl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid To a solution of 1-tert-butyl 4-((3aS,5aR,5bR,7aR,9S,11aR,11bR,13aS)-3a-((E)-3-((1-(4-chlorophenyl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (300 mg, 0.355 mmol) in DCM (6 mL) was added TFA (3 mL, 0.355 mmol). The reaction mixture was stirred at rt for 2 hr and evaporated in vacuo to afford crude product which was diluted with DCM (30 mL) and washed with water, saturated NaHCO$_3$, water, saturated NH$_4$Cl and water. The organic layer was dried over Na$_2$SO$_4$, filtered and concentrated to obtain a residue which was dissolved into MeCN—H$_2$O (1:2, 9 mL) and freeze-dried to give the title compound (150 mg, 0.190 mmol, 53.6%) as a white solid. $^1$H NMR (400 MHz, DMSO-d$_6$) δ=12.81-11.61 (m, 1H), 8.73-8.51 (m, 1H), 7.28 (d, J=8.3 Hz, 2H), 7.22-7.04 (m, 2H), 6.54 (s, 1H), 4.39 (dd, J=4.9, 11.2 Hz, 1H), 3.23-3.10 (m, 1H), 2.79-0.44 (m, 57H); LC/MS: m/z calculated 787.5. Found 788.3 (M+1)$^+$.

Example 28

4-(((3aS,5aR,5bR,7aR,9S,11aR,11bR,13aS)-3a-((E)-3-((1-(5-Chloropyrimidin-2-yl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

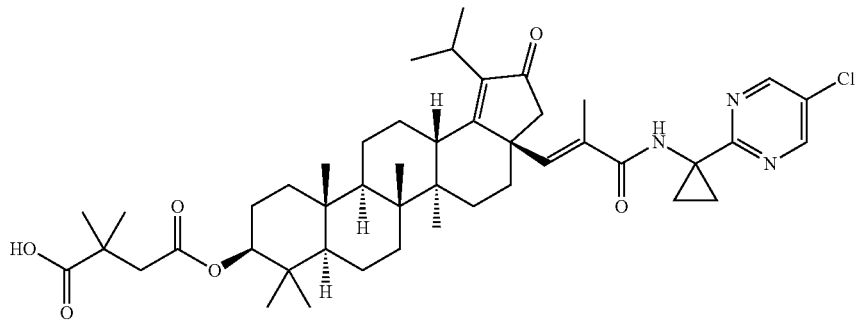

48

To a solution of 1-tert-butyl 4-((3aS,5aR,5bR,7aR,9S,11aR,11bR,13aS)-3a-((E)-3-((1-(5-chloropyrimidin-2-yl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (250 mg, 0.295 mmol) in DCM (6 mL) was added TFA (3 mL, 0.295 mmol). The reaction mixture was stirred at rt for 2 hr and evaporated in vacuo to afford crude product. This material was diluted with DCM (30 mL), and washed with water, saturated NaHCO$_3$, water, saturated NH$_4$Cl and water. The organic layer was dried over Na$_2$SO$_4$, filtered and concentrated to obtain a residue which was dissolved into MeCN—H$_2$O (1:2, 9 mL) and freeze-dried to give the title compound (120 mg, 0.149 mmol, 50.4%) as a white solid. $^1$H NMR (400 MHz, DMSO-d$_6$) δ=12.22 (br. s., 1H), 8.75 (s, 2H), 8.60 (s, 1H), 6.57 (s, 1H), 4.39 (dd, J=4.8, 11.3 Hz, 1H), 3.24-3.10 (m, 1H), 2.82-0.59 (m, 57H); LC/MS: m/z calculated 789.5. Found 790.3 (M+1)$^+$.

Example 29

4-(((3aS,5aR,5bR,7aR,9S,11aR,11bR,13aS)-3a-((E)-3-((1-(3-Chlorophenyl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

Example 30

4-(((3aS,5aR,5bR,7aR,9S,11aR,11bR,13aS)-3a-((E)-3-(Cyclohexylamino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

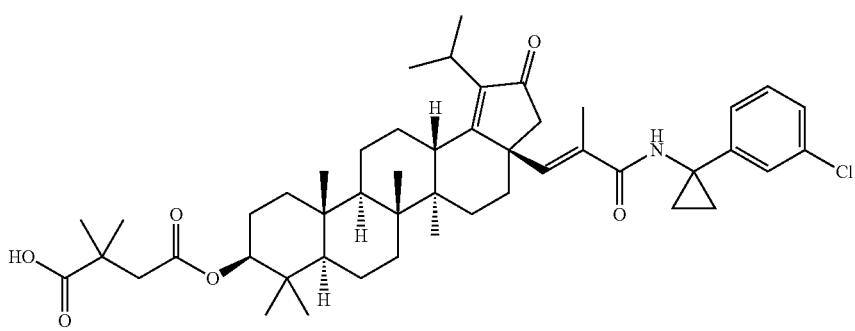

49

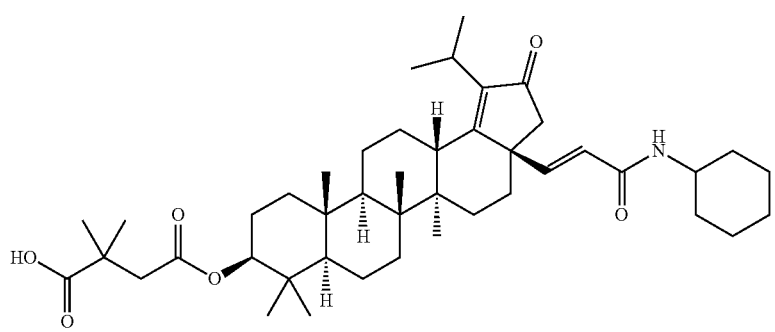

50

To a solution of 1-tert-butyl 4-((3aS,5aR,5bR,7aR,9S,11aR,11bR,13aS)-3a-((E)-3-((1-(3-chlorophenyl)cyclopropyl)amino)-2-methyl-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (280 mg, 0.332 mmol) in DCM (6 mL) was added TFA (3 mL, 0.332 mmol). The reaction mixture was stirred at rt for 2 hr and evaporated in vacuo to afford crude product. This was diluted with DCM (30 mL), and washed with water, saturated NaHCO$_3$, water, saturated NH$_4$Cl and then water. The organic layer was dried over Na$_2$SO$_4$, filtered and concentrated to obtain a residue, which was dissolved into MeCN—H$_2$O (1:2, 9 mL) and freeze-dried to give the title compound (130 mg, 48%) as a white solid. $^1$H NMR (400 MHz, DMSO-d$_6$) δ=12.16 (br. s., 1H), 8.62 (s, 1H), 7.34-7.17 (m, 2H), 7.14 (s, 1H), 7.05 (d, J=7.5 Hz, 1H), 6.57 (s, 1H), 4.40 (dd, J=4.4, 10.9 Hz, 1H), 3.23-3.08 (m, 1H), 2.83-0.62 (m, 57H); LC/MS: m/z calculated 787.5. Found 788.2 (M+1)$^+$.

To a solution of 1-tert-butyl 4-((3aS,5aR,5bR,7aR,9S,11aR,11bR,13aS)-3a-((E)-3-(cyclohexylamino)-3-oxoprop-1-en-1-yl)-1-isopropyl-5a,5b,8,8,11a-pentamethyl-2-oxo-3, 3a,4,5,5a,5b,6,7,7a,8,9,10,11,11a,11b,12,13,13a-octadecahydro-2H-cyclopenta[a]chrysen-9-yl) 2,2-dimethylsuccinate (400 mg, 0.525 mmol) in DCM (10 mL) stirred at room temp was added TFA (5 mL, 64.9 mmol). The reaction mixture was stirred at 30° C. for 2 h. The mixture was evaporated to dryness, then diluted by 200 mL DCM. The organic phase was washed with saturated NaHCO$_3$ solution, water and saturated brine, dried and concentrated under reduced pressure to afford crude product. This material was further purified by preparative-HPLC to afford the title compound (120 mg, 32%) as a white solid. $^1$H NMR (400 MHz, CHLOROFORM-d) δ=6.92 (d, J=15.8 Hz, 1H), 5.62 (d, J=15.8 Hz, 1H), 5.37 (d, J=8.3 Hz, 1H), 4.50 (dd, J=5.3, 11.0 Hz, 1H), 3.94-3.73 (m, 1H), 3.27-3.14 (m, 2H), 2.80-2.51 (m, 3H), 2.37-2.03 (m, 3H), 2.03-0.69 (m, 54H); LC/MS: m/z calculated 705.5. Found 706.3 (M+1)$^+$.

h. The mixture was evaporated to dryness then diluted with 200 mL DCM. The organic phase was washed with saturated NaHCO$_3$, water and brine. The organics were dried and concentrated under reduced pressure to afford crude product which was purified by preparative-HPLC to afford the title compound (100 mg, 27%) as a white solid. $^1$H NMR (400 MHz, CHLOROFORM-d) δ=7.38-7.14 (m, 4H), 6.96 (d, J=15.8 Hz, 1H), 6.25 (d, J=7.8 Hz, 1H), 5.73 (d, J=15.6 Hz, 1H), 5.23-5.08 (m, 1H), 4.50 (dd, J=5.4, 10.7 Hz, 1H), 3.27-3.11 (m, 1H), 2.82-2.49 (m, 3H), 2.33-2.19 (m, 1H), 2.19-2.00 (m, 2H), 2.00-0.71 (m, 47H); LC/MS: m/z calculated 761.4. Found 762.2 (M+1)$^+$.

Example 31

4-(((3aS,5aR,5bR,7aR,9S,11aR,11bR,13aS)-3a-((E)-3-(((R)-1-(3-Chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

Example 32

4-(((3aS,5aR,5bR,7aR,9S,11aR,11bR,13aS)-3a-((E)-3-((2-Hydroxyethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

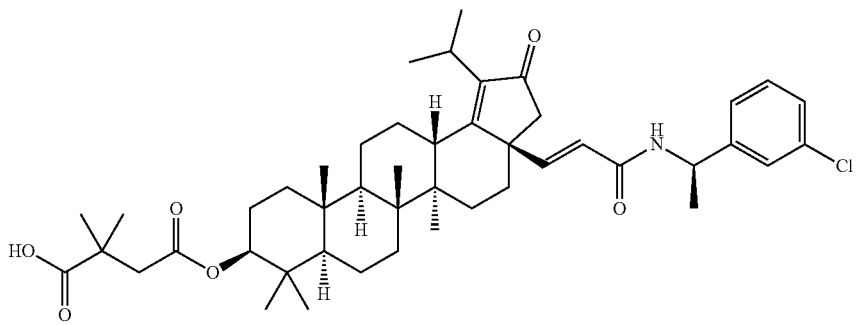

51

To a solution of 1-tert-butyl 4-((3aS,5aR,5bR,7aR,9S,11aR,11bR,13aS)-3a-((E)-3-(((R)-1-(3-chlorophenyl)ethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (400 mg, 0.489 mmol) in DCM (10 mL) that was stirred at room temp was then added TFA (5 mL, 64.9 mmol). The reaction mixture was stirred at 30° C. for 2

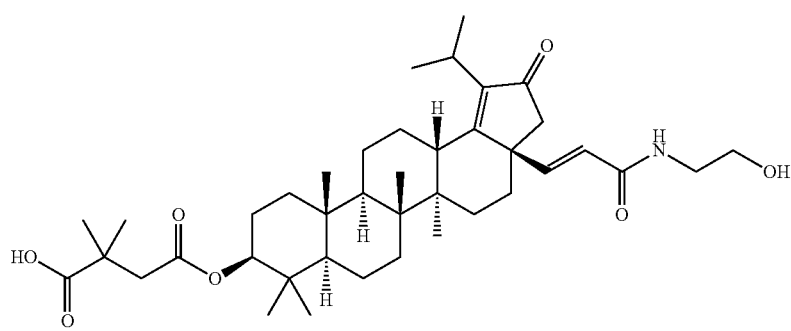

52

To a solution of 1-tert-butyl 4-((3aS,5aR,5bR,7aR,9S,11aR,11bR,13aS)-3a-((E)-3-((2-hydroxyethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (60 mg, 0.083 mmol) in DCM (5 mL) stirred at room temp was added TFA (2.5 mL, 32.4 mmol). The reaction mixture was stirred at 30° C. for 2 h. The reaction was evaporated to dryness then diluted with 200 mL DCM. The organic phase was washed with saturated NaHCO$_3$ solution (200 mL*3), water and brine. The organics were dried and concentrated under reduced pressure to afford crude product which was further purified by preparative-HPLC to afford the title compound (35 mg, 63%) as a white solid. $^1$H NMR (400 MHz, METHANOL-d$_4$) δ=6.85 (d, J=16.1 Hz, 1H), 5.96 (d, J=16.1 Hz, 1H), 4.49 (dd, J=5.5, 10.5 Hz, 1H), 3.64 (t, J=5.6 Hz, 2H), 3.39 (t, J=5.6 Hz, 2H), 3.37-3.21 (m, 1H), 2.91 (dd, J=4.1, 11.7 Hz, 0H), 2.68-2.50 (m, 2H), 2.33-2.10 (m, 3H), 2.09-0.75 (m, 44H).

Example 33

4-(((3aS,5aR,5bR,7aR,9S,11aR,11bR,13aS)-3a-((E)-3-((Cyclohexylmethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

53

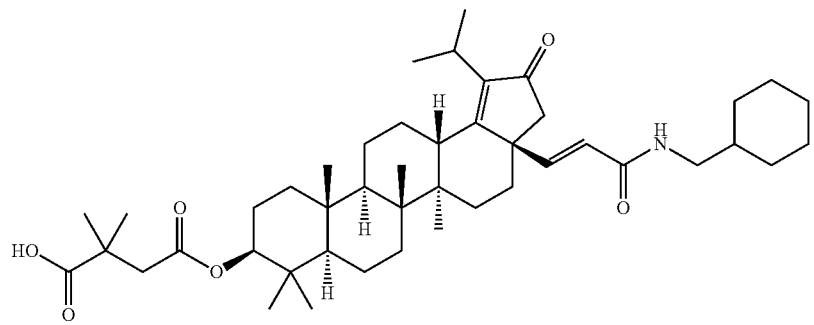

To a solution of 1-tert-butyl 4-((3aS,5aR,5bR,7aR,9S,11aR,11bR,13aS)-3a-((E)-3-((cyclohexylmethyl)amino)-3-oxoprop-1-en-1-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 2,2-dimethylsuccinate (200 mg, 0.258 mmol) in DCM (10 mL) stirred at room temp was added TFA (5 mL, 64.9 mmol). The reaction mixture was stirred at 30° C. for 2 h. The product was evaporated to dryness and then diluted with 200 mL DCM. The organic phase was washed with saturated NaHCO$_3$, water and brine. The organics were dried and concentrated under reduced pressure to afford crude product, which was purified by preparative-HPLC to afford the title compound (55 mg, 29%) as a white solid. $^1$H NMR (400 MHz, DMSO-d$_6$) δ=12.18 (br. s., 1H), 7.93 (t, J=5.8 Hz, 1H), 6.60 (d, J=15.8 Hz, 1H), 5.89 (d, J=15.8 Hz, 1H), 4.39 (dd, J=4.6, 11.2 Hz, 1H), 3.27-3.12 (m, 1H), 3.03-2.87 (m, 2H), 2.73 (dd, J=3.5, 11.8 Hz, 1H), 2.24-1.99 (m, 3H), 1.96-0.70 (m, 57H); LC/MS: m/z calculated 719.5. Found 720.5 (M+1)$^+$.

Example 34

4-(((3aR,5aR,5bR,7aR,9S,11aR,11bR,13aS)-3a-((E)-3-(((S)-1-(3-Chlorophenyl)ethyl)amino)-3-oxoprop-1-en-1-yl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

54

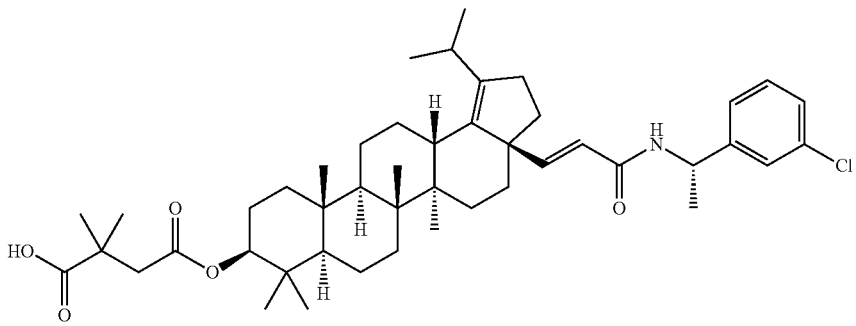

-continued
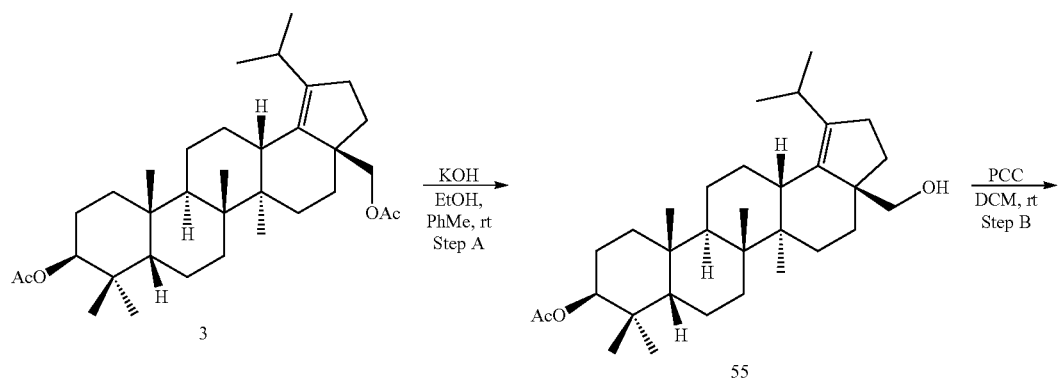
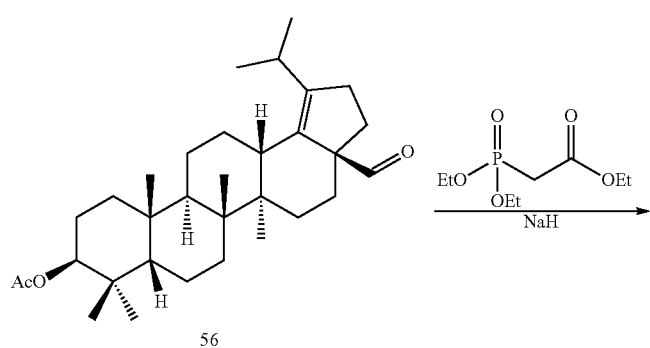
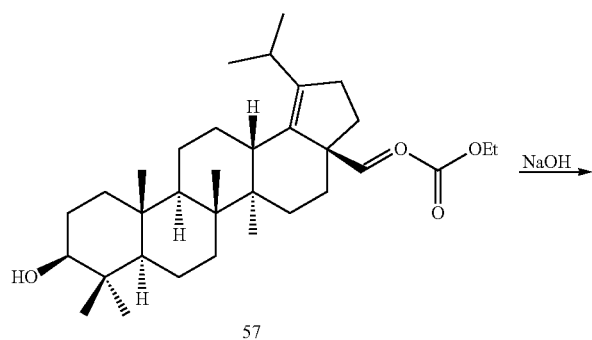
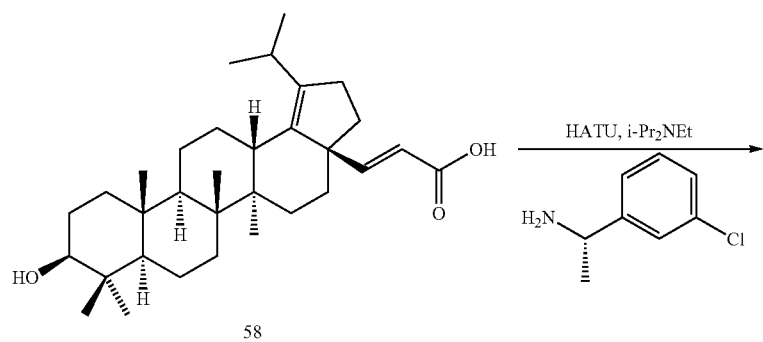

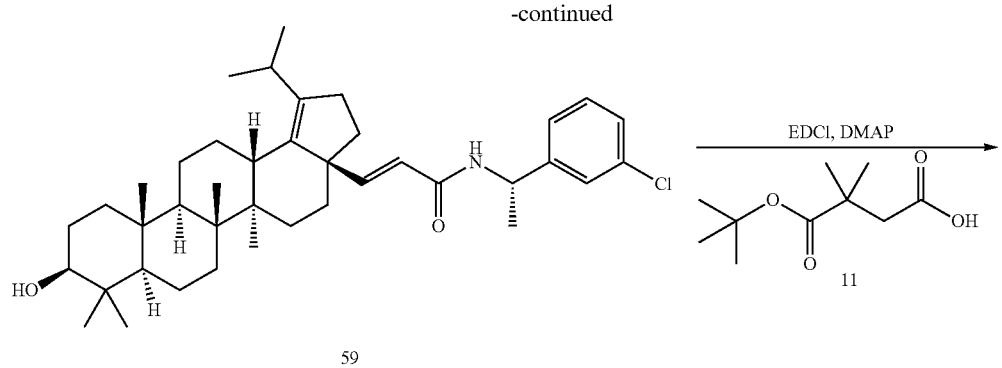

59

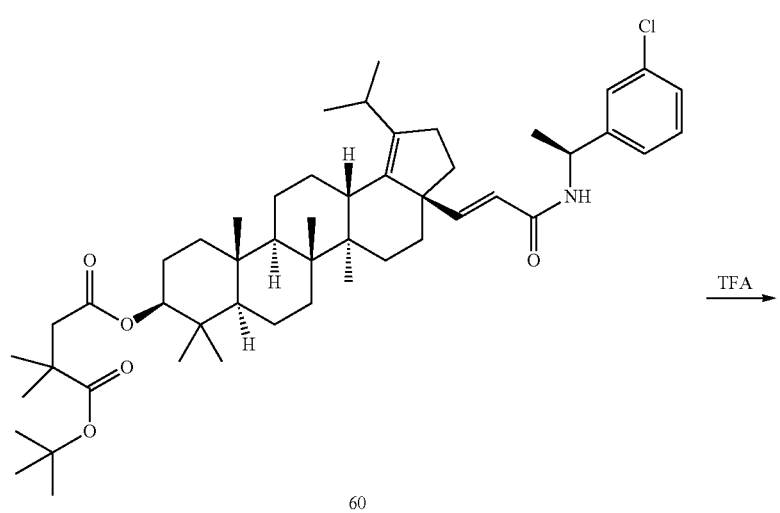

60

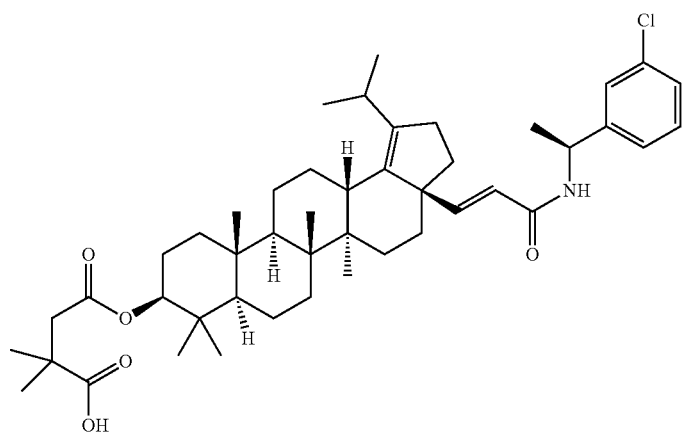

54

55

Step A

Intermediate 55

(3aS,5aR,5bR,7aR,9S,11aR,11bR,13aS)-3a-(Hydroxymethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl acetate To a solution of the intermediate 3 (5 g, 7.59 mmol) in EtOH (100 mL) and toluene (100 mL) was added KOH (0.51 g, 9.11 mmol). After stirring at room temperature for 4 h, the reaction mixture was then partitioned between water (500 mL) and EtOAc (500 mL). The organic phase was washed with water (200 mL×3), brine (100 mL), and dried over sodium sulfate. Removal of the solvent provided a residue, which was purified by column chromatography on silica gel (Hex:EtOAc=6:1 to 4:1) to afford the intermediate 55 (2.5 g, 67.9%) as a white solid. $^1$H NMR (400 Hz, CDCl$_3$) 5 ppm 4.50-4.67 (1H, m), 3.68 (1H, d, J=10.4 Hz), 3.32 (1H, d, J=10.4 Hz), 3.23-3.15 (1H, m), 2.42-2.28 (3H, m), 2.05 (3H, s), 2.02-1.89 (2H, m), 1.77-0.83 (40H, m).

Step B

Intermediate 56

(3aS,5aR,5bR,7aR,9S,11aR,11bR,13aS)-3a-Formyl-1-isopropyl-5a,5b,8,8,11a-pentamethyl-3,3a,4,5,5a, 5b,6,7,7a,8,9,10,11,11a,11b,12,13,13a-octadecahydro-2H-cyclopenta[a]chrysen-9-yl acetate To a solution of the intermediate 55 (3 g, 6.19 mmol) in DCM (75 mL) at room temperature were added PCC (4 g, 18.57 mmol) and silica gel (3.0 g). After stirring at room temperature for 2 h, the reaction was quenched with water (100 mL). The organic phase was separated, washed with saturated sodium bicarbonate (50 mL), dried over sodium sulfate and concentrated in vacuo to provide a residue, which was purified by column chromatography on silica gel (Hex:EtOAc=10:1) to afford the intermediate 56 (3 g, 100%) as a white solid. $^1$H NMR (400 Hz, CDCl$_3$) 5 ppm 9.43 (1H, s), 4.50-4.46 (1H, m), 3.25-3.21 (1H, m), 2.43-2.02 (5H, m), 2.04 (3H, m), 2.00-1.93 (1H, m), 1.75-0.81 (38H, m).

Step C

Intermediate 57

(E)-ethyl 3-((3aR,5aR,5bR,7aR,9S,11aR,11bR,13aS)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-3a-yl)acrylate To a suspension of ethyl 2-(diethoxyphosphoryl)acetate (7.80 g, 34.8 mmol) in anhydrous N,N-Dimethylformamide (DMF) (20 ml) and Tetrahydrofuran (THF) (10 ml) stirred under nitrogen at 0° C. was added NaH (1.288 g, 32.2 mmol) dropwise during 5 min and stirred for 10 mins. The solution was warmed to rt and stirred for 30 mins before (3aS,5aR,5bR,7aR,9S,11aR,11bR,13aS)-3a-formyl-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl acetate (4.2 g, 8.70 mmol) was added to above mixture. After sitting overnight, the reaction was quenched by water and washed with saturated NaHCO$_3$, water and brine. The organic fraction was dried over sodium sulfate, filtered and concentrated to give a residue, which was purified on a silica gel column (petrol ether/EtOAc=10:1) to obtain the pure product (E)-ethyl 3-((3aR,5aR,5bR,7aR,9S,11aR,11bR,13aS)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-3a-yl)acrylate (3.1 g, 69%) as a white foam. $^1$H NMR (400 MHz, CHLOROFORM-d) δ=7.01-6.84 (m, 2H), 5.64 (d, J=16.1 Hz, 1H), 4.20 (q, J=7.3 Hz, 2H), 3.26-3.07 (m, 3H), 2.40-2.11 (m, 5H), 2.08-1.91 (m, 2H), 1.89-0.61 (m, 43H).

Step D

Intermediate 58

(E)-3-((3aR,5aR,5bR,7aR,9S,11aR,11bR,13aS)-9-Hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-3a-yl)acrylic acid To a solution of (E)-ethyl 3-((3aR,5aR,5bR,7aR,9S,11aR,11bR,13aS)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-3a-yl)acrylate (2 g, 3.92 mmol) in THF (15 mL), methanol (10 mL) and water (5 mL) was added sodium hydroxide (3.13 g, 78 mmol). The reaction mixture was stirred at rt for 4 hr. Next, saturated NH$_4$Cl was added. The suspended precipitate was filtered and dried to yield the intermediate 58 (1.72 g, 69%) as a white solid. $^1$H NMR (400 MHz, CHLOROFORM-d) δ=7.05 (d, J=15.8 Hz, 1H), 5.66 (d, J=16.1 Hz, 1H), 3.30-3.07 (m, 2H), 2.28 (br. s., 3H), 2.08-1.93 (m, 1H), 1.91-0.59 (m, 40H).

Step E

Intermediate 59

(E)-N—((S)-1-(3-Chlorophenyl)ethyl)-3-((3aR,5aR,5bR,7aR,9S,11aR,11bR,13aS)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-3a-yl)acrylamide To a solution of (E)-3-((3aR,5aR,5bR,7aR,9S,11aR,11bR,13aS)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-3a-yl)acrylic acid (1 g, 2.072 mmol), (S)-1-(3-chlorophenyl)ethanamine, hydrochloride (0.477 g, 2.486 mmol) and HATU (1.575 g, 4.14 mmol) in DMF (5 ml) stirred at rt was added DIPEA (1.447 ml, 8.29 mmol). The reaction mixture was stirred at rt for 3 h. The reaction mixture was extracted with EtOAc, filtered through a short column of silical gel to obtain intermediate 59 (1.2 g, 1.569 mmol, 76% yield). $^1$H NMR (400 MHz, CHLOROFORM-d) δ=7.40-7.13 (m, 4H), 6.99-6.77 (m, 1H), 5.70-5.50 (m, 2H), 5.27-5.12 (m, 1H), 3.27-3.08 (m, 2H), 2.41-2.14 (m, 3H), 2.07-1.93 (m, 1H), 1.88-0.58 (m, 43H).

Step F

Intermediate 60

1-tert-Butyl 4-((3aR,5aR,5bR,7aR,9S,11aR,11bR,13aS)-3a-((E)-3-(((S)-1-(3-chlorophenyl)ethyl)amino)-3-oxoprop-1-en-1-yl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl) 2,2-dimethylsuccinate To a solution of 4-tert-butoxy-3,3-dimethyl-4-oxobutanoic acid (1.174 g, 5.80 mmol), DMAP (0.709 g, 5.80 mmol) in DCM (20 mL) stirred at rt was added EDCl (1.854 g, 9.67 mmol). The reaction mixture was stirred at rt for 2 h. (E)-N—((S)-1-(3-Chlorophenyl)ethyl)-3-((3aR,5aR,5bR,7aR,9S,11aR,11bR,13aS)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-3a-yl)acrylamide (1.2 g, 1.934 mmol) was added to the reaction mixture. The resultant mixture was stirred at rt overnight. Water was added and the mixture was partitioned and washed with additional water. The organics were dried over sodium sulfate filtered through a short silica gel column and evaporated in vacuo to give the crude product as yellow foam. This material was used in the next step without further purification.

Step G

Compound 54

4-(((3aR,5aR,5bR,7aR,9S,11aR,11bR,13aS)-3a-((E)-
3-(((S)-1-(3-Chlorophenyl)ethyl)amino)-3-oxoprop-
1-en-1-yl)-1-isopropyl-5a,5b,8,8,11a-pentamethyl-3,
3a,4,5,5a,5b,6,7,7a,8,9,10,11,11a,11b,12,13,13a-
octadecahydro-2H-cyclopenta[a]chrysen-9-yl)oxy)-
2,2-dimethyl-4-oxobutanoic acid To a solution of 1-tert-butyl 4-((3aR,5aR,5bR,7aR,9S, 11aR,11bR,13aS)-3a-((E)-3-(((S)-1-(3-chlorophenyl)ethyl) amino)-3-oxoprop-1-en-1-yl)-1-isopropyl-5a,5b,8,8,11a-pentamethyl-3,3a,4,5,5a,5b,6,7,7a,8,9,10,11,11a,11b,12,13, 13a-octadecahydro-2H-cyclopenta[a]chrysen-9-yl) 2,2-dimethylsuccinate (1556 mg, 1.934 mmol) in DCM (12 mL) stirred at room temp was added TFA (4 mL, 51.9 mmol). The reaction mixture was stirred at rt for 2 h. The mixture was evaporated to dryness, then diluted with 200 ml DCM. The organic phase was washed with saturated $NaHCO_3$ solution (200 mL*3), water and brine. The organics were dried and concentrated under reduced pressure to afford the crude product which was purified by preparative-HPLC to give the title compound (550 mg, 38%) as a white solid. $^1$H NMR (400 MHz, CHLOROFORM-d) δ=7.40-7.17 (m, 4H), 6.85 (d, J=15.3 Hz, 1H), 5.72-5.49 (m, 2H), 5.18 (t, J=7.2 Hz, 1H), 4.50 (dd, J=5.6, 10.7 Hz, 1H), 3.28-3.10 (m, 1H), 2.74-2.62 (m, 1H), 2.62-2.50 (m, 1H), 2.24 (br. s., 3H), 2.08-1.92 (m, 2H), 1.89-0.70 (m, 49H); LC/MS: m/z calculated 747.5. Found 748.2 $(M+1)^+$.

Example 35

MT4 Cell Antiviral Assay

Experimental Procedure

Antiviral HIV activity and compound-induced cytotoxicity were measured in parallel based on a modified protocol of the propidium iodide based procedure in the human T-cell lymphotropic virus transformed cell line MT4. Aliquots of the test compounds were serially diluted in DMSO plated in 96-well plates. Exponentially growing MT4 cells were harvested and pelleted. Cell pellets were resuspended in fresh medium (RPMI 1640, 10% FCS, and gentamycin. Cell aliquots were infected by the addition of HIV-1 (strain IIIB) diluted to give a viral multiplicity of infection of 300× TCID50/million cells. A similar cell aliquot was diluted with medium to provide a mock-infected control. Cell infection was allowed to proceed for 1 hr at 37° C. in a tissue culture incubator with humidified 5% $CO_2$ atmosphere. After the 1 hr incubation the virus/cell suspensions were diluted with fresh medium, and added to each well of the plate containing pre-diluted compound. Plates were then placed in a tissue culture incubator with humidified 5% $CO_2$ for 5 days. At the end of the incubation period, cell number and hence HIV-induced cytopathy was estimated by the addition of Cell Titer-Glo (Promega). The plates were analyzed in an automated plate reader for luminescence.assay. The control and standard used was efavirinz tested over a concentration range of 0.001 to 1 µM in every assay. The expected range of $IC_{50}$ values for efavirinz is 0.1 to 1 nM.

Analysis

The antiviral effect of a test compound is reported as an $IC_{50}$, i.e. the inhibitory concentration that would produce a 50% decrease in the HIV-induced cytopathic effect. This effect is measured by the amount of test compound required to restore 50% of the cell growth of HIV-infected MT4 cells, compared to uninfected MT4 cell controls. $IC_{50}$ was calculated by RoboSage, Automated Curve Fitting Program.

For each assay plate, the results (of wells containing uninfected cells or infected cells with no compound were averaged, respectively. For measurements of compound-induced cytotoxicty, results from wells containing various compound concentrations and uninfected cells were compared to the average of uninfected cells without compound treatment. Percent of cells remaining is determined by the following formula:

Percent of cells remaining=(compound-treated uninfected cells/untreated uninfected cells)×100.

A level of percent of cells remaining of 79% or less indicates a significant level of direct compound-induced cytotoxicity for the compound at that concentration. When this condition occurs the results from the compound-treated infected wells at this concentration are not included in the calculation of $IC_{50}$.

For measurements of compound antiviral activity, results from wells containing various compound concentrations and infected cells are compared to the average of uninfected and infected cells without compound treatment. Percent inhibition of virus is determined by the following formula:

Percent inhibition of virus=(1−((ave. untreated uninfected cells−treated infected cells)/(ave. untreated uninfected cells−ave. untreated infected cells)))×100

REFERENCES

1. Averett, D. R., Anti-HIV compound assessment by two novel high capacity assays, *J. Virol. Methods* 23: 263-276, 1989.
2. Schwartz, O., et al., A rapid and simple colorimetric test for the study of anti-HIV agents, *AIDS Res. and Human Retroviruses* 4 (6): 441-447, 1988.
3. Daluge, S. M., et al., 5-chloro-2'3'-deoxy-3'fluorouridine (935U83), a selective anti-human immunodeficiency virus agent with an improved metabolic and toxicological profile. *Antimicro. Agents and Chemother.* 38 (7): 1590-1603, 1994.
4. Dornsife, R. E., et al., Anti-human immunodeficiency virus synergism by zidovudine (3'-azidothymidine) and didanosine (dideoxyinosine) contrasts with the additive inhibition of normal human marrow progenitor cells, *Antimicro. Agents and Chemother.* 35 (2): 322-328, 1991.
5. Promega Technical Bulletin #TB245. CellTiter 96 AQ One Solution Cell Proliferation Assay.

Results

TABLE 3

$EC_{50}$ values for representative compounds

| Example number | $IC_{50}$ (nM) |
| --- | --- |
| 1 | a |
| 2 | b |
| 3 | a |
| 4 | b |
| 5 | a |
| 6 | b |
| 7 | a |
| 8 | b |
| 9 | b |
| 10 | b |

TABLE 3-continued

EC$_{50}$ values for representative compounds

| Example number | IC$_{50}$ (nM) |
|---|---|
| 11 | b |
| 12 | a |
| 13 | b |
| 14 | b |
| 15 | b |
| 16 | c |
| 17 | b |
| 18 | b |
| 19 | b |
| 20 | b |
| 21 | b |
| 22 | b |
| 23 | b |
| 24 | a |
| 25 | b |
| 26 | a |
| 27 | a |
| 28 | a |
| 29 | b |
| 30 | b |
| 31 | b |
| 32 | b |
| 33 | a |
| 34 | b | a = <10 nM
b = 10-250 nM
c = 250-10,000 nM

Administration and Formulation

In another embodiment, there is provided a pharmaceutical composition comprising a pharmaceutically acceptable diluent and a therapeutically effective amount of a compound of Formula (I) or a pharmaceutically acceptable salt thereof.

The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formula I may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitric, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, Na$_2$CO$_3$, K$_2$CO$_3$, NaH, and potassium-t-butoxide.

Salts derived from pharmaceutically acceptable organic non-toxic bases include salts of primary, secondary, and tertiary amines, including in part, trimethylamine, diethylamine, N,N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences*, 17th ed., Mack Publishing Company, Easton, Pa., 1985, p. 1418, the disclosure of which is hereby incorporated by reference only with regards to the lists of suitable salts.

The compounds of the invention may exist in both unsolvated and solvated forms. The term solvate is used herein to describe a molecular complex comprising the compound of the invention and one or more pharmaceutically acceptable solvent molecules, for example, ethanol. The term hydrate is employed when said solvent is water. Pharmaceutically acceptable solvates include hydrates and other solvates wherein the solvent of crystallization may be isotopically substituted, e.g. D$_2$O, d$_6$-acetone, d$_6$-DMSO.

Compounds of Formula (I) containing one or more asymmetric carbon atoms can exist as two or more stereoisomers. Where a compound of Formula (I) contains an alkenyl or alkenylene group or a cycloalkyl group, geometric cis/trans (or Z/E) isomers are possible. Where the compound contains, for example, a keto or oxime group or an aromatic moiety, tautomeric isomerism (tautomerism) can occur. It follows that a single compound may exhibit more than one type of isomerism.

Included within the scope of the claimed compounds present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labelled compounds of formula (I) can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be administered as prodrugs. Thus, certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as prodrugs.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages.

In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used, the route and form of administration, and other factors. The drug can be administered more than once a day, such as once or twice a day.

Therapeutically effective amounts of the chemical entities described herein may range from approximately 0.01 to 200 mg per kilogram body weight of the recipient per day; such as about 0.01-100 mg/kg/day, for example, from about 0.1 to 50 mg/kg/day. Thus, for administration to a 70 kg person, the dosage range may be about 7-3500 mg per day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %.

What is claimed is:

1. A compound of the structure of Formula (I):

Formula I

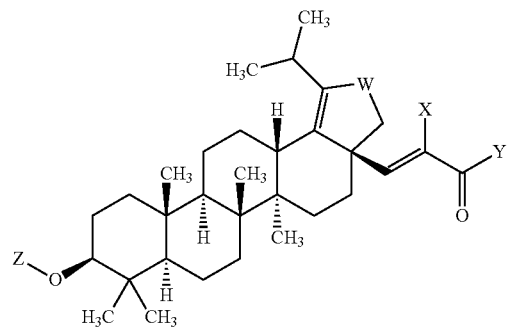

(I)

or a pharmaceutically acceptable salt thereof, wherein:

W is selected from —$CH_2$— or —C(=O)—;

X is selected from the group consisting of H, ($C_1$-$C_6$)alkyl, ($C_2$-$C_6$)alkenyl, ($C_2$-$C_6$)alkynyl, $NH_2$, —CN, —C(O)$R^6$, -(Q)$_n R^3$, —($C_1$-$C_6$)alkyl-N($R^3$)$_2$, —($C_1$-$C_6$)alkyl-$OR^3$—($C_1$-$C_6$)alkoxy, and amino-($C_1$-$C_6$)alkyl;

Y is selected from —$NR^1R^2$ or —$OR^5$;

Z is

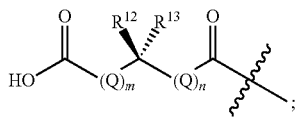

R$^1$ is selected from the group consisting of H, (C$_1$-C$_{12}$) alkyl, (C$_2$-C$_{12}$)alkenyl, (C$_2$-C$_{12}$)alkynyl, —(C$_1$-C$_6$)alkyl-N(R$^3$)$_2$, —(C$_1$-C$_6$)alkyl-OR$^3$;

R$^2$ is selected from the group consisting of H, (C$_1$-C$_{12}$) alkyl, (C$_2$-C$_{12}$)alkenyl, (C$_2$-C$_{12}$)alkynyl, and -(Q)$_n$R$^3$;

R$^1$ and R$^2$ can optionally join together along with the nitrogen to which they are joined to form a 4 to 12 membered heterocyclyl or heteroaryl ring, each independently containing one to three heteroatoms selected from —NR$^5$—, —O—, —S—, —S(O)—, or —SO$_2$—, and wherein said heterocyclyl or heteroaryl ring may be also optionally and independently substituted with one to three R$^{10}$ groups;

R$^3$ is independently selected from the group consisting of H, (C$_1$-C$_6$)alkyl, —R$^4$,

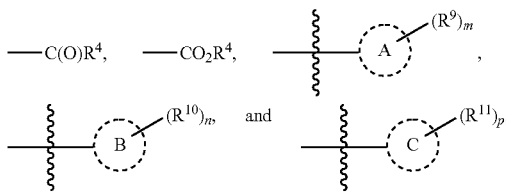

wherein:
A is (C$_5$-C$_{14}$)aryl,
B is selected from (C$_2$-C$_9$)heterocycle or (C$_2$-C$_9$)heteroaryl, each having one to three heteroatoms selected from S, N or O, and
C is (C$_3$-C$_8$)cycloalkyl;

R$^4$ is independently selected from the group consisting of halo, oxo, (C$_1$-C$_6$)alkyl, (C$_1$-C$_6$)alkoxy, (C$_3$-C$_8$)cycloalkyl; —CF$_3$, —OCF$_3$, —N(R$^5$)$_2$, —(CH$_2$)$_r$-heterocycle, —C(O)OH, —C(O)NH$_2$, and —NO$_2$;

R$^5$ is selected from the group consisting of H, (C$_1$-C$_6$)alkyl, and (C$_3$-C$_8$)cycloalkyl;

R$^6$ is independently H, (C$_1$-C$_6$)alkyl, (C$_3$-C$_8$)cycloalkyl, (C$_1$-C$_6$)alkoxy, haloalkyl, —OCF$_3$, —NR$^7$R$^8$, heterocycle, —(CH$_2$)$_r$NR$^7$R$^8$, —C(O)OH, —C(O)NH$_2$, wherein two R$^6$ groups can optionally be taken together with the carbon to which they are joined to form a 3 to 8 membered cycloalkyl ring, wherein the cycloalkyl ring may be optionally substituted by one to three R$^{10}$ groups;

R$^7$ and R$^8$ are independently selected from the group consisting of (C$_1$-C$_6$)alkyl, (C$_3$-C$_8$)cycloalkyl, -Q-aryl-(R$^4$)$_n$, —NR$^{14}$R$^{15}$, —C(O)CH$_3$, wherein R$^7$ and R$^8$ can optionally be taken together with the nitrogen to which they are joined to form a 4 to 8 membered heterocyclyl or heteroaryl ring containing one to three heteroatoms selected from —NR$^5$—, —O—, —S—, —S(O)—, or —SO$_2$—, wherein the heterocyclyl or heteroaryl ring may be optionally substituted by one to three R$^{10}$ groups;

R$^9$, R$^{10}$, and R$^{11}$ are independently selected from the group consisting of oxo, halo, (C$_1$-C$_6$)alkoxy, —R$^3$(R$^6$)$_q$, —OR$^3$(R$^6$)$_q$, nitro, —NR$^{14}$R$^{15}$, —SO$_2$R$^3$, (C$_1$-C$_6$) alkyl, —C(O)R$^7$, —YR$^1$R$^3$ and —CO(O)R$^2$, wherein any two R$^9$, R$^{10}$ or R$^{11}$ groups can optionally join to form a 3 to 8 membered cycloalkyl, aryl, heterocyclyl or heteroaryl ring, wherein the heterocyclyl or heteroaryl ring may contain one to three heteroatoms selected from —NR$^5$—, —O—, —S—, —S(O)—, or —SO$_2$—, and wherein the cycloalkyl, aryl, heterocyclyl or heteroaryl ring may be optionally substituted by one to three R$^4$ groups;

R$^{12}$ and R$^{13}$ are independently selected from the group consisting of H, (C$_1$-C$_6$)alkyl, (C$_3$-C$_8$)cycloalkyl, (C$_1$-C$_6$)alkoxy, —[C(R$^6$)$_2$]$_r$—, —O[C(R$^6$)$_2$]$_r$—, oxo, halo, —C(O)R$^7$, —NR$^1$R$^2$, and —CO(O)R$^2$, wherein R$^{12}$ and R$^{13}$ can optionally be taken together with the carbon to which they are joined to form a 3 to 8 membered cycloalkyl ring or 4 to 8 membered heterocyclyl ring containing one to three heteroatoms selected from —NR$^5$—, —O—, —S—, —S(O)—, —SO$_2$—, wherein the cycloalkyl ring or heterocyclyl ring may be optionally substituted by one to three R$^{10}$ groups;

R$^{14}$ and R$^{15}$ are independently selected from the group consisting of H, (C$_1$-C$_6$)alkyl, (C$_3$-C$_8$)cycloalkyl, (C$_1$-C$_6$)alkoxy, —R$^3$(R$^6$)$_q$, and —OR$^3$(R$^6$)$_q$, wherein R$^{14}$ and R$^{15}$ may be taken together with the nitrogen to which they are joined to form a 4 to 8 membered heterocyclyl or heteroaryl ring optionally containing one or three heteroatoms from —NR$^5$—, —O—, —S—, —S(O)—, or —SO$_2$—, wherein the heterocyclyl or heteroaryl ring may be optionally substituted by one to three R$^{10}$ groups;

Q is —[C(R$^6$)$_2$]$_r$—;
m and n are independently 0, 1, 2, 3, or 4;
p is independently 0, 1, 2, 3, or 4; and
r and q are independently 0, 1, 2, 3, or 4.

2. A compound of the structure of Formula (I):

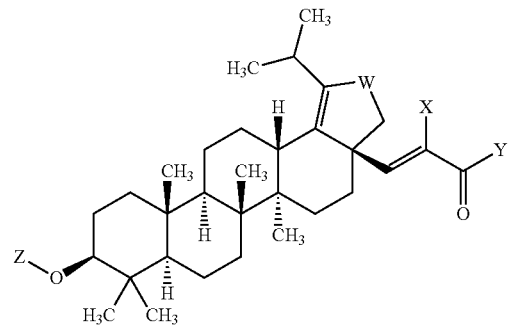

Formula I or a pharmaceutically acceptable salt thereof, wherein:
W is selected from —CH$_2$— or —C(=O)—;
X is selected from H or C$_1$-C$_6$-alkyl;
Y is selected from —NR$^1$R$^2$ or —OR$^5$;
Z is

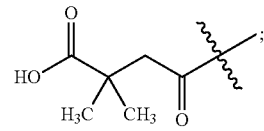 [SMILES: *C(=O)CC(C)(C)C(=O)O]

$R^1$ and $R^2$ are each independently selected from the group consisting of H, —($C_1$-$C_6$)alkyl-$OR^3$, and -$(Q)_n R^3$;

$R^3$ is selected from the group consisting of

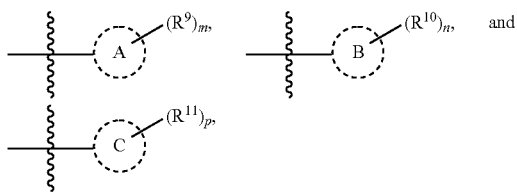

wherein:
A is ($C_5$-$C_{14}$)aryl,
B is selected from ($C_2$-$C_9$)heterocycle or ($C_2$-$C_9$)heteroaryl, each having one to three heteroatoms selected from S, N or O, and
C is ($C_3$-$C_7$)cycloalkyl;

$R^5$ is H;

$R^6$ is independently selected from H or ($C_1$-$C_6$)alkyl, wherein two $R^6$ alkyl groups can optionally be taken together with the carbon to which they are joined to form a 3 to 8 membered cycloalkyl ring, wherein the cycloalkyl ring may be optionally substituted by one to three $R^{10}$ groups;

$R^9$, $R^{10}$, and $R^{11}$ are independently selected from the group consisting of oxo, halo, ($C_1$-$C_6$)alkoxy, —$R^3(R^6)_q$, —$OR^3(R^6)_q$, nitro, —$NR^{14}R^{15}$, —$SO_2R^3$, ($C_1$-$C_6$) alkyl, —C(O)$R^7$, —$R^1YR^3$ and —CO(O)$R^2$;

$R^{12}$ and $R^{13}$ are independently selected from the group consisting of H, ($C_1$-$C_6$)alkyl, ($C_3$-$C_8$)cycloalkyl, ($C_1$-$C_6$)alkoxy, —$[C(R^6)_2]_r$—, —$O[C(R^6)_2]_r$—, oxo, halo, —C(O)$R^7$, —$NR^1R^2$, and —CO(O)$R^2$, wherein $R^{12}$ and $R^{13}$ can optionally be taken together with the carbon to which they are joined to form a 3 to 8 membered cycloalkyl ring or 4 to 8 membered heterocyclyl ring containing one to three heteroatoms selected from —$NR^5$—, —O—, —S—, —S(O)—, —$SO_2$—, wherein the cycloalkyl ring or heterocyclyl ring may be optionally substituted by one to three $R^{10}$ groups;

$R^{14}$ and $R^{15}$ are independently selected from the group consisting of H, ($C_1$-$C_6$)alkyl, ($C_3$-$C_8$)cycloalkyl, ($C_1$-$C_6$)alkoxy, —$R^3(R^6)_q$, and —$OR^3(R^6)_q$, wherein $R^{14}$ and $R^{15}$ may be taken together with the nitrogen to which they are joined to form a 4 to 8 membered heterocyclyl or heteroaryl ring optionally containing one or three heteroatoms from —$NR^5$—, —O—, —S—, —S(O)—, or —$SO_2$—, wherein the heterocyclyl or heteroaryl ring may be optionally substituted by one to three $R^{10}$ groups;

Q is —$[C(R^6)_2]_r$—;

m and n are independently 0, 1, 2, 3, or 4;
p is independently 0, 1, 2, 3, or 4; and
r and q are independently 0, 1, 2, 3, or 4.

3. The compound of claim 1 or a pharmaceutically acceptable salt thereof, wherein Z is

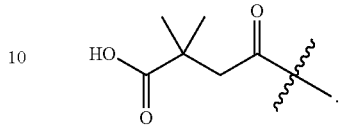

4. The compound of claim 1 or a pharmaceutically acceptable salt thereof, wherein Z is

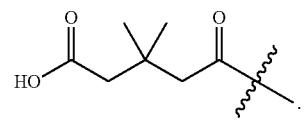 [SMILES: *C(=O)CC(C)(C)CC(=O)O]

5. The compound of claim 1 or a pharmaceutically acceptable salt thereof, wherein Z is

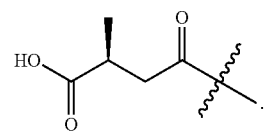 [SMILES: *C(=O)C[C@H](C)C(=O)O]

6. The compound of claim 1 or a pharmaceutically acceptable salt thereof, wherein Z is

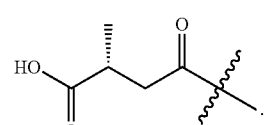

7. The compound of claim 1 or a pharmaceutically acceptable salt thereof, wherein W is —$CH_2$.

8. The compound of claim 1 or a pharmaceutically acceptable salt thereof, wherein W is carbonyl.

9. A compound or a pharmaceutically acceptable salt thereof of the structure:

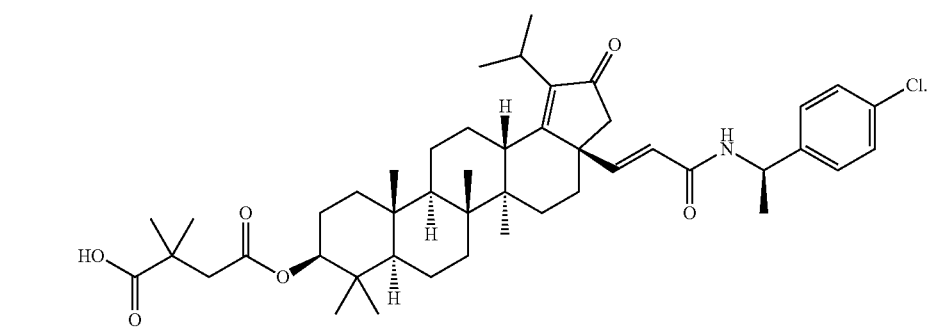

10. A compound or a pharmaceutically acceptable salt thereof of the structure:
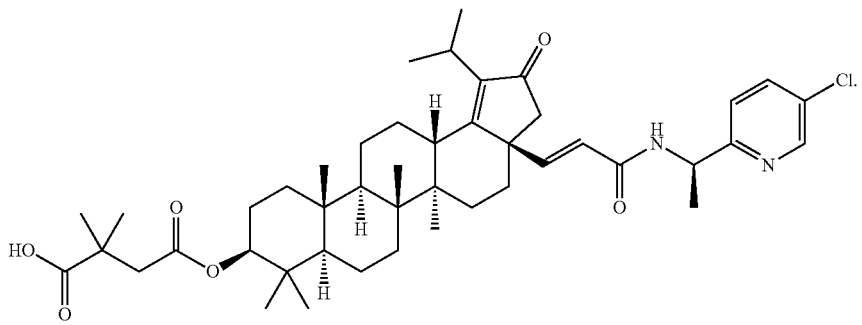
11. A compound or a pharmaceutically acceptable salt thereof of the structure:
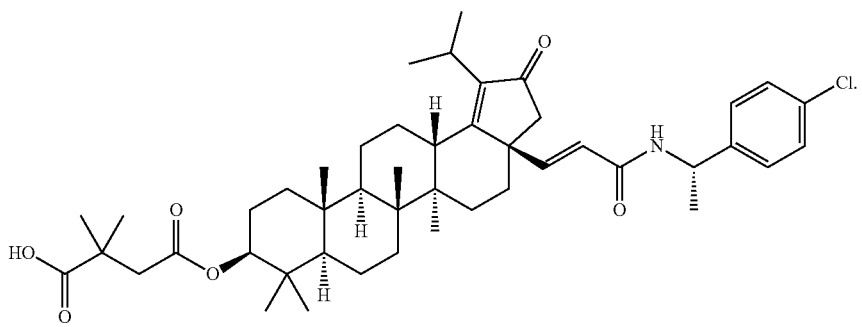
12. A compound or a pharmaceutically acceptable salt thereof of the structure:
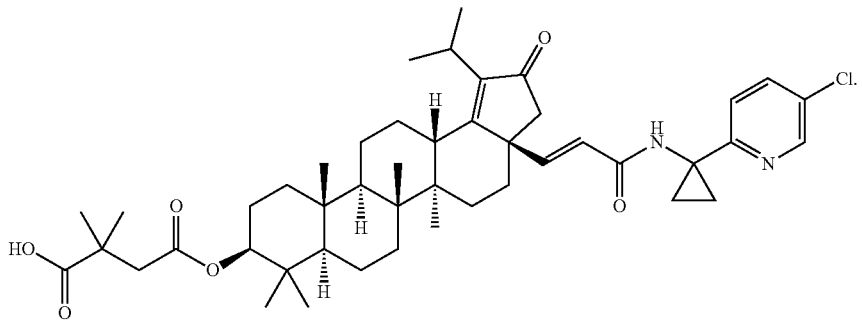
13. A compound or a pharmaceutically acceptable salt thereof of the structure:
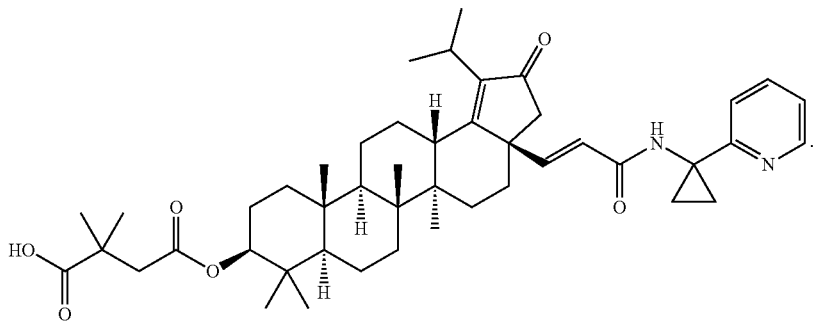

14. A compound or a pharmaceutically acceptable salt thereof of the structure:
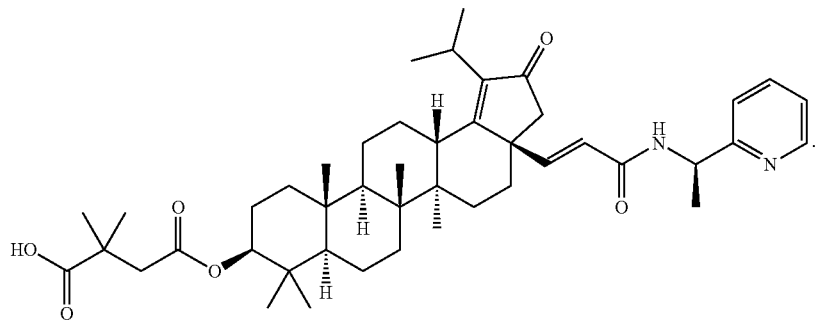
15. A compound or a pharmaceutically acceptable salt thereof of the structure:
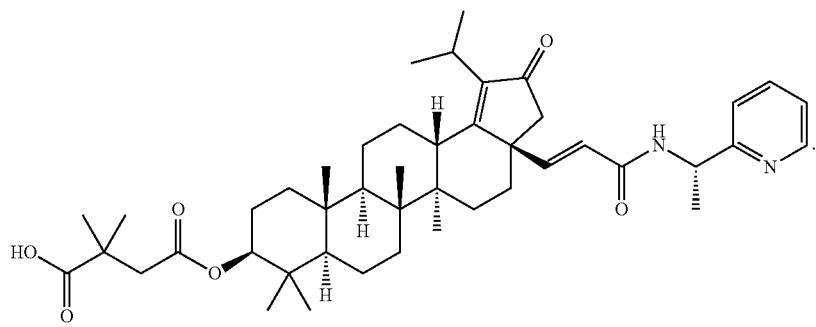
16. A compound or a pharmaceutically acceptable salt thereof of the structure:
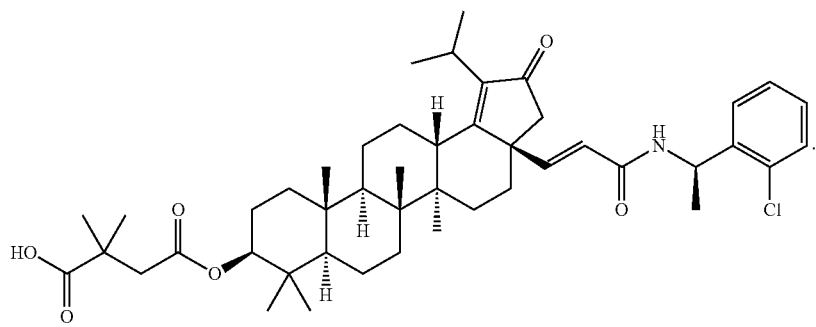
17. A compound or a pharmaceutically acceptable salt thereof of the structure:
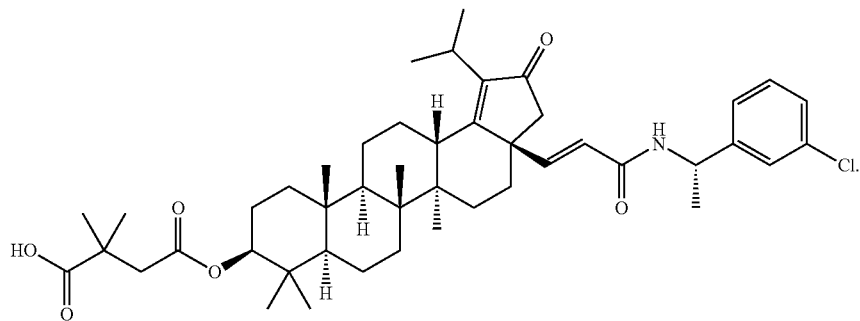

18. A compound or a pharmaceutically acceptable salt thereof of the structure:
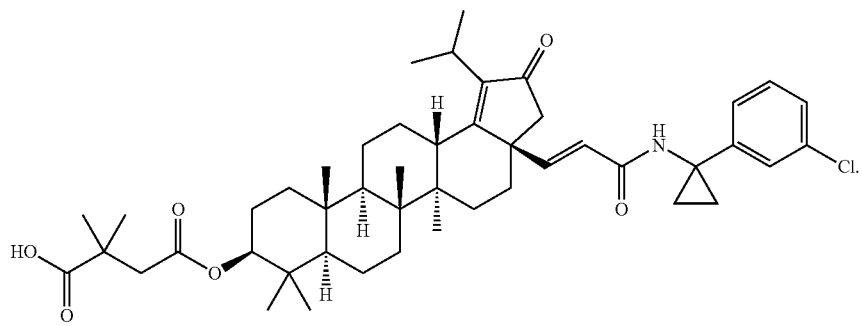
19. A compound or a pharmaceutically acceptable salt thereof of the structure:
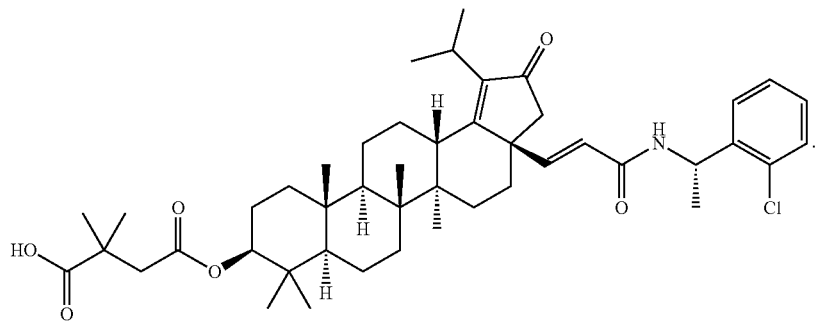
20. A compound or a pharmaceutically acceptable salt thereof of the structure:
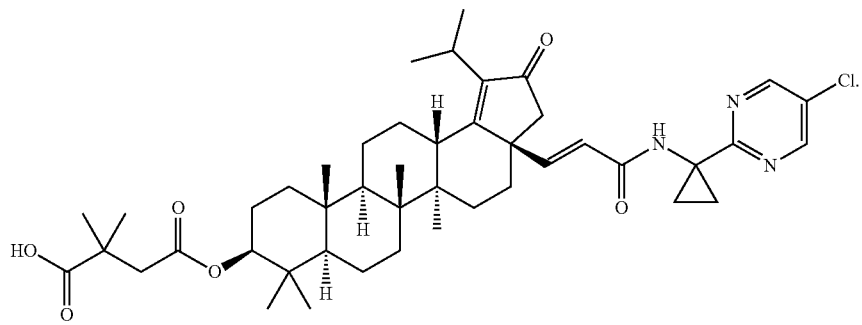
21. A compound or a pharmaceutically acceptable salt thereof of the structure:
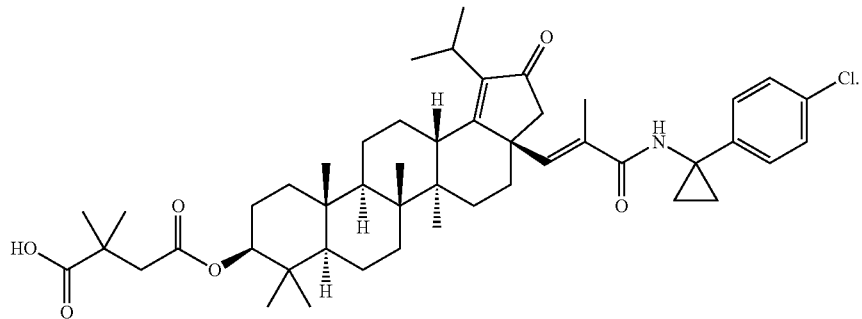

22. A compound or a pharmaceutically acceptable salt thereof of the structure:
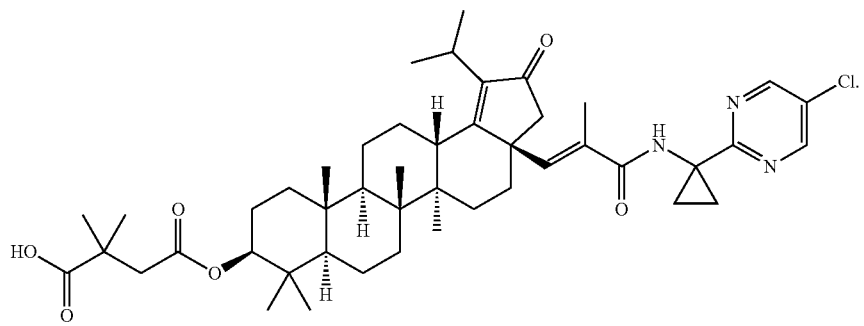
23. A compound or a pharmaceutically acceptable salt thereof of the structure:
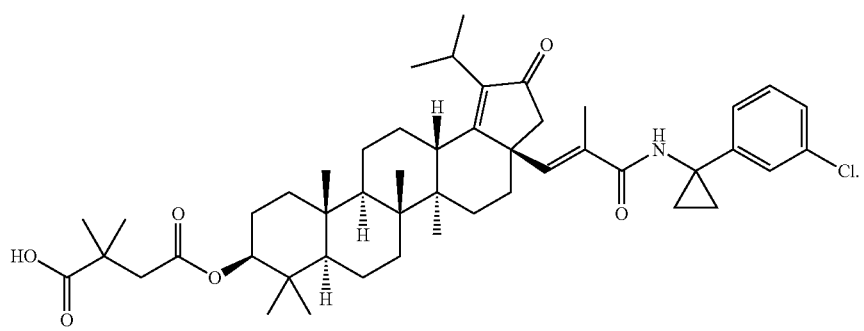
24. A compound or a pharmaceutically acceptable salt thereof of the structure:
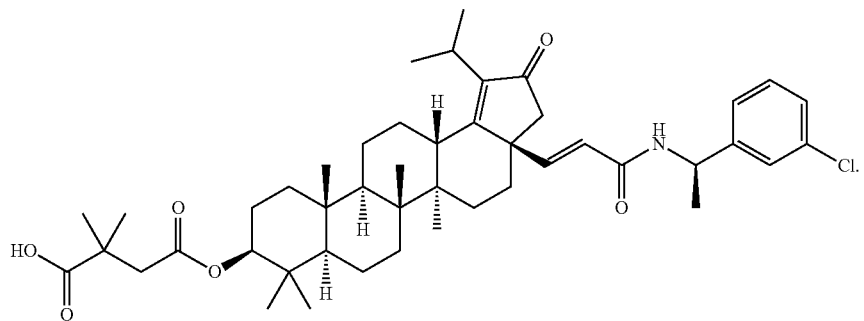
25. A compound or a pharmaceutically acceptable salt thereof of the structure:
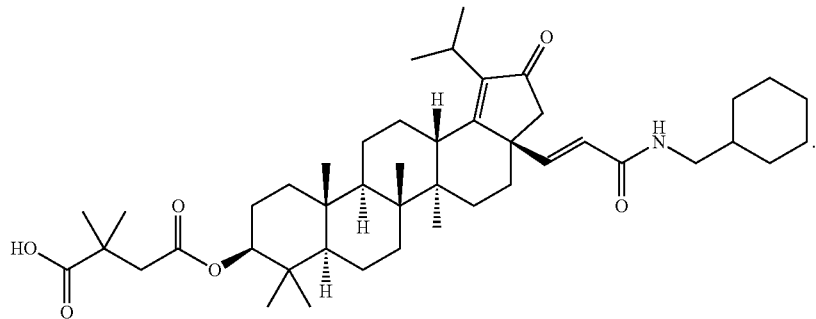

26. A compound or a pharmaceutically acceptable salt thereof of the structure:
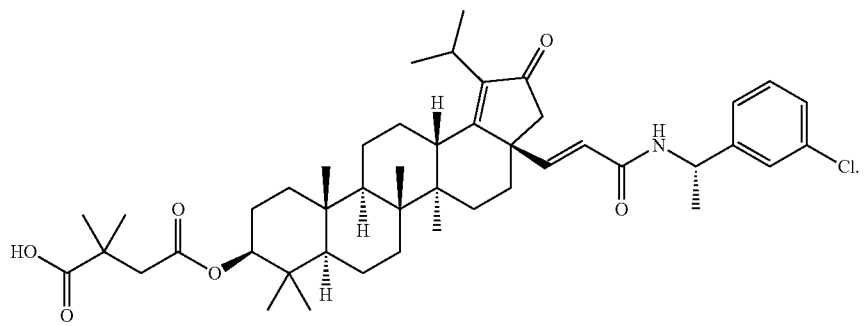
27. A pharmaceutical composition comprising 1) a compound of claim 1, or a pharmaceutically acceptable salt thereof; and 2) a pharmaceutically acceptable excipient.
* * * * *